(12) United States Patent
Martinelli et al.

(10) Patent No.: US 7,797,032 B2
(45) Date of Patent: *Sep. 14, 2010

(54) METHOD AND SYSTEM FOR NAVIGATING A CATHETER PROBE IN THE PRESENCE OF FIELD-INFLUENCING OBJECTS

(75) Inventors: Michael A. Martinelli, Winchester, MA (US); Paul Kessman, Broomfield, CO (US); Brad Jascob, Broomfield, CO (US)

(73) Assignee: Medtronic Navigation, Inc., Louisville, CO (US)

( * ) Notice: Subject to any disclaimer, the term of this patent is extended or adjusted under 35 U.S.C. 154(b) by 1377 days.

This patent is subject to a terminal disclaimer.

(21) Appl. No.: 10/252,258

(22) Filed: Sep. 23, 2002

(65) Prior Publication Data

US 2003/0117135 A1 Jun. 26, 2003

Related U.S. Application Data

(63) Continuation of application No. 09/589,779, filed on Jun. 8, 2000, now Pat. No. 6,493,573.

(60) Provisional application No. 60/161,991, filed on Oct. 28, 1999.

(51) Int. Cl.
 *A61B 5/05* (2006.01)
(52) U.S. Cl. ........................ 600/424; 600/407; 600/410; 600/422; 600/423; 600/433; 600/434; 128/899; 324/244; 324/245; 324/246; 324/247; 324/256; 324/257; 324/258; 324/259; 324/301; 324/302

(58) Field of Classification Search ......... 600/407–482; 128/899; 324/244–247, 301, 302, 256–259
See application file for complete search history.

(56) References Cited

U.S. PATENT DOCUMENTS 1,576,781 A 3/1926 Phillips
1,735,726 A 11/1929 Bornhardt (Continued)

FOREIGN PATENT DOCUMENTS

CA 964149 3/1975

(Continued)

OTHER PUBLICATIONS

Edward C. Benzel et al., "Magnetic Source Imaging: a Review of the Magnes System of Biomagnetic Technologies Incorporated," Nurosurgery, vol. 33, No. 2 (Aug. 1993), p. 252-259.

(Continued)

*Primary Examiner*—Brian Casler
*Assistant Examiner*—James Kish
(74) *Attorney, Agent, or Firm*—Harness, Dickey

(57) ABSTRACT

A system for and method of determining and compensating for the effect of a field influencing object on a field sensor, preferably a coil, that is within a navigational domain. The system includes a first and second transmitter to create signals. A signal processor is able to process the created signals. The method can include determining interference and/or a correct signal based on the two signals. Also, a shield can be provided to limit transmission of selected fields.

43 Claims, 22 Drawing Sheets

U.S. PATENT DOCUMENTS

| | | | |
|---|---|---|---|
| 2,407,845 A | 9/1946 | Nemeyer | |
| 2,650,588 A | 9/1953 | Drew | |
| 2,697,433 A | 12/1954 | Sehnder | |
| 3,016,899 A | 1/1962 | Stenvall | |
| 3,017,887 A | 1/1962 | Heyer | |
| 3,061,936 A | 11/1962 | Dobbeleer | |
| 3,073,310 A | 1/1963 | Mocarski | |
| 3,109,588 A | 11/1963 | Polhemus et al. | |
| 3,294,083 A | 12/1966 | Alderson | |
| 3,367,326 A | 2/1968 | Frazier | |
| 3,439,256 A | 4/1969 | Kähne et al. | |
| 3,526,798 A | 9/1970 | Sandstorm | |
| 3,577,160 A | 5/1971 | White | |
| 3,614,950 A | 10/1971 | Rabey | |
| 3,644,825 A | 2/1972 | Davis, Jr. et al. | |
| 3,674,014 A | 7/1972 | Tillander | 128/2.05 |
| 3,702,935 A | 11/1972 | Carey et al. | |
| 3,704,707 A | 12/1972 | Halloran | |
| 3,821,469 A | 6/1974 | Whetstone et al. | |
| 3,868,565 A | 2/1975 | Kuipers | 324/41 |
| 3,941,127 A | 3/1976 | Froning | |
| 3,983,474 A | 9/1976 | Kuipers | |
| 4,017,858 A | 4/1977 | Kuipers | |
| 4,037,592 A | 7/1977 | Kronner | |
| 4,052,620 A | 10/1977 | Brunnett | |
| 4,054,881 A | 10/1977 | Raab | 343/112 |
| 4,117,337 A | 9/1978 | Staats | |
| 4,137,361 A * | 1/1979 | Deffeyes et al. | 428/328 |
| 4,173,228 A | 11/1979 | Van Steenwyk et al. | 128/653 |
| 4,182,312 A | 1/1980 | Mushabac | |
| 4,202,349 A | 5/1980 | Jones | |
| 4,228,799 A | 10/1980 | Anichkov et al. | |
| 4,256,112 A | 3/1981 | Kopf et al. | |
| 4,262,306 A | 4/1981 | Renner | 358/93 |
| 4,287,809 A | 9/1981 | Egli et al. | 89/41 |
| 4,298,874 A | 11/1981 | Kuipers | |
| 4,314,251 A | 2/1982 | Raab | 343/112 |
| 4,317,078 A | 2/1982 | Weed et al. | 324/208 |
| 4,319,136 A | 3/1982 | Jinkins | |
| 4,328,548 A | 5/1982 | Crow et al. | |
| 4,328,813 A | 5/1982 | Ray | |
| 4,339,953 A | 7/1982 | Iwasaki | 73/654 |
| 4,341,220 A | 7/1982 | Perry | |
| 4,346,384 A | 8/1982 | Raab | |
| 4,358,856 A | 11/1982 | Stivender et al. | |
| 4,368,536 A | 1/1983 | Pfeiler | |
| 4,396,885 A | 8/1983 | Constant | 324/208 |
| 4,396,945 A | 8/1983 | DiMatteo et al. | |
| 4,403,321 A | 9/1983 | DiMarco | |
| 4,418,422 A | 11/1983 | Richter et al. | |
| 4,419,012 A | 12/1983 | Stephenson et al. | |
| 4,422,041 A | 12/1983 | Lienau | 324/207 |
| 4,431,005 A | 2/1984 | McCormick | 128/656 |
| 4,485,815 A | 12/1984 | Amplatz | |
| 4,506,676 A | 3/1985 | Duska | |
| 4,543,959 A | 10/1985 | Sepponen | |
| 4,548,208 A | 10/1985 | Niemi | |
| 4,571,834 A | 2/1986 | Fraser et al. | |
| 4,572,198 A | 2/1986 | Codrington | 128/653 |
| 4,583,538 A | 4/1986 | Onik et al. | |
| 4,584,577 A | 4/1986 | Temple | |
| 4,608,977 A | 9/1986 | Brown | |
| 4,613,866 A | 9/1986 | Blood | 343/448 |
| 4,617,925 A | 10/1986 | Laitinen | |
| 4,618,978 A | 10/1986 | Cosman | 378/164 |
| 4,621,628 A | 11/1986 | Bludermann | |
| 4,625,718 A | 12/1986 | Olerud et al. | |
| 4,638,798 A | 1/1987 | Shelden et al. | |
| 4,642,786 A | 2/1987 | Hansen | 364/559 |
| 4,645,343 A | 2/1987 | Stockdale et al. | |
| 4,649,504 A | 3/1987 | Krouglicof et al. | 364/559 |
| 4,651,732 A | 3/1987 | Frederick | |
| 4,653,509 A | 3/1987 | Oloff et al. | |
| 4,659,971 A | 4/1987 | Suzuki et al. | |
| 4,660,970 A | 4/1987 | Ferrano | |
| 4,673,352 A | 6/1987 | Hansen | |
| 4,688,037 A | 8/1987 | Krieg | |
| 4,701,049 A | 10/1987 | Beckmann et al. | |
| 4,705,395 A | 11/1987 | Hageniers | |
| 4,705,401 A | 11/1987 | Addleman et al. | |
| 4,706,665 A | 11/1987 | Gouda | |
| 4,709,156 A | 11/1987 | Murphy et al. | |
| 4,710,708 A | 12/1987 | Rorden et al. | |
| 4,719,419 A | 1/1988 | Dawley | |
| 4,722,056 A | 1/1988 | Roberts et al. | |
| 4,722,336 A | 2/1988 | Kim et al. | |
| 4,723,544 A | 2/1988 | Moore et al. | |
| 4,727,565 A | 2/1988 | Ericson | |
| RE32,619 E | 3/1988 | Damadian | |
| 4,733,969 A | 3/1988 | Case et al. | |
| 4,737,032 A | 4/1988 | Addleman et al. | |
| 4,737,794 A | 4/1988 | Jones | 342/448 |
| 4,737,921 A | 4/1988 | Goldwasser et al. | |
| 4,742,356 A | 5/1988 | Kuipers | |
| 4,742,815 A | 5/1988 | Ninan et al. | |
| 4,743,770 A | 5/1988 | Lee | |
| 4,743,771 A | 5/1988 | Sacks et al. | |
| 4,745,290 A | 5/1988 | Frankel et al. | |
| 4,750,487 A | 6/1988 | Zanetti | |
| 4,753,528 A | 6/1988 | Hines et al. | |
| 4,761,072 A | 8/1988 | Pryor | |
| 4,764,016 A | 8/1988 | Johansson | |
| 4,771,787 A | 9/1988 | Wurster et al. | |
| 4,779,212 A | 10/1988 | Levy | |
| 4,782,239 A | 11/1988 | Hirose et al. | |
| 4,788,481 A | 11/1988 | Niwa | |
| 4,791,934 A | 12/1988 | Brunnett | |
| 4,793,355 A | 12/1988 | Crum et al. | |
| 4,794,262 A | 12/1988 | Sato et al. | |
| 4,797,907 A | 1/1989 | Anderton | |
| 4,803,976 A | 2/1989 | Frigg et al. | |
| 4,804,261 A | 2/1989 | Kirschen | |
| 4,805,615 A | 2/1989 | Carol | |
| 4,809,694 A | 3/1989 | Ferrara | |
| 4,821,200 A | 4/1989 | Öberg | |
| 4,821,206 A | 4/1989 | Arora | |
| 4,821,731 A | 4/1989 | Martinelli et al. | 128/662.06 |
| 4,822,163 A | 4/1989 | Schmidt | |
| 4,825,091 A | 4/1989 | Breyer et al. | |
| 4,829,373 A | 5/1989 | Leberl et al. | |
| 4,836,778 A | 6/1989 | Baumrind et al. | 433/69 |
| 4,838,265 A | 6/1989 | Cosman et al. | |
| 4,841,967 A | 6/1989 | Chang et al. | |
| 4,845,771 A | 7/1989 | Wislocki et al. | |
| 4,849,692 A | 7/1989 | Blood | 324/208 |
| 4,860,331 A | 8/1989 | Williams et al. | |
| 4,862,893 A | 9/1989 | Martinelli | |
| 4,869,247 A | 9/1989 | Howard, III et al. | |
| 4,875,165 A | 10/1989 | Fencil et al. | |
| 4,875,478 A | 10/1989 | Chen | |
| 4,884,566 A | 12/1989 | Mountz et al. | |
| 4,889,526 A | 12/1989 | Rauscher et al. | |
| 4,896,673 A | 1/1990 | Rose et al. | |
| 4,905,698 A | 3/1990 | Strohl, Jr. et al. | 128/653 |
| 4,923,459 A | 5/1990 | Nambu | |
| 4,931,056 A | 6/1990 | Ghajar et al. | |
| 4,945,305 A | 7/1990 | Blood | 324/207 |
| 4,945,914 A | 8/1990 | Allen | |
| 4,951,653 A | 8/1990 | Fry et al. | |
| 4,955,891 A | 9/1990 | Carol | |
| 4,961,422 A | 10/1990 | Marchosky et al. | |
| 4,977,655 A | 12/1990 | Martinelli | 29/25.35 |
| 4,989,608 A | 2/1991 | Ratner | 128/653 |
| 4,991,579 A | 2/1991 | Allen | 128/653 |

| | | | | | | |
|---|---|---|---|---|---|---|
| 5,002,058 A | 3/1991 | Martinelli | 128/662 | 5,274,551 A | 12/1993 | Corby, Jr. | 364/413.13 |
| 5,005,592 A | 4/1991 | Cartmell | 128/899 | 5,279,309 A | 1/1994 | Taylor et al. | 128/782 |
| 5,013,317 A | 5/1991 | Cole et al. | | 5,285,787 A | 2/1994 | Machida | |
| 5,016,639 A | 5/1991 | Allen | 128/653 | 5,291,199 A | 3/1994 | Overman et al. | |
| 5,017,139 A | 5/1991 | Mushabac | | 5,291,889 A | 3/1994 | Kenet et al. | |
| 5,027,818 A | 7/1991 | Bova et al. | | 5,295,483 A | 3/1994 | Nowacki et al. | 128/660.03 |
| 5,030,196 A | 7/1991 | Inoue | | 5,297,549 A | 3/1994 | Beatty et al. | |
| 5,030,222 A | 7/1991 | Calandruccio et al. | | 5,299,253 A | 3/1994 | Wessels | |
| 5,031,203 A | 7/1991 | Trecha | | 5,299,254 A | 3/1994 | Dancer et al. | 378/163 |
| 5,042,486 A | 8/1991 | Pfeiler et al. | 128/653 | 5,299,288 A | 3/1994 | Glassman et al. | 395/80 |
| 5,047,036 A | 9/1991 | Koutrouvelis | | 5,300,080 A | 4/1994 | Clayman et al. | |
| 5,050,608 A | 9/1991 | Watanabe et al. | 128/653 | 5,305,091 A | 4/1994 | Gelbart et al. | |
| 5,054,492 A | 10/1991 | Scribner et al. | 128/662.06 | 5,305,203 A | 4/1994 | Raab | |
| 5,057,095 A | 10/1991 | Fabian | | 5,306,271 A | 4/1994 | Zinreich et al. | |
| 5,059,789 A | 10/1991 | Salcudean | 250/206.1 | 5,307,072 A | 4/1994 | Jones, Jr. | |
| 5,078,140 A | 1/1992 | Kwoh | | 5,309,913 A | 5/1994 | Kormos et al. | 128/653.1 |
| 5,079,699 A | 1/1992 | Tuy et al. | | 5,315,630 A | 5/1994 | Sturm et al. | 378/64 |
| 5,086,401 A | 2/1992 | Glassman et al. | 395/94 | 5,316,024 A | 5/1994 | Hirschi et al. | 128/899 |
| 5,094,241 A | 3/1992 | Allen | | 5,318,025 A | 6/1994 | Dumoulin et al. | 128/653.2 |
| 5,097,839 A | 3/1992 | Allen | | 5,320,111 A | 6/1994 | Livingston | |
| 5,098,426 A | 3/1992 | Sklar et al. | | 5,325,728 A | 7/1994 | Zimmerman et al. | |
| 5,099,845 A | 3/1992 | Besz et al. | 128/653.1 | 5,325,873 A | 7/1994 | Hirschi et al. | 128/899 |
| 5,099,846 A | 3/1992 | Hardy | | 5,329,944 A | 7/1994 | Fabian et al. | |
| 5,105,829 A | 4/1992 | Fabian et al. | 128/899 | 5,330,485 A | 7/1994 | Clayman et al. | |
| 5,107,839 A | 4/1992 | Houdek et al. | | 5,333,168 A | 7/1994 | Fernandes et al. | |
| 5,107,843 A | 4/1992 | Aarnio et al. | | 5,353,795 A | 10/1994 | Souza et al. | 128/653.2 |
| 5,107,862 A | 4/1992 | Fabian et al. | | 5,353,800 A | 10/1994 | Pohndorf et al. | |
| 5,109,194 A | 4/1992 | Cantaloube | | 5,353,807 A | 10/1994 | DeMarco | |
| 5,119,817 A | 6/1992 | Allen | | 5,359,417 A | 10/1994 | Müller et al. | |
| 5,142,930 A | 9/1992 | Allen et al. | | 5,368,030 A | 11/1994 | Zinreich et al. | 128/653.1 |
| 5,143,076 A | 9/1992 | Hardy et al. | | 5,371,778 A | 12/1994 | Yanof et al. | |
| 5,152,288 A | 10/1992 | Hoenig et al. | 128/653.1 | 5,375,596 A | 12/1994 | Twiss et al. | 128/653.1 |
| 5,160,337 A | 11/1992 | Cosman | | 5,377,678 A | 1/1995 | Dumoulin et al. | 128/653.1 |
| 5,161,536 A | 11/1992 | Vilkomerson et al. | 128/660.07 | 5,383,454 A | 1/1995 | Bucholz | 128/653.1 |
| 5,170,789 A * | 12/1992 | Narayan et al. | 600/423 | 5,385,146 A | 1/1995 | Goldreyer | |
| 5,178,164 A | 1/1993 | Allen | | 5,385,148 A | 1/1995 | Lesh et al. | |
| 5,178,621 A | 1/1993 | Cook et al. | | 5,386,828 A | 2/1995 | Owens et al. | 128/653.1 |
| 5,186,174 A | 2/1993 | Schlondorff et al. | | 5,389,101 A | 2/1995 | Heilbrun et al. | 606/130 |
| 5,187,475 A | 2/1993 | Wagener et al. | 340/870.32 | 5,391,199 A | 2/1995 | Ben-Haim | 607/122 |
| 5,188,126 A | 2/1993 | Fabian et al. | | 5,394,457 A | 2/1995 | Leibinger et al. | |
| 5,190,059 A | 3/1993 | Fabian et al. | | 5,394,875 A | 3/1995 | Lewis et al. | |
| 5,193,106 A | 3/1993 | DeSena | | 5,397,329 A | 3/1995 | Allen | |
| 5,197,476 A | 3/1993 | Nowacki et al. | 128/660.03 | 5,398,684 A | 3/1995 | Hardy | |
| 5,197,965 A | 3/1993 | Cherry et al. | | 5,399,146 A | 3/1995 | Nowacki et al. | |
| 5,198,768 A | 3/1993 | Keren | 324/318 | 5,400,384 A | 3/1995 | Fernandes et al. | |
| 5,198,877 A | 3/1993 | Schulz | 356/375 | 5,402,801 A | 4/1995 | Taylor | 128/898 |
| 5,207,688 A | 5/1993 | Carol | | 5,408,409 A | 4/1995 | Glassman et al. | 364/413.13 |
| 5,211,164 A | 5/1993 | Allen | 128/653.1 | 5,413,573 A | 5/1995 | Koivukangas | |
| 5,211,165 A | 5/1993 | Dumoulin et al. | 128/653.1 | 5,417,210 A | 5/1995 | Funda et al. | 128/653.1 |
| 5,211,176 A | 5/1993 | Ishiguro et al. | | 5,419,325 A | 5/1995 | Dumoulin et al. | 128/653.2 |
| 5,212,720 A | 5/1993 | Landi et al. | | 5,423,334 A | 6/1995 | Jordan | |
| 5,214,615 A | 5/1993 | Bauer | 367/128 | 5,425,367 A | 6/1995 | Shapiro et al. | 128/653.1 |
| 5,219,351 A | 6/1993 | Teubner et al. | | 5,425,382 A | 6/1995 | Golden et al. | 128/899 |
| 5,222,499 A | 6/1993 | Allen et al. | 128/653.1 | 5,426,683 A | 6/1995 | O'Farrell, Jr. et al. | |
| 5,224,049 A | 6/1993 | Mushabac | | 5,426,687 A | 6/1995 | Goodall et al. | |
| 5,228,442 A | 7/1993 | Imran | 128/642 | 5,427,097 A | 6/1995 | Depp | |
| 5,230,338 A | 7/1993 | Allen et al. | | 5,429,132 A | 7/1995 | Guy et al. | 128/653.1 |
| 5,230,623 A | 7/1993 | Guthrie et al. | | 5,433,198 A | 7/1995 | Desai | |
| 5,233,990 A | 8/1993 | Barnea | | RE35,025 E | 8/1995 | Anderton | |
| 5,237,996 A | 8/1993 | Waldman et al. | | 5,437,277 A | 8/1995 | Dumoulin et al. | 128/653.1 |
| 5,249,581 A | 10/1993 | Horbal et al. | 128/664 | 5,443,066 A | 8/1995 | Dumoulin et al. | 128/653.1 |
| 5,251,127 A | 10/1993 | Raab | | 5,443,489 A | 8/1995 | Ben-Haim | 607/115 |
| 5,251,635 A | 10/1993 | Dumoulin et al. | 128/653.2 | 5,444,756 A | 8/1995 | Pai et al. | |
| 5,253,647 A | 10/1993 | Takahashi et al. | 128/653.1 | 5,445,144 A | 8/1995 | Wodicka et al. | 128/207.14 |
| 5,255,680 A | 10/1993 | Darrow et al. | 128/653.1 | 5,445,150 A | 8/1995 | Dumoulin et al. | 128/653.1 |
| 5,257,636 A | 11/1993 | White | 128/897 | 5,445,166 A | 8/1995 | Taylor | 128/897 |
| 5,257,998 A | 11/1993 | Ota et al. | | 5,446,548 A | 8/1995 | Gerig et al. | |
| 5,261,404 A | 11/1993 | Mick et al. | | 5,447,154 A | 9/1995 | Cinquin et al. | |
| 5,265,610 A | 11/1993 | Darrow et al. | 128/653.1 | 5,448,610 A | 9/1995 | Yamamoto et al. | |
| 5,265,611 A | 11/1993 | Hoenig et al. | 128/653.1 | 5,453,686 A | 9/1995 | Anderson | 324/207.17 |
| 5,269,759 A | 12/1993 | Hernandez et al. | 604/96 | 5,456,718 A | 10/1995 | Szymaitis | 623/11 |
| 5,271,400 A | 12/1993 | Dumoulin et al. | 128/653.2 | 5,457,641 A | 10/1995 | Zimmer et al. | |
| 5,273,025 A | 12/1993 | Sakiyama et al. | 128/6 | 5,458,718 A | 10/1995 | Venkitachalam | |

| | | | | | | |
|---|---|---|---|---|---|---|
| 5,464,446 A | | 11/1995 | Dreessen et al. | 5,697,377 A | 12/1997 | Wittkampf |
| 5,465,714 A | * | 11/1995 | Scheuing ............... 600/323 | 5,702,406 A | 12/1997 | Vilsmeier et al. |
| 5,469,847 A | | 11/1995 | Zinreich et al. | 5,711,299 A | 1/1998 | Manwaring et al. ...... 128/653.1 |
| 5,478,341 A | | 12/1995 | Cook et al. | 5,713,946 A | 2/1998 | Ben-Haim ................. 607/122 |
| 5,478,343 A | | 12/1995 | Ritter | 5,715,822 A | 2/1998 | Watkins |
| 5,480,422 A | | 1/1996 | Ben-Haim ................. 607/122 | 5,715,836 A | 2/1998 | Kliegis et al. |
| 5,480,439 A | | 1/1996 | Bisek et al. | 5,718,241 A | 2/1998 | Ben-Haim et al. ........ 128/702 |
| 5,483,951 A | | 1/1996 | Frassica et al. | 5,727,552 A | 3/1998 | Ryan |
| 5,483,961 A | | 1/1996 | Kelly et al. ............ 128/653.1 | 5,727,553 A | 3/1998 | Saad |
| 5,485,849 A | | 1/1996 | Panescu et al. | 5,729,129 A | 3/1998 | Acker ................... 324/207.12 |
| 5,487,391 A | | 1/1996 | Panescu | 5,730,129 A | 3/1998 | Darrow et al. ........... 128/653.1 |
| 5,487,729 A | | 1/1996 | Avellanet et al. ............ 604/96 | 5,730,130 A | 3/1998 | Fitzpatrick et al. |
| 5,487,757 A | | 1/1996 | Truckai et al. | 5,732,703 A | 3/1998 | Kalfas et al. ............ 128/653.1 |
| 5,490,196 A | | 2/1996 | Rudich et al. | 5,735,278 A | 4/1998 | Hoult et al. |
| 5,494,034 A | | 2/1996 | Schlondorff et al. | 5,738,096 A | 4/1998 | Ben-Haim ............... 128/653.1 |
| 5,503,416 A | | 4/1996 | Aoki et al. | 5,740,802 A | 4/1998 | Nafis et al. |
| 5,513,637 A | | 5/1996 | Twiss et al. ............. 128/653.1 | 5,740,808 A | 4/1998 | Panescu et al. |
| 5,514,146 A | | 5/1996 | Lam et al. | 5,741,214 A | 4/1998 | Ouchi et al. |
| 5,515,160 A | | 5/1996 | Schulz et al. | 5,742,394 A | 4/1998 | Hansen |
| 5,517,990 A | | 5/1996 | Kalfas et al. ............ 128/653.1 | 5,744,953 A | 4/1998 | Hansen |
| 5,531,227 A | | 7/1996 | Schneider | 5,748,767 A | 5/1998 | Raab |
| 5,531,520 A | | 7/1996 | Grimson et al. | 5,749,362 A | 5/1998 | Funda et al. ............. 128/653.1 |
| 5,542,938 A | | 8/1996 | Avellanet et al. ............ 604/280 | 5,749,835 A | 5/1998 | Glantz |
| 5,543,951 A | | 8/1996 | Moehrmann | 5,752,513 A | * 5/1998 | Acker et al. ................. 600/424 |
| 5,546,940 A | | 8/1996 | Panescu et al. | 5,752,976 A | 5/1998 | Duffin et al. |
| 5,546,949 A | | 8/1996 | Frazin et al. | 5,755,725 A | 5/1998 | Druais |
| 5,546,951 A | | 8/1996 | Ben-Haim ................. 128/702 | RE35,816 E | 6/1998 | Schulz |
| 5,551,429 A | | 9/1996 | Fitzpatrick et al. | 5,758,667 A | 6/1998 | Slettenmark ............... 128/899 |
| 5,558,091 A | | 9/1996 | Acker et al. ............ 128/653.1 | 5,760,335 A | * 6/1998 | Gilboa ........................ 174/385 |
| 5,566,681 A | | 10/1996 | Manwaring et al. | 5,762,064 A | 6/1998 | Polvani .................... 128/653.1 |
| 5,568,384 A | | 10/1996 | Robb et al. | 5,767,669 A | 6/1998 | Hansen et al. |
| 5,568,809 A | | 10/1996 | Ben-Haim ................. 128/656 | 5,767,960 A | 6/1998 | Orman |
| 5,572,999 A | | 11/1996 | Taylor et al. ............ 128/653.1 | 5,769,789 A | 6/1998 | Wang et al. |
| 5,573,533 A | | 11/1996 | Strul | 5,769,843 A | 6/1998 | Abela et al. |
| 5,575,794 A | | 11/1996 | Walus et al. | 5,769,861 A | 6/1998 | Vilsmeier |
| 5,575,798 A | | 11/1996 | Koutrouvelis | 5,772,594 A | 6/1998 | Barrick |
| 5,583,909 A | | 12/1996 | Hanover | 5,775,322 A | 7/1998 | Silverstein et al. |
| 5,588,430 A | | 12/1996 | Bova et al. ............ 128/653.1 | 5,776,064 A | 7/1998 | Kalfas et al. ................. 600/414 |
| 5,590,215 A | | 12/1996 | Allen | 5,777,720 A | 7/1998 | Shapiro et al. |
| 5,592,939 A | | 1/1997 | Martinelli ................. 128/653.1 | 5,782,765 A | 7/1998 | Jonkman |
| 5,595,193 A | | 1/1997 | Walus et al. | 5,787,886 A | 8/1998 | Kelly et al. ............. 128/653.1 |
| 5,596,228 A | | 1/1997 | Anderton et al. | 5,792,055 A | * 8/1998 | McKinnon ................. 600/410 |
| 5,600,330 A | | 2/1997 | Blood ........................ 342/463 | 5,795,294 A | 8/1998 | Luber et al. |
| 5,603,318 A | | 2/1997 | Heilbrun et al. ............ 128/630 | 5,797,849 A | 8/1998 | Vesely et al. |
| 5,611,025 A | | 3/1997 | Lorensen et al. | 5,799,055 A | 8/1998 | Peshkin et al. |
| 5,617,462 A | | 4/1997 | Spratt | 5,799,099 A | 8/1998 | Wang et al. |
| 5,617,857 A | | 4/1997 | Chader et al. ............ 128/653.1 | 5,800,352 A | 9/1998 | Ferre et al. ................. 600/407 |
| 5,619,261 A | | 4/1997 | Anderton | 5,800,535 A | 9/1998 | Howard, III |
| 5,622,169 A | | 4/1997 | Golden et al. ............ 128/653.1 | 5,802,719 A | 9/1998 | O'Farrell, Jr. et al. |
| 5,622,170 A | | 4/1997 | Schulz .................... 128/653.1 | 5,803,089 A | 9/1998 | Ferre et al. ................. 128/897 |
| 5,627,873 A | | 5/1997 | Hanover et al. | 5,807,252 A | 9/1998 | Hassfeld et al. |
| 5,628,315 A | | 5/1997 | Vilsmeier et al. | 5,810,008 A | 9/1998 | Dekel et al. |
| 5,630,431 A | | 5/1997 | Taylor ........................ 128/897 | 5,810,728 A | 9/1998 | Kuhn ........................ 600/410 |
| 5,636,644 A | | 6/1997 | Hart et al. | 5,810,735 A | 9/1998 | Halperin et al. |
| 5,638,819 A | | 6/1997 | Manwaring et al. | 5,820,553 A | 10/1998 | Hughes |
| 5,640,170 A | | 6/1997 | Anderson ................... 343/895 | 5,823,192 A | 10/1998 | Kalend et al. |
| 5,642,395 A | | 6/1997 | Anderton et al. | 5,823,958 A | 10/1998 | Truppe |
| 5,643,268 A | | 7/1997 | Vilsmeier et al. | 5,828,725 A | 10/1998 | Levinson |
| 5,645,065 A | | 7/1997 | Shapiro et al. ............ 128/653.1 | 5,828,770 A | 10/1998 | Leis et al. |
| 5,646,524 A | | 7/1997 | Gilboa | 5,829,444 A | 11/1998 | Ferre et al. ................. 128/897 |
| 5,647,361 A | | 7/1997 | Damadian ................. 128/683.2 | 5,831,260 A | 11/1998 | Hansen ...................... 250/221 |
| 5,662,111 A | | 9/1997 | Cosman ................... 128/653.1 | 5,833,608 A | 11/1998 | Acker .......................... 600/409 |
| 5,664,001 A | | 9/1997 | Tachibana et al. | 5,834,759 A | 11/1998 | Glossop |
| 5,669,801 A | * | 9/1997 | Lee ............................. 445/24 | 5,836,954 A | 11/1998 | Heilbrun et al. ............. 600/130 |
| 5,674,296 A | | 10/1997 | Bryan et al. | 5,840,024 A | 11/1998 | Taniguchi et al. ........... 600/424 |
| 5,676,673 A | | 10/1997 | Ferre et al. ................. 606/130 | 5,840,025 A | 11/1998 | Ben-Haim ................. 600/424 |
| 5,681,260 A | | 10/1997 | Ueda et al. | 5,843,076 A | 12/1998 | Webster, Jr. et al. |
| 5,682,886 A | | 11/1997 | Delp et al. | 5,848,967 A | 12/1998 | Cosman |
| 5,682,890 A | | 11/1997 | Kormos et al. | 5,851,183 A | 12/1998 | Bucholz ..................... 600/425 |
| 5,690,108 A | | 11/1997 | Chakeres | 5,865,846 A | 2/1999 | Bryan et al. |
| 5,694,945 A | | 12/1997 | Ben-Haim ................. 128/736 | 5,868,674 A | 2/1999 | Glowinski et al. ........... 600/410 |
| 5,695,500 A | | 12/1997 | Taylor et al. ................. 606/130 | 5,868,675 A | 2/1999 | Henrion et al. |
| 5,695,501 A | | 12/1997 | Carol et al. | 5,871,445 A | 2/1999 | Bucholz ..................... 600/407 |

| | | | | | | |
|---|---|---|---|---|---|---|
| 5,871,455 | A | 2/1999 | Ueno | 6,233,476 | B1 | 5/2001 | Strommer et al. |
| 5,871,487 | A | 2/1999 | Warner et al. | 6,246,231 | B1 * | 6/2001 | Ashe ................... 324/207.17 |
| 5,873,822 | A | 2/1999 | Ferre et al. ................. 600/407 | 6,259,942 | B1 | 7/2001 | Westermann et al. |
| 5,882,304 | A | 3/1999 | Ehnholm et al. | 6,273,896 | B1 | 8/2001 | Franck et al. |
| 5,884,410 | A | 3/1999 | Prinz | 6,285,902 | B1 * | 9/2001 | Kienzle et al. ............. 600/427 |
| 5,889,834 | A | 3/1999 | Vilsmeier et al. | 6,298,262 | B1 | 10/2001 | Franck et al. |
| 5,891,034 | A | 4/1999 | Bucholz ................... 600/426 | 6,314,310 | B1 | 11/2001 | Ben-Haim et al. |
| 5,891,157 | A | 4/1999 | Day et al. | 6,332,089 | B1 | 12/2001 | Acker et al. |
| 5,904,691 | A | 5/1999 | Barnett et al. | 6,341,231 | B1 | 1/2002 | Ferre et al. |
| 5,907,395 | A | 5/1999 | Schulz et al. | 6,351,659 | B1 | 2/2002 | Vilsmeier |
| 5,913,820 | A | 6/1999 | Bladen et al. .............. 600/407 | 6,352,363 | B1 | 3/2002 | Munger et al. |
| 5,920,395 | A | 7/1999 | Schulz ..................... 356/375 | 6,381,485 | B1 | 4/2002 | Hunter et al. |
| 5,921,992 | A | 7/1999 | Costales et al. | 6,424,856 | B1 | 7/2002 | Vilsmeier et al. |
| 5,923,727 | A | 7/1999 | Navab | 6,427,079 | B1 | 7/2002 | Schneider et al. |
| 5,928,248 | A | 7/1999 | Acker | 6,427,314 | B1 | 8/2002 | Acker |
| 5,938,603 | A | 8/1999 | Ponzi | 6,428,547 | B1 | 8/2002 | Vilsmeier et al. |
| 5,938,694 | A | 8/1999 | Jaraczewski et al. | 6,434,415 | B1 | 8/2002 | Foley et al. |
| 5,947,980 | A | 9/1999 | Jensen et al. | 6,437,567 | B1 | 8/2002 | Schenck et al. |
| 5,947,981 | A | 9/1999 | Cosman | 6,445,943 | B1 | 9/2002 | Ferre et al. |
| 5,950,629 | A | 9/1999 | Taylor et al. ............... 128/897 | 6,470,207 | B1 | 10/2002 | Simon et al. |
| 5,951,475 | A | 9/1999 | Gueziec et al. | 6,474,341 | B1 | 11/2002 | Hunter et al. |
| 5,951,571 | A | 9/1999 | Audette | 6,478,802 | B2 | 11/2002 | Kienzle, III et al. |
| 5,954,647 | A | 9/1999 | Bova et al. ................ 600/407 | 6,484,049 | B1 | 11/2002 | Seeley et al. |
| 5,957,844 | A | 9/1999 | Dekel et al. | 6,490,475 | B1 | 12/2002 | Seeley et al. |
| 5,964,796 | A | 10/1999 | Imran | 6,493,573 | B1 * | 12/2002 | Martinelli et al. ........... 600/424 |
| 5,967,980 | A | 10/1999 | Ferre et al. ................. 600/424 | 6,498,944 | B1 | 12/2002 | Ben-Haim et al. |
| 5,967,982 | A | 10/1999 | Barnett | 6,499,488 | B1 | 12/2002 | Hunter et al. |
| 5,968,047 | A | 10/1999 | Reed | 6,516,046 | B1 | 2/2003 | Fröhlich et al. |
| 5,971,997 | A | 10/1999 | Guthrie et al. | 6,527,443 | B1 | 3/2003 | Vilsmeier et al. |
| 5,976,156 | A | 11/1999 | Taylor et al. ............... 606/130 | 6,551,325 | B2 | 4/2003 | Neubauer et al. |
| 5,980,535 | A | 11/1999 | Barnett et al. | 6,584,174 | B2 | 6/2003 | Schubert et al. |
| 5,983,126 | A | 11/1999 | Wittkampf | 6,593,884 | B1 * | 7/2003 | Gilboa et al. ............... 342/448 |
| 5,987,349 | A | 11/1999 | Schulz ..................... 600/427 | 6,609,022 | B2 | 8/2003 | Vilsmeier et al. |
| 5,987,960 | A | 11/1999 | Messner et al. | 6,611,700 | B1 | 8/2003 | Vilsmeier et al. |
| 5,999,837 | A | 12/1999 | Messner et al. | 6,636,757 | B1 | 10/2003 | Jascob et al. |
| 5,999,840 | A | 12/1999 | Grimson et al. | 6,640,128 | B2 | 10/2003 | Vilsmeier et al. |
| 6,001,130 | A | 12/1999 | Bryan et al. | 6,694,162 | B2 | 2/2004 | Hartlep |
| 6,006,126 | A | 12/1999 | Cosman | 6,701,179 | B1 | 3/2004 | Martinelli et al. |
| 6,006,127 | A | 12/1999 | Van Der Brug et al. | 2001/0007918 | A1 | 7/2001 | Vilsmeier et al. |
| 6,013,087 | A | 1/2000 | Adams et al. | 2002/0095081 | A1 | 7/2002 | Vilsmeier |
| 6,014,580 | A | 1/2000 | Blume et al. | 2004/0024309 | A1 | 2/2004 | Ferre et al. |
| 6,016,439 | A | 1/2000 | Acker | 2004/0116803 | A1 | 6/2004 | Jascob et al. |
| 6,019,725 | A | 2/2000 | Vesely et al. ............... 600/447 | | | | |
| 6,024,695 | A | 2/2000 | Taylor et al. ............... 600/102 | | | FOREIGN PATENT DOCUMENTS | |
| 6,050,724 | A | 4/2000 | Schmitz et al. | | | | |
| 6,059,718 | A | 5/2000 | Taniguchi et al. | DE | | 3042343 A1 | 6/1982 |
| 6,063,022 | A | 5/2000 | Ben-Haim | DE | | 35 08 730 | 3/1985 |
| 6,071,288 | A | 6/2000 | Carol et al. | DE | | 37 17 871 | 5/1987 |
| 6,073,043 | A | 6/2000 | Schneider | DE | | 38 38 011 | 11/1988 |
| 6,076,008 | A | 6/2000 | Bucholz | DE | | 3831278 A1 | 3/1989 |
| 6,096,050 | A | 8/2000 | Audette | DE | | 42 13 426 | 4/1992 |
| 6,104,944 | A | 8/2000 | Martinelli .................. 600/424 | DE | | 42 25 112 | 7/1992 |
| 6,118,845 | A | 9/2000 | Simon et al. | DE | | 4233978 C1 | 4/1994 |
| 6,122,538 | A | 9/2000 | Sliwa, Jr. et al. ............ 600/407 | DE | | 197 15 202 | 4/1997 |
| 6,122,541 | A | 9/2000 | Cosman et al. | DE | | 197 47 427 | 10/1997 |
| 6,131,396 | A | 10/2000 | Duerr et al. | DE | | 197 51 761 | 11/1997 |
| 6,139,183 | A | 10/2000 | Graumann | DE | | 198 32 296 | 7/1998 |
| 6,147,480 | A | 11/2000 | Osadchy et al. | DE | | 10085137 | 7/2010 |
| 6,149,592 | A | 11/2000 | Yanof et al. | EP | | 0 062 941 | 3/1982 |
| 6,156,067 | A | 12/2000 | Bryan et al. | EP | | 0 119 660 | 9/1984 |
| 6,161,032 | A | 12/2000 | Acker ....................... 600/424 | EP | | 0 155 857 | 1/1985 |
| 6,165,181 | A | 12/2000 | Heilbrun et al. | EP | | 0 319 844 A1 | 1/1988 |
| 6,167,296 | A | 12/2000 | Shahidi | EP | | 0 326 768 | 12/1988 |
| 6,172,499 | B1 | 1/2001 | Ashe | EP | | 0419729 A1 | 9/1989 |
| 6,175,756 | B1 | 1/2001 | Ferre et al. | EP | | 0350996 A1 | 1/1990 |
| 6,178,345 | B1 | 1/2001 | Vilsmeier et al. | EP | | 0 651 968 A1 | 8/1990 |
| 6,194,639 | B1 | 2/2001 | Botella et al. | EP | | 0 427 358 | 10/1990 |
| 6,201,387 | B1 | 3/2001 | Govari | EP | | 0 456 103 | 5/1991 |
| 6,201,987 | B1 | 3/2001 | Dumoulin | EP | | 0 581 704 B1 | 7/1993 |
| 6,203,497 | B1 | 3/2001 | Dekel et al. | EP | | 0655138 B1 | 8/1993 |
| 6,211,666 | B1 | 4/2001 | Acker | EP | | 0894473 A2 | 1/1995 |
| 6,223,067 | B1 | 4/2001 | Vilsmeier | EP | | 0 908 146 | 10/1998 |
| 6,225,805 | B1 * | 5/2001 | Damadian et al. .......... 324/318 | EP | | 0 930 046 | 10/1998 |

| | | |
|---|---|---|
| EP | 0993804 A1 | 4/2000 |
| FR | 2417970 | 2/1979 |
| FR | 2 618 211 | 7/1987 |
| GB | 2 094 590 | 2/1982 |
| GB | 2 164 856 | 10/1984 |
| JP | 61-94639 | 10/1984 |
| JP | 62-327 | 6/1985 |
| JP | 63-240851 | 3/1987 |
| JP | 3-267054 | 3/1990 |
| JP | 2765738 | 6/1998 |
| WO | WO 88/09151 | 12/1988 |
| WO | WO 89/05123 | 6/1989 |
| WO | WO 90/05494 | 5/1990 |
| WO | WO 91/03982 | 4/1991 |
| WO | WO 91/04711 | 4/1991 |
| WO | WO 91/07726 | 5/1991 |
| WO | WO 92/03090 | 3/1992 |
| WO | WO 92/06645 | 4/1992 |
| WO | WO 94/04938 | 3/1994 |
| WO | WO 94/23647 | 10/1994 |
| WO | WO 94/24933 | 11/1994 |
| WO | WO 95/07055 | 3/1995 |
| WO | WO 96/11624 | 4/1996 |
| WO | WO 96/32059 | 10/1996 |
| WO | WO 97/49453 | 6/1997 |
| WO | WO 97/36192 | 10/1997 |
| WO | WO 98/08554 | 3/1998 |
| WO | WO 98/38908 | 9/1998 |
| WO | WO 99/38449 | 1/1999 |
| WO | WO 99/15097 | 4/1999 |
| WO | WO 99/52094 | 4/1999 |
| WO | WO 99/21498 | 5/1999 |
| WO | WO 99/23956 | 5/1999 |
| WO | WO 99/26549 | 6/1999 |
| WO | WO 99/27839 | 6/1999 |
| WO | WO 99/29253 | 6/1999 |
| WO | WO 99/33406 | 7/1999 |
| WO | WO 99/37208 | 7/1999 |
| WO | WO 99/60939 | 12/1999 |
| WO | WO-0010456 A1 | 3/2000 |
| WO | WO 01/30437 A1 | 5/2001 |
| WO | WO-0130256 A1 | 5/2001 |

OTHER PUBLICATIONS

"Prestige Cervical Disc System Surgical Technique", 12 pgs.
Adams et al., "Orientation Aid for Head and Neck Surgeons," Innov. Tech. Biol. Med., vol. 13, No. 4, 1992, pp. 409-424.
Barrick et al., "Prophylactic Intramedullary Fixation of the Tibia for Stress Fracture in a Professional Athlete," Journal of Orthopaedic Trauma, vol. 6, No. 2, pp. 241-244 (1992).
Barrick et al., "Technical Difficulties with the Brooker-Wills Nail in Acute Fractures of the Femur," Journal of Orthopaedic Trauma, vol. 6, No. 2, pp. 144-150 (1990).
Barrick, "Distal Locking Screw Insertion Using a Cannulated Drill Bit: Technical Note," Journal of Orthopaedic Trauma, vol. 7, No. 3, 1993, pp. 248-251.
Batnitzky et al., "Three-Dimensinal Computer Reconstructions of Brain Lesions from Surface Contours Provided by Computed Tomography: A Prospectus," Neurosurgery, vol. 11, No. 1, Part 1, 1982, pp. 73-84.
Bouazza-Marouf et al.; "Robotic-Assisted Internal Fixation of Femoral Fractures", IMECHE., pp. 51-58 (1995).
Brack et al., "Accurate X-ray Based Navigation in Computer-Assisted Orthopedic Surgery," CAR '98, pp. 716-722.
Bryan, "Bryan Cervical Disc System Single Level Surgical Technique", Spinal Dynamics, 2002, pp. 1-33.
Bucholz et al., "Variables affecting the accuracy of stereotactic localizationusing computerized tomography," Journal of Neurosurgery, vol. 79, Nov. 1993, pp. 667-673.
Champleboux et al., "Accurate Calibration of Cameras and Range Imaging Sensors: the NPBS Method," IEEE International Conference on Robotics and Automation, Nice, France, May 1992.
Champleboux, "Utilisation de Fonctions Splines pour la Mise au Point D'un Capteur Tridimensionnel sans Contact," Quelques Applications Medicales, Jul. 1991.
Cinquin et al., "Computer Assisted Medical Interventions," IEEE Engineering in Medicine and Biology, May/Jun. 1995, pp. 254-263.
Cinquin et al., "Computer Assisted Medical Interventions," International Advanced Robotics Programme, Sep. 1989, pp. 63-65.
Clarysse et al., "A Computer-Assisted System for 3-D Frameless Localization in Stereotaxic MRI," IEEE Transactions on Medical Imaging, vol. 10, No. 4, Dec. 1991, pp. 523-529.
Feldmar et al., "3D-2D Projective Registration of Free-Form Curves and Surfaces," Rapport de recherche (Inria Sophia Antipolis), 1994, pp. 1-44.
Foley et al., "Fundamentals of Interactive Computer Graphics," The Systems Programming Series, Chapter 7, Jul. 1984, pp. 245-266.
Foley et al., "Image-guided Intraoperative Spinal Localization," Intraoperative Neuroprotection, Chapter 19, 1996, pp. 325-340.
Foley, "The StealthStation: Three-Dimensional Image-Interactive Guidance for the Spine Surgeon," Spinal Frontiers, Apr. 1996, pp. 7-9.
Gildenberg et al., "Calculation of Stereotactic Coordinates from the Computed Tomographic Scan," Neurosurgery, vol. 10, No. 5, May 1982, pp. 580-586.
Gonzalez, "Digital Image Fundamentals," Digital Image Processing, Second Edition, 1987, pp. 52-54.
Gottesfeld Brown et al., "Registration of Planar Film Radiographs with Computer Tomography," Proceedings of MMBIA, Jun. '96, pp. 42-51.
Gueziec et al., "Registration of Computed Tomography Data to a Surgical Robot Using Fluoroscopy: A Feasibility Study," Computer Science/Mathematics, Sep. 27, 1996, 6 pages.
Hamadeh et al, "Kinematic Study of Lumbar Spine Using Functional Radiographies and 3D/2D Registration," TIMC UMR 5525—IMAG.
Hamadeh et al., "Automated 3-Dimensional Computed Tomographic and Fluorscopic Image Registration," Computer Aided Surgery (1998), 3:11-19.
Hamadeh et al., "Towards Automatic Registration Between CT and X-ray Images: Cooperation Between 3D/2D Registration and 2D Edge Detection," MRCAS '95, pp. 39-46.
Hatch, "Reference-Display System for the Integration of CT Scanning and the Operating Microscope," Thesis, Thayer School of Engineering, Oct. 1984, pp. 1-189.
Heilbrun et al., "Preliminary experience with Brown-Roberts-Wells (BRW) computerized tomography stereotaxic guidance system," Journal of Neurosurgery, vol. 59, Aug. 1983, pp. 217-222.
Henderson et al., "An Accurate and Ergonomic Method of Registration for Image-guided Neurosurgery," Computerized Medical Imaging and Graphics, vol. 18, No. 4, Jul.-Aug. 1994, pp. 273-277.
Hoerenz, "The Operating Microscope I. Optical Principles, Illumination Systems, and Support Systems," Journal of Microsurgery, vol. 1, 1980, pp. 364-369.
Hofstetter et al., "Fluoroscopy Based Surgical Navigation—Concept and Clinical Applications," Computer Assisted Radiology and Surgery, 1997, pp. 956-960.
Horner et al., "A Comparison of CT-Stereotaxic Brain Biopsy Techniques," Investigative Radiology, Sep.-Oct. 1984, pp. 367-373.
Hounsfield, "Computerized transverse axial scanning (tomography): Part 1. Description of system," British Journal of Radiology, vol. 46, No. 552, Dec. 1973, pp. 1016-1022.
Jacques et al., "A Computerized Microstereotactic Method to Approach, 3-Dimensionally Reconstruct, Remove and Adjuvantly Treat Small CNS Lesions," Applied Neurophysiology, vol. 43, 1980, pp. 176-182.
Jacques et al., "Computerized three-dimensional stereotaxic removal of small central nervous system lesion in patients," J. Neurosurg., vol. 53, Dec. 1980, pp. 816-820.
Joskowicz et al., "Computer-Aided Image-Guided Bone Fracture Surgery: Concept and Implementation," CAR '98, pp. 710-715.
Kelly et al., "Computer-assisted stereotaxic laser resection of intra-axial brain neoplasms," Journal of Neurosurgery, vol. 64, Mar. 1986, pp. 427-439.

Kelly et al., "Precision Resection of Intra-Axial CNS Lesions by CT-Based Stereotactic Craniotomy and Computer Monitored CO2 Laser," Acta Neurochirurgica, vol. 68, 1983, pp. 1-9.

Laitinen et al., "An Adapter for Computed Tomography-Guided, Stereotaxis," Surg. Neurol., 1985, pp. 559-566.

Laitinen et al., "Noninvasive multipurpose stereoadapter," Neurological Research, Jun. 1987, pp. 137-141.

Lavallee et al, "Matching 3-D Smooth Surfaces with their 2-D Projections using 3-D Distance Maps," SPIE, vol. 1570, Geometric Methods in Computer Vision, 1991, pp. 322-336.

Lavallee et al., "Computer Assisted Driving of a Needle into the Brain," Proceedings of the International Symposium CAR '89, Computer Assisted Radiology, 1989, pp. 416-420.

Lavallee et al., "Computer Assisted Interventionist Imaging: The Instance of Stereotactic Brain Surgery," North-Holland MEDINFO 89, Part 1, 1989, pp. 613-617.

Lavallee et al., "Computer Assisted Spine Surgery: A Technique for Accurate Transpedicular Screw Fixation Using CT Data and a 3-D Optical Localizer," TIMC, Faculte de Medecine de Grenoble.

Lavallee et al., "Image guided operating robot: a clinical application in stereotactic neurosurgery," Proceedings of the 1992 IEEE Internation Conference on Robotics and Automation, May 1992, pp. 618-624.

Lavallee et al., "Matching of Medical Images for Computed and Robot Assisted Surgery," IEEE EMBS, Orlando, 1991.

Lavallee, "A New System for Computer Assisted Neurosurgery," IEEE Engineering in Medicine & Biology Society 11th Annual International Conference, 1989, pp. 0926-0927.

Lavallee, "VI Adaption de la Methodologie a Quelques Applications Cliniques," Chapitre VI, pp. 133-148.

Leksell et al., "Stereotaxis and Tomography—A Technical Note," ACTA Neurochirurgica, vol. 52, 1980, pp. 1-7.

Lemieux et al., "A Patient-to-Computed-Tomography Image Registration Method Based on Digitally Reconstructed Radiographs," Med. Phys. 21 (11), Nov. 1994, pp. 1749-1760.

Levin et al., "The Brain: Integrated Three-dimensional Display of MR and PET Images," Radiology, vol. 172, No. 3, Sep. 1989, pp. 783-789.

Mazier et al., "Computer-Assisted Interventionist Imaging: Application to the Vertebral Column Surgery," Annual International Conference of the IEEE Engineering in Medicine and Biology Society, vol. 12, No. 1, 1990, pp. 0430-0431.

Mazier et al., Chirurgie de la Colonne Vertebrale Assistee par Ordinateur: Appication au Vissage Pediculaire, Innov. Tech. Biol. Med., vol. 11, No. 5, 1990, pp. 559-566.

Pelizzari et al., "Accurate Three-Dimensional Registration of CT, PET, and/or MR Images of the Brain," Journal of Computer Assisted Tomography, Jan./Feb. 1989, pp. 20-26.

Pelizzari et al., "Interactive 3D Patient-Image Registration," Information Processing in Medical Imaging, 12th International Conference, IPMI '91, Jul. 7-12, 136-141 (A.C.F. Colchester et al. eds. 1991).

Pelizzari et al., No. 528—"Three Dimensional Correlation of PET, CT and MRI Images," The Journal of Nuclear Medicine, vol. 28, No. 4, Apr. 1987, p. 682.

Phillips et al., "Image Guided Orthopaedic Surgery Design and Analysis," Trans Inst. MC, vol. 17, No. 5, 1995, pp. 251-264.

Potamianos et al., "Intra-Operative Imaging Guidance for Keyhole Surgery Methodology and Calibration," First International Symposium on Medical Robotics and Computer Assisted Surgery, Sep. 22-24, 1994, pp. 98-104.

Reinhardt et al., "CT-Guided 'Real Time' Stereotaxy," ACTA Neurochirurgica, 1989.

Roberts et al., "A frameless stereotaxic integration of computerized tomographic imaging and the operating microscope," J. Neurosurg., vol. 65, Oct. 1986, pp. 545-549.

Rosenbaum et al., "Computerized Tomography Guided Stereotaxis: A New Approach," Applied Neurophysiology, vol. 43, No. 3-5, 1980, pp. 172-173.

Sautot, "Vissage Pediculaire Assiste Par Ordinateur," Sep. 20, 1994.

Schueler et al., "Correction of Image Intensifier Distortion for Three-Dimensional X-Ray Angiography," SPIE Medical Imaging 1995, vol. 2432, pp. 272-279.

Selvik et al., "A Roentgen Stereophotogrammetric System," Acta Radiologica Diagnosis, 1983, pp. 343-352.

Shelden et al., "Development of a computerized microsteroetaxic method for localization and removal of minute CNS lesions under direct 3-D vision," J. Neurosurg., vol. 52, 1980, pp. 21-27.

Smith et al., "Computer Methods for Improved Diagnostic Image Display Applied to Stereotactic Neurosurgery," Automedical, vol. 14, 1992, pp. 371-382.

Smith et al., "The Neurostation™—A Highly Accurate, Minimally Invasive Solution to Frameless Stereotactic Neurosurgery," Computerized Medical Imaging and Graphics, vol. 18, Jul.-Aug. 1994, pp. 247-256.

The Laitinen Stereotactic System, E2-E6.

Viant et al., "A Computer Assisted Orthopaedic System for Distal Locking of Intramedullary Nails," Proc. of MediMEC '95, Bristol, 1995, pp. 86-91.

Watanabe et al., "Three-Dimensional Digitizer (Neuronavigator): New Equipment for Computed Tomography-Guided Stereotaxic Surgery," Surgical Neurology, vol. 27, No. 6, Jun. 1987, pp. 543-547.

Watanabe, "Neuronavigator," Igaku-no-Ayumi, vol. 137, No. 6, May 10, 1986, pp. 1-4.

Weese et al., "An Approach to 2D/3D Registration of a Vertebra in 2D X-ray Fluoroscopies with 3D CT Images," pp. 119-128.

Germano, "Instrumentation, Technique and Technology", Neurosurgery, vol. 37, No. 2, Aug. 1995, pp. 348-350.

Merloz, et al., "Computer Assisted Spine Surgery", Clinical Assisted Spine Surgery, No. 337, pp. 86-96.

Hatch, et al., "Reference-Display System for the Integration of CT Scanning and the Operating Microscope", Proceedings of the Eleventh Annual Northeast Bioengineering Conference, May 1985, pp. 252-254.

Adams et al., Computer-Assisted Surgery, IEEE Computer Graphics & Applications, pp. 43-51, (May 1990).

Bergstrom et al. Stereotaxic Computed Tomography, Am. J. Roentgenol, vol. 127 pp. 167-170 (1976).

Brown, R., M.D., A Stereotactic Head Frame for Use with CT Body Scanners, Investigative Radiology © J.B. Lippincott Company, pp. 300-304 (Jul.-Aug. 1979).

Bucholz, R.D., et al. Image-guided surgical techniques for infections and trauma of the central nervous system, Neurosurg. Clinics of N.A., vol. 7, No. 2, pp. 187-200 (1996).

Bucholz, R.D., et al., A Comparison of Sonic Digitizers Versus Light Emitting Diode-Based Localization, Interactive Image-Guided Neurosurgery, Chapter 16, pp. 179-200 (1993).

Bucholz, R.D., et al., Intraoperative localization using a three dimensional optical digitizer, SPIE—The Intl. Soc. for Opt. Eng., vol. 1894, pp. 312-322 (Jan. 17-19, 1993).

Bucholz, R.D., et al., Intraoperative Ultrasonic Brain Shift Monitor and Analysis, Stealth Station Marketing Brochure (2 pages) (undated).

Bucholz, R.D., et al., The Correction of Stereotactic Inaccuracy Caused by Brain Shift Using an Intraoperative Ultrasound Device, First Joint Conference, Computer Vision, Virtual Reality and Robotics in Medicine and Medical Robotics and Computer-Assisted Surgery, Grenoble, France, pp. 459-466 (Mar. 19-22, 1997).

Cutting M.D. et al., Optical Tracking of Bone Fragments During Craniofacial Surgery, Second Annual International Symposium on Medical Robotics and Computer Assisted Surgery, pp. 221-225, (Nov. 1995).

Friets, E.M., et al. A Frameless Stereotaxic Operating Microscope for Neurosurgery, IEEE Trans. on Biomed. Eng., vol. 36, No. 6, pp. 608-617 (Jul. 1989).

Gallen, C.C., et al., Intracranial Neurosurgery Guided by Functional Imaging, Surg. Neurol., vol. 42, pp. 523-530 (1994).

Galloway, R.L, Jr. et al, Optical localization for interactive, image-guided neurosurgery, SPIE, vol. 2164, pp. 137-145 (undated.

Galloway, R.L., et al., Interactive Image-Guided Neurosurgery, IEEE Trans. on Biomed. Eng., vol. 89, No. 12, pp. 1226-1231 (1992).

Gomez, C.R., et al., Transcranial Doppler Ultrasound Following Closed Head Injury: Vasospasm or Vasoparalysis?, Surg. Neurol., vol. 35, pp. 30-35 (1991).

Grimson, W.E.L., An Automatic Registration Method for Frameless Stereotaxy, Image Guided Surgery, and enhanced Reality Visualization, IEEE, pp. 430-436 (1994).

Grimson, W.E.L., et al., Virtual-reality technology is giving surgeons the equivalent of x-ray vision helping them to remove tumors more effectively, to minimize surgical wounds and to avoid damaging critical tissues, Sci. Amer., vol. 280, No. 6, pp. 62-69 (Jun. 1999).

Guthrie, B.L., Graphic-Interactive Cranial Surgery: The Operating Arm System, Handbook of Stereotaxy Using the CRW Apparatus, Chapter 13, pp. 193-211 (undated.

Hardy, T., M.D., et al., CASS: A Program for Computer Assisted Stereotaxic Surgery, The Fifth Annual Symposium on Comptuer Applications in Medical Care, Proceedings, Nov. 1-4, 1981, IEEE, pp. 1116-1126, (1981).

Heilbrun, M.D., Progressive Technology Applications, Neurosurgery for the Third Millenium, Chapter 15, J. Whitaker & Sons, Ltd., Amer. Assoc. of Neurol. Surgeons, pp. 191-198 (1992).

Heilbrun, M.P., Computed Tomography—Guided Stereotactic Systems, Clinical Neurosurgery, Chapter 31, pp. 564-581 (1983).

Heilbrun, M.P., et al., Stereotactic Localization and Guidance Using a Machine Vision Technique, Sterotact & Funct. Neurosurg., Proceed. of the Mtg. of the Amer. Soc. for Sterot. and Funct. Neurosurg. (Pittsburgh, PA) vol. 58, pp. 94-98 (1992).

Kall, B., The Impact of Computer and Imgaging Technology on Stereotactic Surgery, Proceedings of the Meeting of the American Society for Stereotactic and Functional Neurosurgery, pp. 10-22 (1987).

Kato, A., et al., A frameless, armless navigational system for computer-assisted neurosurgery, J. Neurosurg., vol. 74, pp. 845-849 (May 1991).

Kelly, P.J., Computer Assisted Stereotactic Biopsy and Volumetric Resection of Pediatric Brain Tumors, Brain Tumors in Children, Neurologic Clinics, vol. 9, No. 2, pp. 317-336 (May 1991).

Kelly, P.J., et al., Results of Computed Tomography-based Computer-assisted Stereotactic Resection of Metastatic Intracranial Tumors, Neurosurgery, vol. 22, No. 1, Part 1, 1988, pp. 7-17 (Jan. 1988).

Kelly, P.J., Computer-Directed Stereotactic Resection of Brain Tumors, Neurologica Operative Atlas, vol. 1, No. 4, pp. 299-313 (1991).

Kelly, P.J., Stereotactic Imaging, Surgical Planning and Computer-Assisted Resection of Intracranial Lesions: Methods and Results, Advances and Technical Standards in Neurosurgery, vol. 17, pp. 78-118, (1990).

Kim, W.S. et al., A Helmet Mounted Display for Telerobotics, IEEE, pp. 543-547 (1988).

Klimek, L., et al., Long-Term Experience with Different Types of Localization Systems in Skull-Base Surgery, Ear, Nose & Throat Surgery, Chapter 51, pp. 635-638 (undated).

Kosugi, Y., et al., An Articulated Neurosurgical Navigation System Using MRI and CT Images, IEEE Trans. on Biomed, Eng. vol. 35, No. 2, pp. 147-152 (Feb. 1988).

Krybus, W., et al., Navigation Support for Surgery by Means of Optical Position Detection, Computer Assisted Radiology Proceed. of the Intl. Symp. CAR '91 Computed Assisted Radiology, pp. 362-366 (Jul. 3-6, 1991).

Kwoh, Y.S., Ph.D., et al., A New Computerized Tomographic-Aided Robotic Stereotaxis System, Robotics Age, vol. 7, No. 6, pp. 17-22 (Jun. 1985).

Lavallee, S., et al., Computer Assisted Knee Anterior Cruciate Ligament Reconstruction First Clinical Tests, Proceedings of the First International Symposium on Medical Robotics and Computer Assisted Surgery, pp. 11-16 (Sep. 1994).

Lavallee, S., et al., Computer Assisted Medical Interventions, NATO ASI Series, vol. F 60, 3d Imaging in Medic., pp. 301-312 (1990).

Leavitt, D.D., et al., Dynamic Field Shaping to Optimize Stereotactic Radiosurgery, I.J. Rad. Onc. Biol. Physc., vol. 21, pp. 1247-1255 (1991).

Maurer, Jr., et al., Registration of Head CT Images to Physical Space Using a Weighted Combination of Points and Surfaces, IEEE Trans. on Med. Imaging, vol. 17, No. 5, pp. 753-761 (Oct. 1998).

McGirr, S., M.D., et al., Stereotactic Resection of Juvenile Pilocytic Astrocytomas of the Thalamus and Basal Ganglia, Neurosurgery, vol. 20, No. 3, pp. 447-452, (1987).

Ng, W.S. et al., Robotic Surgery—A First-Hand Experience in Transurethral Resection of the Prostate Surgery, IEEE Eng. in Med. and Biology, pp. 120-125 (Mar. 1993).

Penn, R.D., et al., Stereotactic Surgery with Image Processing of Computerized Tomographic Scans, Neurosurgery, vol. 3, No. 2, pp. 157-163 (Sep.-Oct. 1978).

Pixsys, 3-D Digitizing Accessories, by Pixsys (marketing brochure)(undated) (2 pages).

Reinhardt, H., et al., A Computer-Assisted Device for Intraoperative CT-Correlated Localization of Brain Tumors, pp. 51-58 (1988).

Reinhardt, H.F. et al., Sonic Stereometry in Microsurgical Procedures for Deep-Seated Brain Tumors and Vascular Malformations, Neurosurgery, vol. 32, No. 1, pp. 51-57 (Jan. 1993).

Reinhardt, H.F., et al., Mikrochirugische Entfernung tiefliegender Gefäßmifßbildungen mit Hilfe der Sonar-Stereometrie (Microsurgical Removal of Deep-Seated Vascular Malformations Using Sonar Stereometry). Ultraschall in Med. 12, pp. 80-83 (1991).

Reinhardt, Hans. F., Neuronavigation: A Ten-Year Review, Neurosurgery, pp. 329-341 (undated).

Simon, D.A., Accuracy Validation in Image-Guided Orthopaedic Surgery, Second Annual Intl. Symp. on Med. Rob. an Comp-Assisted surgery, MRCAS '95, pp. 185-192 (undated).

Smith, K.R., et al. Multimodality Image Analysis and Display Methods for Improved Tumor Localization in Stereotactic Neurosurgery, Annul Intl. Conf. of the IEEE Eng. in Med. and Biol. Soc., vol. 13, No. 1, p. 210 (1991).

Tan, K., Ph.D., et al., A frameless stereotactic approach to neurosurgical planning based on retrospective patient-image registration, J Neurosurgy, vol. 79, pp. 296-303 (Aug. 1993).

Thompson, et al., A System for Anatomical and Functional Mapping of the Human Thalamus, Computers and Biomedical Research, vol. 10, pp. 9-24 (1977).

Trobraugh, J.W., et al., Frameless Stereotactic Ultrasonography: Method and Applications, Computerized Medical Imaging and Graphics, vol. 18, No. 4, pp. 235-246 (1994).

Von Hanwhr et al., Foreword, Computerized Medical Imaging and Graphics, vol. 18, No. 4, pp. 225-228, (Jul.-Aug. 1994).

Wang, M.Y., et al., An Automatic Technique for Finding and Localizing Externally Attached Markers in CT and MR Volume Images of the Head, IEEE Trans. on Biomed. Eng., vol. 43, No. 6, pp. 627-637 (Jun. 1996).

Watanabe, E., M.D., et al., Open Surgery Assisted by the Neuronavigator, a Stereotactic, Articulated, Sensitive Arm, Neurosurgery, vol. 28, No. 6, pp. 792-800 (1991).

International Search Report mailed Dec. 6, 2002 for PCT/US02/17228 claiming benefit of U.S. Appl. No. 09/873,604 filed Jun. 4, 2001.

International Preliminary Examination Report mailed Aug. 8, 2001 for PCT/US00/29721 claiming benefit of U.S. Appl. No. 09/589,799, filed Jun. 8, 2000.

International Search Report mailed Jan. 24, 2001 for PCT/US00/29721 which claims benefit of U.S. Appl. No. 09/589,779 filed Jun. 8, 2000.

European Office Action mailed Aug. 14, 2009 for EP00972378 claiming benefit of PCT/US2000/029721, filed Oct. 27, 2000, which is based on U.S. Appl. No. 09/589,779, filed Jun. 8, 2000, which claims priority from U.S. Appl. No. 60/161,991, filed Oct. 28, 1999.

Supplementary European Search Report mailed Nov. 2, 2009 for EP02739569 claiming benefit of PCT/US02/17228, filed Jun. 3, 2002, claiming priority from U.S. Appl. No. 09/873,604, filed Jun. 4, 2001 (Patent No. 6,636,757, Issued Oct. 21, 2003).

* cited by examiner

METHOD AND SYSTEM FOR NAVIGATING A CATHETER PROBE IN THE PRESENCE OF FIELD-INFLUENCING OBJECTS

CROSS-REFERENCE TO RELATED APPLICATIONS

This application claims the benefit of United States Provisional Application No. 60/161,991, filed Oct. 28, 1999, the contents of which are incorporated herein by reference in their entirety, and from which priority is claimed.

This application is a continuation of U.S. patent application Ser. No. 09/589,779, filed Jun. 8, 2000, now U.S. Pat. No. 6,493,573 the contents of which are incorporated herein by reference in their entirety, and from which priority is claimed.

STATEMENT REGARDING FEDERALLY SPONSORED RESEARCH

Not Applicable

REFERENCE TO MICROFICHE APPENDIX

Not Applicable

CONCURRENTLY FILED APPLICATIONS

The following United States patent applications, which were concurrently filed with this one on Oct. 28, 1999, are fully incorporated herein by reference: Patient-shielding and Coil System, by Michael Martinelli, Paul Kessman and Brad Jascob; Navigation Information Overlay onto Ultrasound Imagery, by Paul Kessman, Troy Holsing and Jason Trobaugh; Coil Structures and Methods for Generating Magnetic Fields, by Brad Jascob, Paul Kessman and Michael Martinelli; Registration of Human Anatomy Integrated for Electromagnetic Localization, by Mark W. Hunter and Paul Kessman; System for Translation of Electromagnetic and Optical Localization Systems, by Mark W. Hunter and Paul Kessman; Surgical Communication and Power System, by Mark W. Hunter, Paul Kessman and Brad Jascob; and Surgical Sensor, by Mark W. Hunter, Sheri McCoid and Paul Kessman.

BACKGROUND OF INVENTION

The present invention relates to a navigation system for medical devices based on the use of magnetic fields. More particularly, this invention relates to a method and system for determining the position and orientation of a catheter probe being used during a surgical procedure in the presence of extraneous objects that may introduce extraneous magnetic fields.

Systems and methods for determining the position and orientation of surgical probes based on the use of magnetic fields are known. See, for example, U.S. Pat. No. 5,592,939, herein incorporated by reference. Such systems and methods generally rely on the ability to solve a known equation for a known field strength in order to obtain the unknown position and orientation variables. Although the focus here is a rigid catheter probe of known length, width and depth, one skilled in the art will appreciate that the techniques discussed here are equally applicable to other types of probes; for example, the techniques discussed here may be adapted to the use of a flexible probe.

In general, if the position in three-dimensional space of two points within the rigid probe is known, then the position and orientation of the probe itself is known. Each unknown point P in space corresponds to three unknown variables as shown in FIG. 1. These variables can be what are commonly called x, y, and z in a Cartesian system as is shown in FIG. 1, or they can be the variables r, $\theta$, and $\phi$ as are commonly used in spherical coordinates also as shown in FIG. 1. Two unknown points in space correspond to 6 unknown variables. However, when the two points are on a rigid catheter, and when the separation of the two points is known, one unknown variable is removed. Thus, the position and orientation of a rigid catheter probe in three-dimensions is a function of 5 unknown variables. These variables can be expressed in a form that utilizes both Cartesian and spherical coordinates. For example, the position of sensor coil 14 can be defined by three Cartesian coordinates x, y, and z as is shown in FIG. 2, and the orientation of sensor coil 14 along coil axis 21 is defined by the variables $\theta$ and $\phi$, also as shown in FIG. 2.

In order to solve for 5 unknown quantities, one typically requires 5 known linearly independent equations. One can obtain known equations that are linearly independent of each other by exposing a detector located on the catheter in an unknown position and orientation to known independent navigation fields. Thus, to obtain 5 known linearly independent equations requires a sampling of at least 5 known independent navigation fields. Nevertheless, current systems that utilize magnetic fields in order to determine position and orientation frequently sample more than 5 independent fields. See, for example, U.S. Pat. No. 5,592,939, herein incorporated by reference. One of the reasons for sampling more than 5 independent fields is to perform a self-consistency check. Ideally, every sampling above 5 should provide such a system with redundant information regarding position and orientation. However, in an operating room in practice, every sampling of a known navigation field beyond 5 yields slightly different results as to the position or orientation of the catheter probe. One of the reasons for this is the nearby presence extraneous objects that are conductive or ferromagnetic. Such objects respond to the known navigation field and introduce errors that can be large depending on the nature and relative position of the object.

For example, a conducting object within the area of influence of the known navigation field can develop what is known as an eddy current in response to the known navigation field. These eddy currents can, in turn, generate an extraneous magnetic field of unknown strength and orientation in the vicinity of the catheter. Depending upon the size of the object, this effect can be large.

In addition, an object with a ferromagnetic core will act to focus magnetic field flux lines through the core and thus distort the known navigation field, again, in an unknown manner. Often, objects with ferromagnetic and conductive cores are used in surgical settings, such as tools used to drill, ream and tap holes in the vertebrae of a patient.

In light of the foregoing, it is desirable to account for the effects of conducting objects that introduce eddy currents in response to a known navigation field.

It is further desirable to account for the effects of objects with ferromagnetic and conductive cores that introduce fluctuations in a known navigation field and that are often moved about near the periphery of the navigation field, such as surgical tools.

It is further desirable to account for the effects of objects that introduce arbitrary fluctuations in a known navigation field.

SUMMARY OF THE INVENTION

The foregoing and other objects are achieved by the invention which in one aspect comprises a correction system for determining the effect of an interfering object on a field sensor within a navigational domain. The system includes a first transmitter configured to project, into the navigational domain, field energy in a first waveform sufficient to induce a first signal value in the field sensor, where the first signal value is influenced by the interfering object. The system further includes a second transmitter configured to project, into the navigational domain, field energy in a second waveform sufficient to induce a second signal value in the field sensor, where the second signal value is also influenced by the interfering object. The system further includes a signal processor configured to receive the first signal value and the second signal value, and to determine the influences of the interfering object on the field sensor, to thereby permit a substantially precise location of the field sensor to be determined despite the presence of the interfering object.

In another embodiment of the invention, the field energy is magnetic field energy.

In another embodiment of the invention, the interfering object is an electrically conductive object.

In another embodiment of the invention, the field sensor includes an electrically conductive sensing coil.

In another embodiment of the invention, the first waveform is a sinusoidal waveform at a first frequency, and the second waveform is a sinusoidal waveform at a second frequency.

In another embodiment of the invention, the first transmitter and the second transmitter include three unidirectional coil sets, where each set is driven by a drive unit capable of driving the unidirectional coil set at the first frequency and at the second frequency. Further, the first and second transmitters include six delta coil sets, where each the set is driven by a drive unit capable of driving the delta coil set at the first frequency and the second frequency. In this embodiment, the three unidirectional coil sets and the six delta coils sets produce the field energy at the first and second frequencies.

In another embodiment of the invention, the three unidirectional coil sets include a first unidirectional coil set oriented so as to produce a substantially uniform amplitude field directed in an x direction, a second unidirectional coil set oriented so as to produce a substantially uniform amplitude field directed in a y direction, and a third unidirectional coil set oriented so as to produce a substantially uniform amplitude field directed in a z direction. In this embodiment, the x, y and z directions are substantially mutually orthogonal.

In another embodiment of the invention, the first unidirectional coil set has a first coil pair including a first coil element and a second coil element, and a second coil pair including a third coil element and a fourth coil element. The first coil element and the third coil element are disposed in a major surface of a platform, the second coil element is disposed in a first lateral wall of the platform, and the fourth coil element is disposed in a second lateral wall of the platform. In this embodiment, the first lateral wall and the second lateral wall are substantially normal to the major surface and substantially parallel to one another.

In another embodiment of the invention, the second unidirectional coil set has a first coil element and a second coil element disposed within a platform. The coil elements are spaced apart and substantially parallel to one another.

In another embodiment of the invention, the third unidirectional coil set has a first coil pair including a first coil element and a second coil element, and a second coil pair including a third coil element and a fourth coil element. The first coil element and the third coil element are disposed in a major surface of a platform, the second coil element is disposed in a first lateral wall of the platform, and the fourth coil element is disposed in a second lateral wall of the platform. In this embodiment, the first lateral wall and the second lateral wall are substantially normal to the major surface, and substantially parallel to one another.

In another embodiment of the invention, the six delta coil sets include a first pair of coil elements, a second pair of coil elements, and a third pair of coil elements. The coil elements are disposed so as to be substantially mutually coplanar within a major surface of a platform.

In another embodiment of the invention, each of the pairs of coil elements includes a long coil and a short coil, and the pairs of coils are disposed at equal angles on a circle about an axis extending substantially perpendicular to the major surface. In this embodiment, for each of the pairs of coils, a radius of the circle extends perpendicular to a direction of elongation of the pair, proceeding from the long coil to the short coil.

In another embodiment of the invention, each of the pairs of coil elements further includes at least one compensation coil, constructed and arranged to modify at least one termination point of the coil elements, so as to provide relatively a high spatial field gradient along two orthogonal axes, and substantially zero field amplitude along a third orthogonal axis.

In another embodiment of the invention, the signal processor includes a first sequencer configured to sequentially activate each of the three unidirectional coil sets and the six delta coil sets at the first frequency, and to measure the first signal value corresponding to each of the unidirectional and delta coil sets at the first frequency. The first sequencer further sequentially activates each of the three unidirectional coil sets and the six delta coil sets at the second frequency, and measures the second signal value corresponding to each of the unidirectional and delta coil sets at the second frequency. The signal processor further includes a processor configured to calculate, for each of the unidirectional and delta coil sets, and adjusted signal value as a predetermined function of the first signal value and the second signal value, so as to produce nine adjusted signal values, each corresponding to field energy from one of the unidirectional coil sets and the delta coil sets.

Another embodiment of the invention further includes a third transmitter configured to project into the navigational domain a third waveform sufficient to induce a third signal value in the field coil, where the third signal value is influenced by the interfering object. In this embodiment, the signal processor is further configured to receive the third signal value.

Another embodiment of the invention further includes a fourth transmitter configured to project into the navigational domain a fourth waveform sufficient to induce a fourth signal value ins aid field coil, the fourth signal value being influenced by the interfering object. In this embodiment, the signal processor is further configured to receive the fourth signal value.

Another embodiment of the invention further includes N-4 transmitters configured to project into the navigational domain N waveforms sufficient to induce N signal values in the field coil. The N signal values are influenced by the interfering object. The signal processor is further configured to receive N signal values.

In another aspect, the invention comprises a correction system for determining an effect of an interfering object on first and second field sensors in a navigational domain. The system includes a transmitter configured to project into the navigational domain, field energy sufficient to induce a first signal value in the first field sensor, and to induce a second signal value in the second field sensor. The system further includes a signal processor configured to receive the first signal value and the second signal value, and to determine the effect of the interfering object on the first field sensor, to thereby permit a substantially precise location of the first field sensor to be determined despite the presence of the interfering object.

In another embodiment of the invention, the field energy is magnetic field energy.

In another embodiment of the invention, the interfering object is a ferromagnetic and electrically conductive object.

In another embodiment of the invention, the field sensor includes an electrically conductive sensing coil.

In another embodiment of the invention, the transmitter includes three unidirectional coil sets. Each unidirectional coil set is driven by a unit capable of driving the unidirectional coil set at a first sinusoidal waveform at a first frequency. The transmitter further includes six delta coil sets, each of which is driven by a drive unit capable of driving the delta coil set at the first sinusoidal waveform at the first frequency, such that the three unidirectional coil sets and the six delta coil sets produce the field energy at the first frequency.

In another embodiment of the invention, the three unidirectional coil sets include a first unidirectional coil set oriented so as to produce a substantially uniform amplitude field directed in an x direction, a second unidirectional coil set oriented so as to produce a substantially uniform amplitude field directed in a y direction, and a third unidirectional coil set oriented so as to produce a substantially uniform amplitude field directed in a z direction, such that the x, y and z directions are substantially mutually orthogonal.

In another embodiment of the invention, the first unidirectional coil set has a first coil pair including a first coil element and a second coil element, and a second coil pair including a third coil element and a fourth coil element. The first coil element and the third coil element are disposed in a major surface of a platform, the second coil element is disposed in a first lateral wall of the platform, and the fourth coil element is disposed in a second lateral wall of the platform. The first lateral wall and the second lateral wall are substantially normal to the major surface and substantially parallel to one another.

In another embodiment of the invention, the second unidirectional coil set has a first coil element and a second coil element disposed within a platform, and the coil elements are spaced apart and substantially parallel to one another.

In another embodiment of the invention, the third unidirectional coil set has a first coil pair including a first coil element and a second coil element, and a second coil pair including a third coil element and a fourth coil element. The first coil element and the third coil element are disposed in a major surface of a platform, the second coil element is disposed in a first lateral wall of the platform, and the fourth coil element is disposed in a second lateral wall of the platform. The first lateral wall and the second lateral wall are substantially normal to the major surface and substantially parallel to one another.

In another embodiment of the invention, the six delta coil sets include a first pair of coil elements, a second pair of coil elements, and a third pair of coil elements. The coil elements are disposed so as to be substantially mutually coplanar within a major surface of a platform.

In another embodiment of the invention, each of the pairs of coil elements includes a long coil and a short coil, and the pairs of coils are disposed at equal angles on a circle about an axis extending substantially perpendicular to the major surface. For each of the pairs of coils, a radius of the circle extends perpendicular to a direction of elongation of the pair, proceeding from the long coil to the short coil.

In another embodiment of the invention, each of the pairs of coil elements further includes at least one compensation coil, constructed and arranged to modify at least one termination point of the coil elements, so as to provide relatively a high spatial field gradient along two orthogonal axes, and substantially zero field amplitude along a third orthogonal axis.

In another embodiment of the invention, the signal processor further includes a first sequencer configured to sequentially activate each of three unidirectional coil sets and six delta coil sets at the first frequency, and to measure the first signal value and the second signal value corresponding to each of the unidirectional and delta coil sets at the first frequency. The signal processor also includes a processor configured to calculate, for each of the unidirectional and delta coil sets, an adjusted signal value as a predetermined function of the first signal value and the second signal value, so as to produce nine adjusted signal values, each corresponding to field energy from one of the unidirectional coil sets and the delta coil sets.

In another aspect, the invention comprises a correction system for determining an effect of a field influencing shield device on a field sensor in a navigational domain. The correction system includes a transmitter configured to project into the navigational domain field energy sufficient to induce a signal value in the field sensor. The correction system further includes a storage device containing information corresponding to the fields energy in the navigational domain at selected locations within the navigational domain. The information includes shield information incorporating the effect of the field influencing shield device at the selected locations. The correction system further includes a processor for accessing the storage device and the signal value to determine the effect of the shield device on the field sensor, to thereby permit a substantially precise location of the field sensor to be determined despite the presence of the field influencing shield device.

In another embodiment of the invention, the field energy is magnetic field energy.

In another embodiment of the invention, the field sensor includes an electrically conductive sensing coil.

In another embodiment of the invention, the transmitter includes three unidirectional coil sets, each unidirectional coil set being driven by a unit capable of driving the unidirectional coil set at a first sinusoidal waveform at a first frequency. The transmitter further includes six delta coil sets, each the delta coil set being driven by a drive unit capable of driving the delta coil set at the first sinusoidal waveform at the first frequency, such that the three unidirectional coil sets and the six delta coil sets produce the field energy at the first frequency.

In another embodiment of the invention, the three unidirectional coil sets include a first unidirectional coil set oriented so as to produce a substantially uniform amplitude field directed in an x direction, a second unidirectional coil set oriented so as to produce a substantially uniform amplitude field directed in a y direction, and a third unidirectional coil set oriented so as to produce a substantially uniform amplitude field directed in a z direction, such that the x, y and z directions are substantially mutually orthogonal.

In another embodiment of the invention, the first unidirectional coil set has a first coil pair including a first coil element and a second coil element, and a second coil pair including a third coil element and a fourth coil element. The first coil element and the third coil element are disposed in a major surface of a platform, the second coil element is disposed in a first lateral wall of the platform, and the fourth coil element is disposed in a second lateral wall of the platform, wherein the first lateral wall and the second lateral wall are substantially normal to the major surface and substantially parallel to one another.

In another embodiment of the invention, the second unidirectional coil set having a first coil element and a second coil element disposed within a platform, the coil elements being spaced apart and substantially parallel to one another.

In another embodiment of the invention, the third unidirectional coil set has a first coil pair including a first coil element and a second coil element, and a second coil pair including a third coil element and a fourth coil element. The first coil element and the third coil element are disposed in a major surface of a platform, the second coil element is disposed in a first lateral wall of the platform, and the fourth coil element is disposed in a second lateral wall of the platform, wherein the first lateral wall and the second lateral wall are substantially normal to the major surface and substantially parallel to one another.

In another embodiment of the invention, the six delta coil sets include a first pair of coil elements, a second pair of coil elements, and a third pair of coil elements. The coil elements are disposed so as to be substantially mutually coplanar within a major surface of a platform.

In another embodiment of the invention, each of the pairs of coil elements includes a long coil and a short coil, and the pairs of coils are disposed at equal angles on a circle about an axis extending substantially perpendicular to the major surface. For each of the pairs of coils, a radius of the circle extends perpendicular to a direction of elongation of the pair, proceeding from the long coil to the short coil.

In another embodiment of the invention, each of the pairs of coil elements further includes at least one compensation coil, constructed and arranged to modify at least one termination point of the coil elements, so as to provide relatively a high spatial field gradient along two orthogonal axes, and substantially zero field amplitude along a third orthogonal axis.

In another embodiment of the invention, the processor further includes a first sequencer for sequentially activating each of the three unidirectional coils and the six delta coils at the first frequency, and measuring the signal value corresponding to each of the unidirectional and delta coils at the first frequency. The processor also includes a data manipulating device for manipulating, for each of the unidirectional and delta coils, the storage means as a predetermined function of the shield device, so as to produce nine sets of manipulated magnetic field values, each corresponding to navigational magnetic energy from one of the unidirectional coils and delta coils.

Another aspect of the invention comprises a method of determining a substantially precise location of a field sensor within a navigational domain influenced by a field interfering object. The method includes inducing within the field sensor a first signal value at a first waveform, the first signal value being influenced by the field interfering object. The method further includes inducing within the field sensor a second signal value at a second waveform, the second signal value being influenced by the field interfering object. The method also includes determining a correction to the first signal value for the effects of the field interfering object.

In another embodiment of the invention, determining a correction further includes calculating an adjusted signal value as a predetermined function of the first signal value and the second signal value.

Another aspect of the invention comprises a method of determining a substantially precise location of a first field sensor within a navigational domain influenced by a field interfering object. The method includes inducing within the first field sensor a first signal value, the first signal value being influenced by the field interfering object. The method further includes inducing within a second field sensor a second signal value, the second signal value being influenced by the field interfering object. The method also includes determining a correction to the first signal value for the effects of the field interfering object.

In another embodiment of the invention, determining a correction further includes calculating an adjusted signal value as a predetermined function of the first signal value and the second signal value.

Another aspect of the invention comprises a method of determining a substantially precise location of a field sensor within a navigational domain influenced by a field influencing shield device. The method includes inducing within the field sensor a first signal value, the first signal value being influenced by the field interfering object. The method further includes accessing information from a storage device, the information including shield information incorporating the effect of the field influencing shield device at selected locations. The method further includes determining a correction to the first signal value for the effects of the field influencing shield device.

In another embodiment of the invention, determining a correction further including manipulating the storage device as a predetermined function of the shield information, so as to produce a set of manipulated magnetic field values corresponding to the effects of the field influencing shield device.

In another aspect, the invention comprises a method of determining a substantially precise location of a field sensor within a navigational domain influenced by a field interfering object. The method includes sequentially projecting into the navigational domain, via three unidirectional coils and six delta coils, navigational energy at a first frequency, and measuring a first signal value in the field sensor corresponding to each of the three unidirectional coils and the six delta coils, so as to produce nine of the first signal values. The method further includes sequentially projecting into the navigational domain, via three unidirectional coils and six delta coils, the navigational energy at a second frequency, and measuring a second signal value in the field sensor corresponding to each of the three unidirectional coils and the six delta coils, so as to produce nine of the second signal values. The method further includes calculating, for each of the unidirectional and delta coils, an adjusted signal value as a predetermined function of the first signal value and the second signal value, so as to produce nine adjusted signal values, each corresponding to navigational magnetic energy from one of the unidirectional coils and delta coils. The method also includes forming three independent equations including three adjusted signal values corresponding to the unidirectional coils, three predetermined field magnitude values due to each of the unidirectional coils and corresponding to the navigational energy at a last navigational point of the sensing coil, and unknown orientation variables, and simultaneously solving the independent equations to determine the orientation variables corresponding to the compensated orientation of the sensing coil. The method also includes generating three lines and determining an intersection of the three lines. The intersection corresponds to the compensated position of the sensing coil. Each of the lines is generated from adjusted signal values corresponding to a pair of the delta coils, and predetermined field magnitude values due to the pair of delta coils and corresponding to the navigational energy at the last navigational point of the sensing coil while oriented according to the compensated orientation.

In another aspect, the invention comprises a method of determining a substantially precise location of a first field sensor within a navigational domain influenced by a field interfering object. The method includes sequentially projecting into the navigational domain, via three unidirectional coils and six delta coils, the navigational energy at a first frequency, measuring a first signal value in the field sensor corresponding to each of the three unidirectional coils and the six delta coils, so as to produce nine of the first signal values, and measuring a second signal value in a second field sensor corresponding to each of the three unidirectional coils and the six delta coils, so as to produce nine of the second signal values. The method further includes calculating, for each of the unidirectional and delta coils, an adjusted signal value as a predetermined function of the first signal value and the second signal value, so as to produce nine adjusted signal values, each corresponding to navigational magnetic energy from one of the unidirectional coils and delta coils. The method also includes forming three independent equations including three adjusted signal values corresponding to the unidirectional coils, three predetermined field magnitude values due to each of the unidirectional coils and corresponding to the navigational energy at a last navigational point of the sensing coil, and unknown orientation variables, and simultaneously solving the independent equations to determine the orientation variables corresponding to the compensated orientation of the sensing coil. The method also includes generating three lines and determining an intersection of the three lines, the intersection corresponding to the compensated position of the sensing coil. Each of the lines is generated from adjusted signal values corresponding to a pair of the delta coils, and predetermined field magnitude values due to the pair of delta coils and corresponding to the navigational energy at the last navigational point of the sensing coil while oriented according to the compensated orientation.

Another aspect of the invention comprises a method of determining a substantially precise location of a field sensor within a navigational domain influenced by a field influencing shield device. The method includes sequentially projecting into the navigational domain, via three unidirectional coils and six delta coils, the navigational energy at a first frequency, measuring a first signal value in the field sensor corresponding to each of the three unidirectional coils and the six delta coils, so as to produce nine of the first signal values. The method further includes forming three independent equations including three adjusted signal values corresponding to the unidirectional coils, three predetermined field magnitude values due to fields from each of the unidirectional coils and corresponding to the navigational energy at a last navigational point of the field sensor, the predetermined navigational energy at a first frequency, measuring a first signal value in the field sensor corresponding to each of the three unidirectional coils and the six delta coils, so as to produce nine of the first signal values, and measuring a second signal value in a second field sensor corresponding to each of the three unidirectional coils and the six delta coils, so as to produce nine of the second signal values. The method further includes calculating, for each of the unidirectional and delta coils, an adjusted signal value as a predetermined function of the first signal value and the second signal value, so as to produce nine adjusted signal values, each corresponding to navigational magnetic energy from one of the unidirectional coils and delta coils. The method also includes forming three independent equations including three adjusted signal values corresponding to the unidirectional coils, three predetermined field magnitude values due to each of the unidirectional coils and corresponding to the navigational energy at a last navigational point of the sensing coil, and unknown orientation variables, and simultaneously solving the independent equations to determine the orientation variables corresponding to the compensated orientation of the sensing coil. The method also includes generating three lines and determining an intersection of the three lines, the intersection corresponding to the compensated position of the sensing coil. Each of the lines is generated from adjusted signal values corresponding to a pair of the delta coils, and predetermined field magnitude values due to the pair of delta coils and corresponding to the navigational energy at the last navigational point of the sensing coil while oriented according to the compensated orientation.

Another aspect of the invention comprises a method of determining a substantially precise location of a field sensor within a navigational domain influenced by a field influencing shield device. The method includes sequentially projecting into the navigational domain, via three unidirectional coils and six delta coils, the navigational energy at a first frequency, and measuring a first signal value in the field sensor corresponding to each of the three unidirectional coils and the six delta coils, so as to produce nine of the first signal values. The method further includes forming three independent equations including three adjusted signal values corresponding to the unidirectional coils, three predetermined field magnitude values due to fields from each of the unidirectional coils and corresponding to the navigational energy at a last navigational point of the field sensor, the predetermined field magnitude values being manipulated so as to account for the shield device, and unknown orientation variables, and simultaneously solving the independent equations to determine the orientation variables corresponding to the compensated orientation of the sensing coil. The method also includes generating three lines and determining an intersection of the three lines, the intersection corresponding to the compensated position of the sensing coil. Each of the lines is generated from adjusted signal values corresponding to a pair of the delta coils, and predetermined field magnitude values due to the pair of delta coils and corresponding to the navigational energy at the last navigational point of the sensing coil while oriented according to the compensated orientation, the predetermined field magnitude values being manipulated so as to account for the effect of the shield device.

BRIEF DESCRIPTION OF DRAWINGS

The foregoing and other objects of this invention, the various features thereof, as well as the invention itself, may be more fully understood from the following description, when read together with the accompanying drawings in which.

DESCRIPTION OF THE PREFERRED EMBODIMENTS

Figure 1:
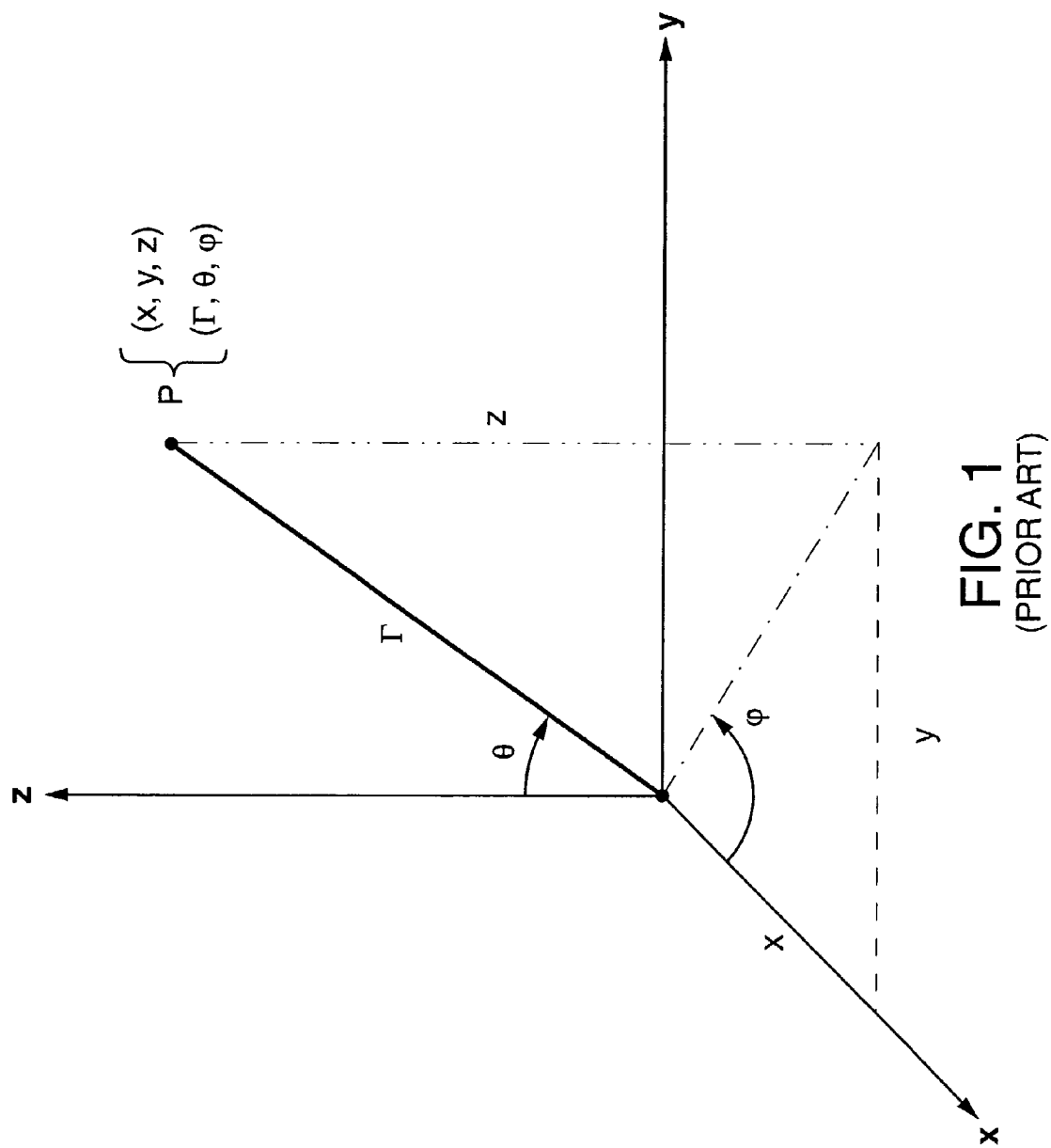
FIG. 1 is a graphical view of prior art methods of identifying a general point in three dimensional space.

The present invention is directed to a system and method for determining the position and orientation of a catheter or other suitable probe inserted into a selected body cavity of a patient undergoing a surgical procedure in the presence of field-influencing objects.

In one embodiment of the present invention, position and orientation data is determined from a series of measurements of voltage amplitudes induced within a sensing coil affixed to the distal end of the catheter probe as a result of the use of multiple waveforms. These voltage amplitudes, as a function of the waveforms, are induced in the sensing coil in response to known independent electromagnetic fields that are projected into the anatomical region of interest. The measurements provide information to compute the angular orientation and the positional coordinates of the sensing coil and account for the distortion of the known field by arbitrary conductors with field-induced eddy currents.

In another embodiment of the present invention, position and orientation data is determined from a series of measurements of voltage amplitudes induced within a sensing coil and a tool coil. The sensing coil is affixed to the distal end of the catheter probe. The tool coil is affixed to a field-influencing object with a ferromagnetic and conducting core. The field-influencing object, in the presence of a known electromagnetic field, distorts that field and influences the measurement of the sensing coil. The voltage amplitudes from both coils are stored and can be mathematically manipulated so as to isolate the effect of the field-influencing object on the sensing coil. Thus, the measurements of the induced voltage amplitudes on the sensing coil and on the tool coil provide information to account for the presence of the field-influencing object with a ferromagnetic and conductor core.

In another embodiment of the present invention, the position and orientation data is determined from a series of measurements of voltage amplitudes induced within a sensing coil affixed to the distal end of the catheter probe in the presence of a shield device. These voltage amplitudes are induced in the sensing coil in response to two fields. One of the fields is the known independent electromagnetic field projected into the anatomical region of interest from field coils. The other field is that of the known field as reflected from the shield device. The measurements of the induced voltage amplitudes and the knowledge of the geometry and effect of the shield device provide sufficient information to compute the angular orientation and the positional coordinates of this sensing coil in the presence of the shield device.

DEFINITIONS

As used herein, "sensing coil" refers to an electrically conductive, magnetically sensitive element that is responsive to time-dependent magnetic fields and generates an induced voltage as a function of and representative of the applied time-dependent magnetic field. The sensing coil is adaptable for secure engagement to the distal end of a catheter probe.

As used herein, "tool coil" refers to an electrically conductive, magnetically sensitive element that is responsive to time-dependent magnetic fields and generates an induced voltage as a function of and representative of the applied time-dependent magnetic field. The tool coil is adaptable for secure engagement to an object with a ferromagnetic and conducting core.

As used herein, "navigational domain" refers to a fully enclosed spatial region whose internal volume substantially encloses the complete prospective range of movement of the sensing coil. The navigational domain may be defined by any geometrical space, but preferably takes the form of a spherical volume. Under surgical operating conditions, the navigational domain will correspond to an anatomical region of the recumbent patient where surgical viewing or investigation is desired (e.g., a diseased area of tissue or an organ).

As used herein, "peripheral domain" refers to the spatial region outside of the navigational domain. Under surgical operating conditions, the peripheral domain may include the region that contains the operating table, or the region that encompasses other equipment within the operating room.

As used herein, "last navigational point" (hereinafter "the LNP") refers to the most recently determined location of the sensing coil before another iteration of the location algorithm is performed.

As used herein, "uniform amplitude field" refers to a magnetic field having a large magnetic field amplitude component in a specified direction and relatively smaller magnetic field amplitude components in the other directions. The uniform amplitude field is characterized by substantially uniform field amplitude values, throughout the navigational domain. In the x-y-z coordinate system used herein, where the uniform amplitude fields of interest are the x-directed, y-directed, and z-directed fields, the amplitudes of the induced voltage drops developed by such fields in the sensing coil are designated with superscripts $V^x$, $V^Y$, and $V^z$, respectively.

As used herein, "waveform" refers to the temporal shape of a magnetic field, illustrated graphically by a plot of the magnitude of a magnetic field as a function of time. A waveform in general can take on the characteristics of any form. For example, a waveform may be sinusoidal with angular frequency ω, which has the general form exp(-iωt) where i= $\sqrt{(-1)}$, ω is the angular frequency, t is the time, exp(n) denotes the natural base of logarithms e raised to the power n. A waveform can also be sawtooth in nature, or square in nature.

As used herein, "unidirectional coils" refer to a magnetic assembly that is operative to generate a uniform amplitude field (as defined above) within the navigational domain. A distinct magnetic assembly is employed for each uniform amplitude field. Although the unidirectional coils described herein are preferably implemented with a collection of appropriately designed magnetic coils, this implementation should not be construed as a limitation of the present invention. Rather, the unidirectional coils may be constructed from any magnetic configuration that is sufficient to generate the uniform amplitude fields.

As used herein, "vector gradient field" refers to a time-dependent magnetic field having nonzero vector gradient field components (i.e., magnetic field vector components with a high spatial gradient) in two of the three magnetic field components, and a substantially zero vector gradient field component in the remaining magnetic field component in an appropriately chosen coordinate system. For example, if the appropriately chosen coordinate system is an x-y-z coordinate system at a position R in the navigational domain, then the magnetic field amplitude $H^n(R)$ (a vector field) can be written as:

$$H^n(R)=(H_x^n(R),H_y^n(R),H_z^n(R))$$

where the components $H_x^n(R)$, $H_y^n(R)$, and $H_z^n(R)$ represent the magnetic field amplitude strengths of the nth coil (designated by the superscript "n") in the x-direction, y-direction, and z-direction, respectively and are individually scalar quantities. The value of a vector gradient of such a magnetic field amplitude $H^n(R)$ where the magnetic field has a substantially zero vector gradient component in the z-direction can be written as the following vector gradient (or tensor) field:

$$\vec{\nabla}H^n(R)=(\vec{\nabla}H_x^n(R),\vec{\nabla}H_y^n(R),0), \text{ where}$$

$$\vec{\nabla}H_x^n(R)\neq 0, \text{ and}$$

$$\vec{\nabla}H_y^n(R)\neq 0$$

and where the gradient operator $\vec{\nabla}$ has the usual representation in x-y-z coordinates:

$$\vec{\nabla} = \left(\frac{\partial}{\partial_x}, \frac{\partial}{\partial_y}, \frac{\partial}{\partial_z}\right)$$

In practical settings, a substantially zero vector gradient component is generated when the magnitude of the substantially zero vector gradient component value is small compared to the magnitude of the net vector resulting from the other two magnetic field components.

As used herein, "fixed orientation" with respect to a catheter probe refers to a catheter probe with constant values of orientation variables θ and φ, over a selected range of x, y, and z positional values.

As used herein, "constant signal surface" or "constant voltage surface" refers to a surface contour along which at every possible point of location for the sensing coil, the same induced voltage is developed in the sensing coil. In practice, the constant signal surface will be a small planar region located near the LNP with the sensing coil at a fixed orientation (as defined above).

As used herein, "delta coil" refers to a magnetic assembly for generating a vector gradient field (as defined above) within the navigational domain. As will become more apparent hereinafter, the delta coil will typically be described in the context of delta coil pairs including a long delta coil and a short delta coil, each pair generating vector gradient fields with the substantially zero component in the same-axial dimension but whose magnetic field patterns in the remaining components are independent of each other. Each of the long and short delta coils may be considered to generate a family of constant signal or constant voltage surfaces for the sensing coil within the navigational domain. Although the delta coils are preferably implemented with an array of appropriately designed magnetic coils (discussed below), this preferred implementation should not serve as a limitation of the present invention as it should be apparent to those skilled in the art that other magnetic configurations may be used to adequately generate the vector gradient fields.

As used herein, "magnetic look-up-table" (alternatively referenced as "the LUT") refers to a database including the magnetic field amplitude values at every x-y-z coordinate position within the navigational domain for the unidirectional coils and for each delta coil used by the present invention. Accordingly, input data consisting of an x-y-z coordinate and a magnetic field amplitude identifier, which designates a selected magnetic coil assembly, is indexed within the database to a corresponding set of magnetic field amplitude values constituting the output data. For the x-y-z coordinate system, the output data is represented by the magnetic field amplitude variables $H_x^n H_y^n H_z^n$ where the subscript x-y-z indicates the axial dimension along which the magnetic field amplitude value is being reported and the superscript is the identifier for a selected magnetic coil assembly acting as the source. The database is created through a computational analysis of the magnetic field amplitude patterns generated by the magnetic coil configurations used herein. The mathematical model to develop the necessary formulae defining the field patterns may be developed, for example, from near field electromagnetic theory. An instructive text for facilitating such an analysis is "Field and Wave Electromagnetics" 2nd edition Addison Wesley (1989) by D. K. Cheng, herein incorporated by reference. The database may be stored in any type of facility including, inter alia, read-only memory, firmware, optical storage, or other types of computer storage. Additionally, the database information may be organized into any type of format such as a spreadsheet. It should be apparent to those skilled in the art that any suitable technique may be used to ascertain or record the magnetic field values for the magnetic coil assemblies used herein.

In the coordinate system for describing the present invention, the z-axis coincides with the longitudinal dimension extending from the patient's head to foot. The x-axis coincides with a lateral dimension across the patient's body, and the y-axis is perpendicular to the planar top of the pallet or examination deck. These dimensions are identified as the patient is disposed in the recumbent position on the pallet.

Assembly for Implementing Location and Compensation Methods

Magnetic Assembly for Determining Angular Orientation of Sensing Coil

Figure 3:
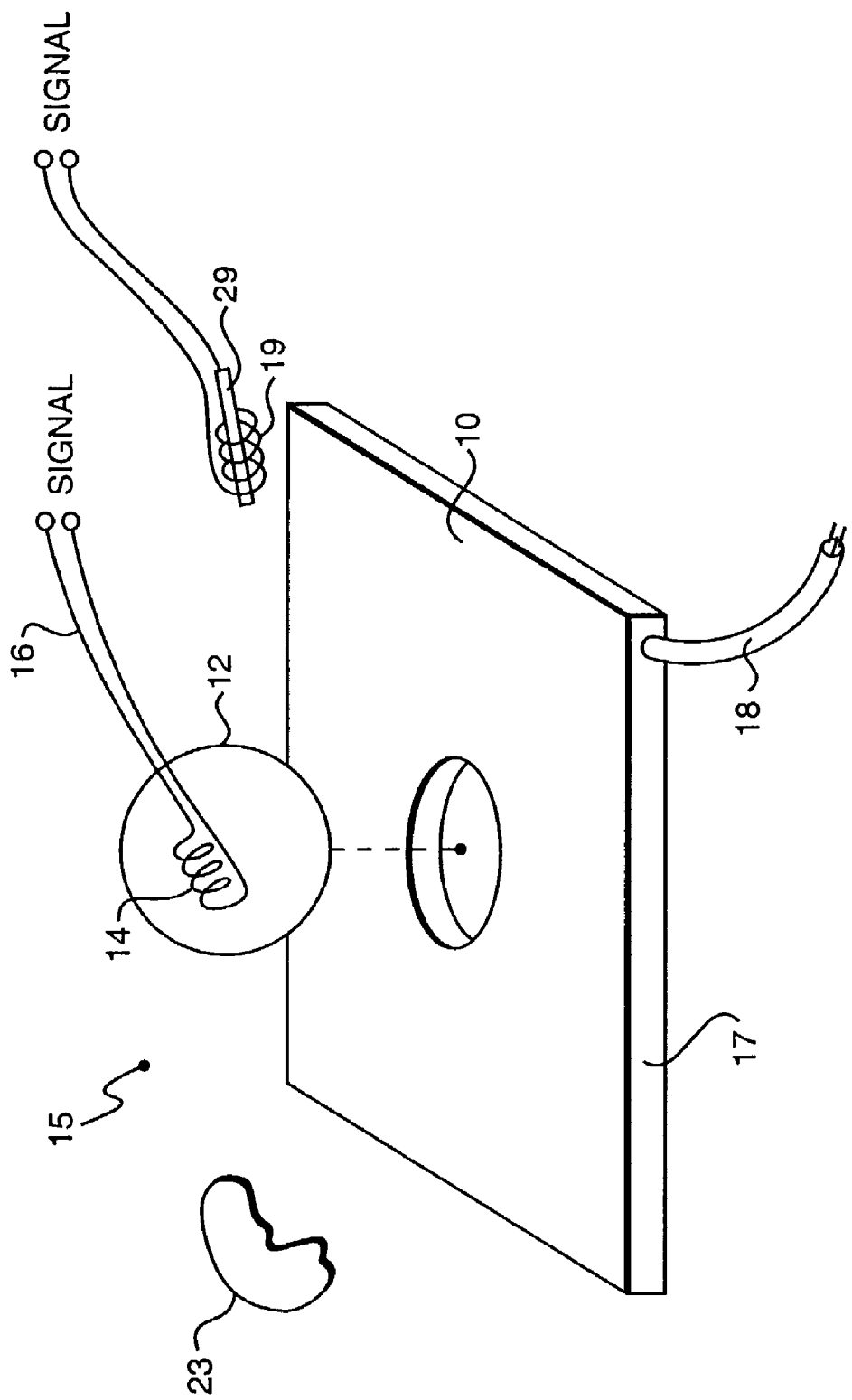
FIG. 3 is a perspective view of an examination deck used for implementing the location and compensation methods according to the present invention.

FIG. 3 schematically illustrates a perspective view of examination deck 17 that facilitates implementation of the location and compensation methods in accordance with all preferred embodiments of the present invention. Examination deck 17 employs a magnetic coil assembly arranged in a flat configuration. Examination deck 17 includes planar top platform 10 suitable for accommodating a recumbent patient disposed lengthwise. Navigational domain is illustratively depicted as the spherical volume enclosing sensing coil 14. Tool coil 19 is located in peripheral domain 15. Sensing coil 14 is attached via connection means 16 to an external signal detection apparatus (not shown). Tool coil 19 is likewise attached to an external signal detection apparatus. Although sensing coil 14 functions optimally within navigational domain 12, tool coil 19 may lie within peripheral domain 15 or navigational domain 12. The coil sets embedded in platform 10 (and described in connection with FIGS. 4-7) are activated by a signal drive unit (not shown) connected via line 18. Examination deck 17 is preferably constructed from a suitable magnetically-permeable material to facilitate magnetic coupling between the embedded coil sets and the overlying sensing coil.

First conducting body 23 and second conducting body 31 are shown in FIG. 3 in peripheral domain 15. However, both first conducting body 23 and second conducting body 31 can lie within navigational domain 12 as well in accordance with a preferred embodiment of the present invention. First conducting body 23 and second conducting body 31 respond to the fields generated by the field coils by developing eddy currents. These eddy currents, in turn, generate new fields that can influence the measured voltage across sensor coil 14 as is discussed in more detail below.

Ferromagnetic body 29 is shown in peripheral domain 15 and is shown enveloped within tool coil 19. Again, ferromagnetic body 29 and tool coil 19 can lie within navigational domain 12 as well in accordance with a preferred embodiment of the present invention. Ferromagnetic body 29 responds to the fields generated by the field coils by both focusing the magnetic flux lines and by introducing a phase shifted field. The focusing and phase shifting effect of ferromagnetic body 29 can influence the voltage drop as measured across sensor coil 14 as is discussed in more detail below.

Coil Sets for Generating x-Directed, y-Directed, and z-Directed Fields

Figure 4:
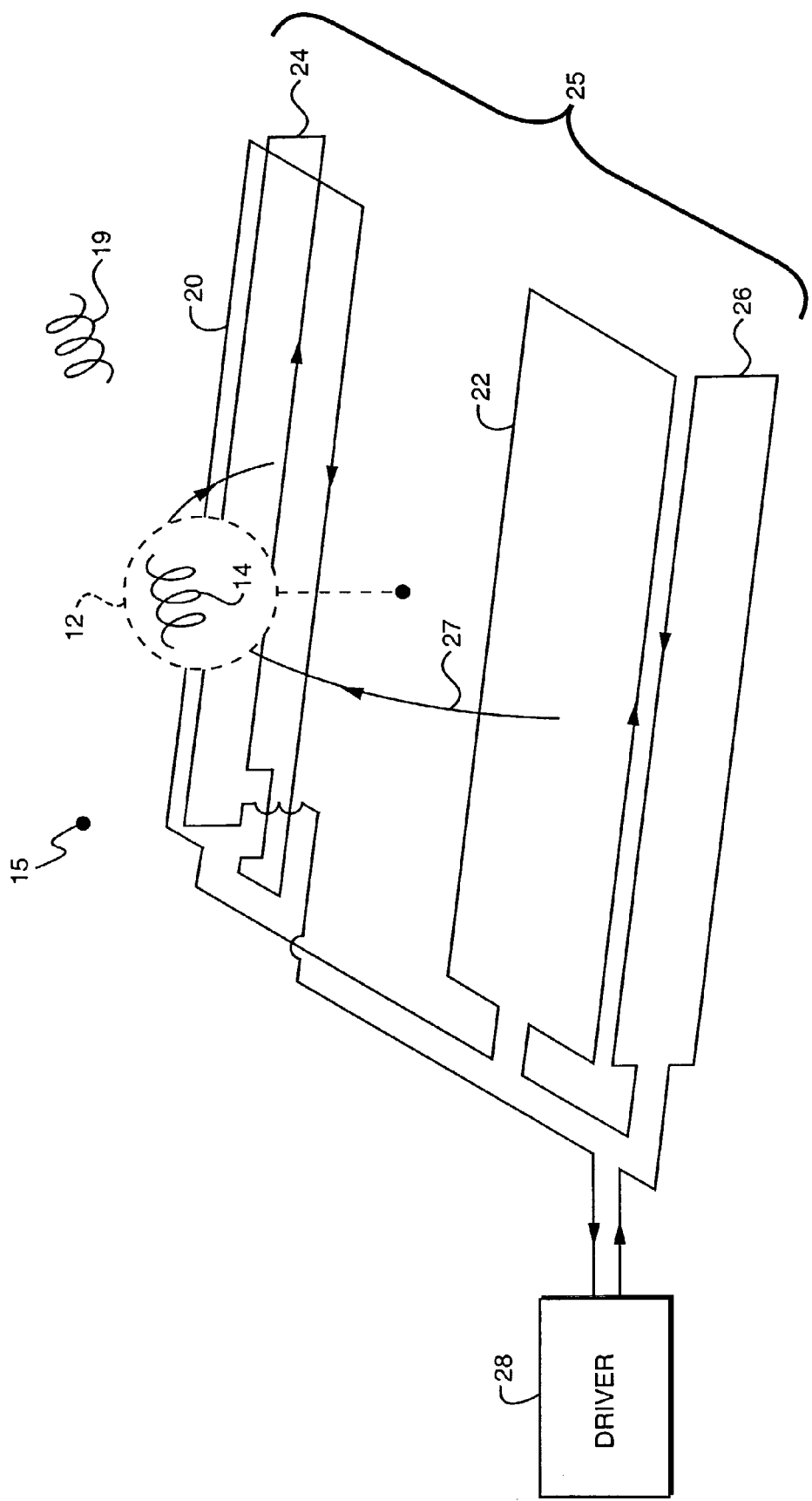
FIG. 4 shows a schematic representation of a unidirectional coil set for generating uniform x-directed fields in the navigational domain.
Figure 5:
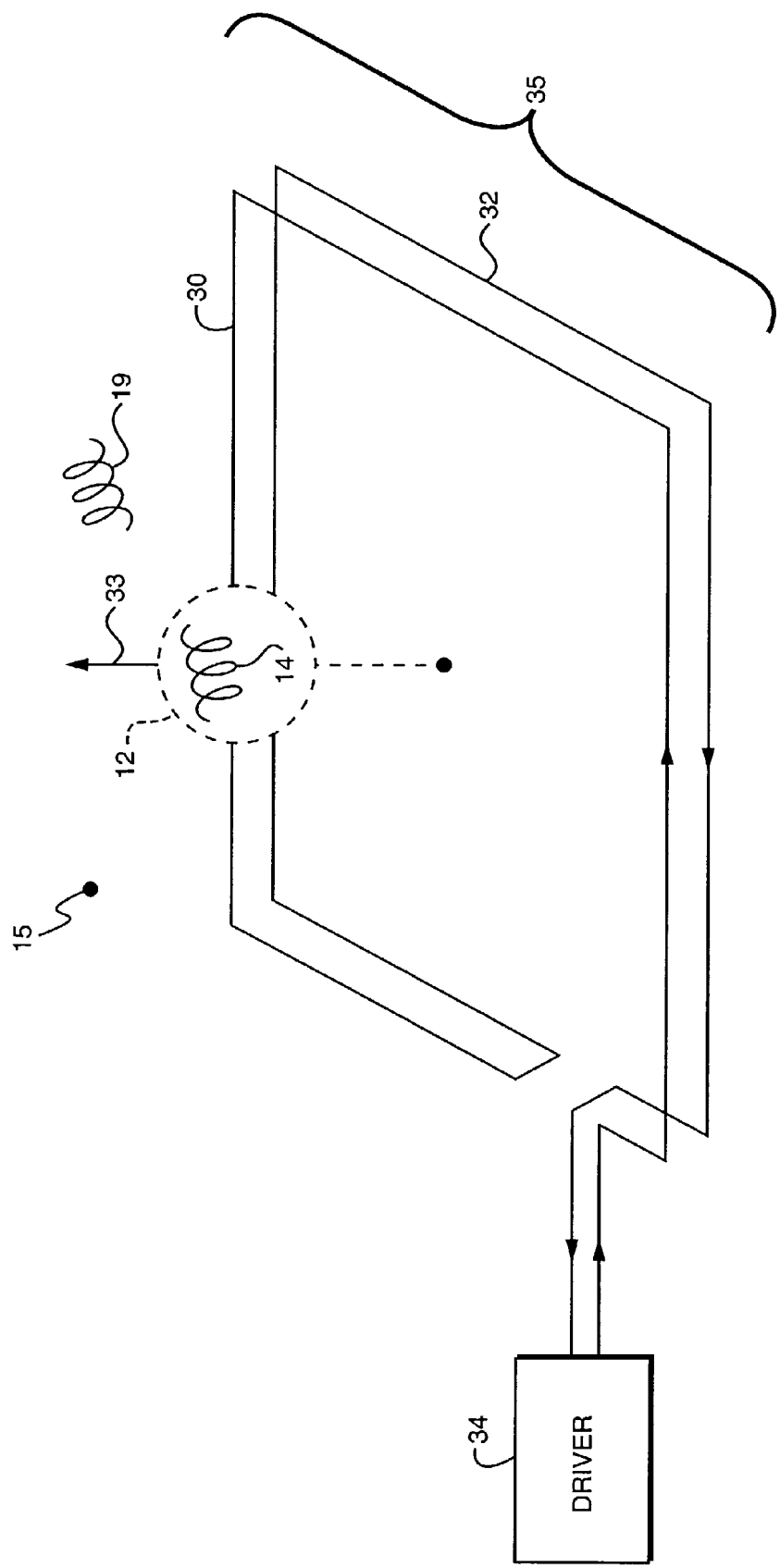
FIG. 5 shows a schematic representation of a unidirectional coil set for generating uniform y-directed fields in the navigational domain.
Figure 6:
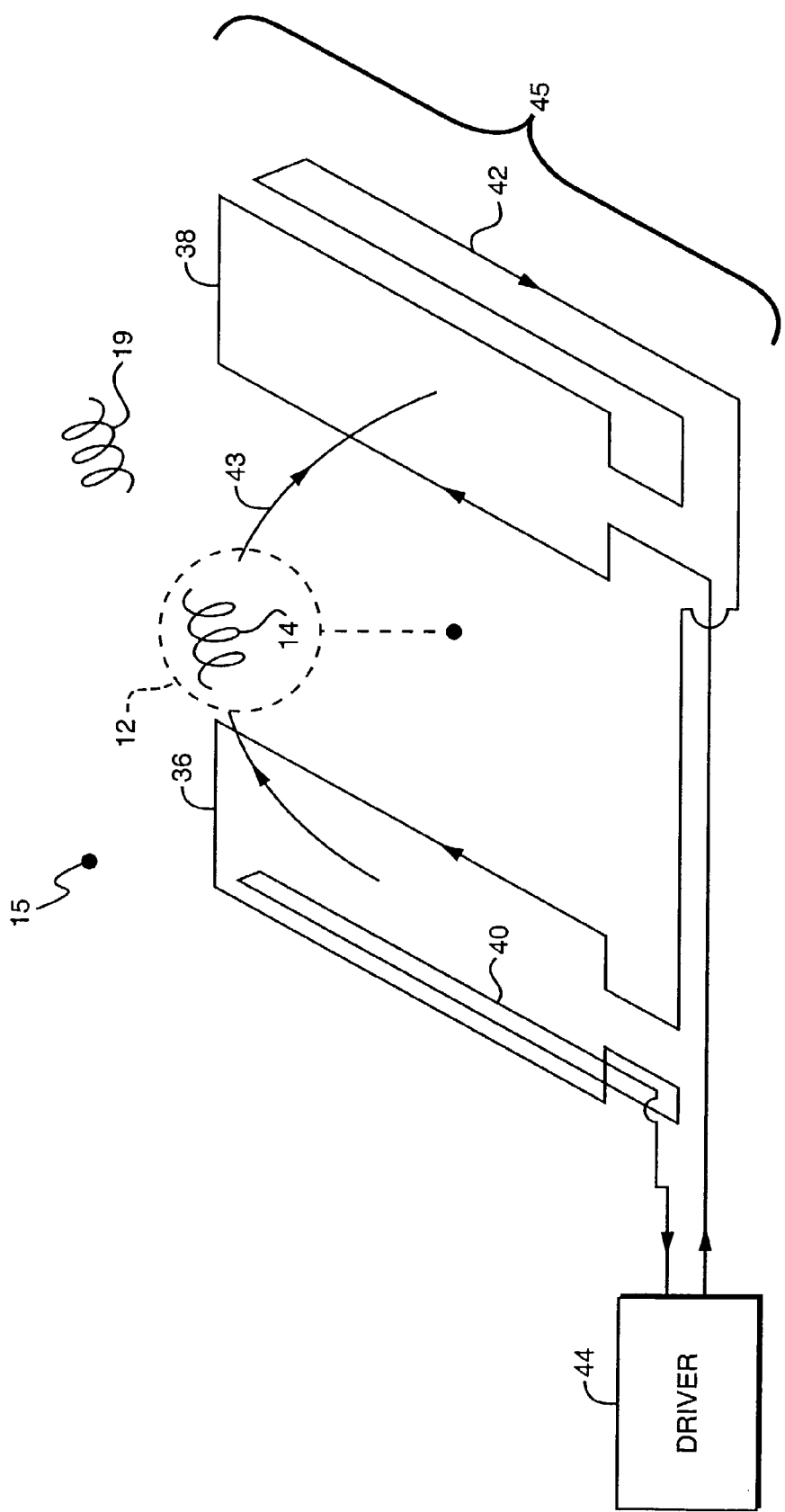
FIG. 6 shows a schematic representation of a unidirectional coil set for generating uniform z-directed fields in the navigational domain.

FIGS. 4-6 schematically illustrate unidirectional coil sets for generating substantially uniform amplitude x-directed, y-directed and z-directed fields, respectively, throughout navigational domain 12. The uniform amplitude field in one embodiment of the present invention can be operated at multiple waveforms, for example, a sinusoidal waveform with angular frequency $\omega_1$ and a sinusoidal waveform with angular frequency $\omega_2$ are two different waveforms.

Unidirectional coil set 25 of FIG. 4 includes a first coil pair with elements 20 and 24 and a second coil pair with elements 22 and 26, where the current flow as supplied by drive unit 28 is indicated by the arrow symbol. Coil elements 20 and 22 are disposed in the major surface of platform 10, while elements 24 and 26 are disposed in the lateral walls of platform 10. Elements 24 and 26 are preferably used as compensation coils to substantially cancel undesirable field components generated by elements 20 and 22 in the y and z directions. The coils cumulatively generate a substantially uniform amplitude x-directed field as indicated by representative field line 27.

Unidirectional coil set 35 of FIG. 5 schematically illustrates a coil set for generating a substantially uniform amplitude y-directed field throughout navigational domain 12 as indicated by representative field line 33. The coil set includes a coil pair with elements 30 and 32 disposed in spaced-apart and parallel relationship within platform 10, with the indicated current flow as supplied by drive unit 34.

Unidirectional coil set 45 of FIG. 6 generates a substantially uniform amplitude z-directed field as indicated by representative field line 43. Coil set 45 includes a first coil pair with elements 38 and 42 and a second coil pair with elements 36 and 40, where the current flow as supplied by drive unit 44 is indicated by the arrow symbol. Coil elements 36 and 38 are disposed in the major surface of platform 10, while elements 40 and 42 are disposed in the lateral walls of platform 10. Elements 40 and 42 are preferably used as compensation coils to substantially cancel undesirable field components generated by elements 36 and 38 in the y direction.

Unidirectional coil sets 25, 35, and 45 are illustrative only and should not be construed as a limitation of the present invention. It should be apparent to those skilled in the art that other coil configurations are possible within the scope of the present invention provided such other configurations produce the desired magnetic field patterns in navigational domain 12 at the desired frequency. A first connection means (not shown) couples sensing coil 14 to a signal measuring device, and a second connection means (also not shown) couples tool coil 19 to a signal measuring device.

Coil Sets for Generating Vector Gradient Fields

Figure 7:
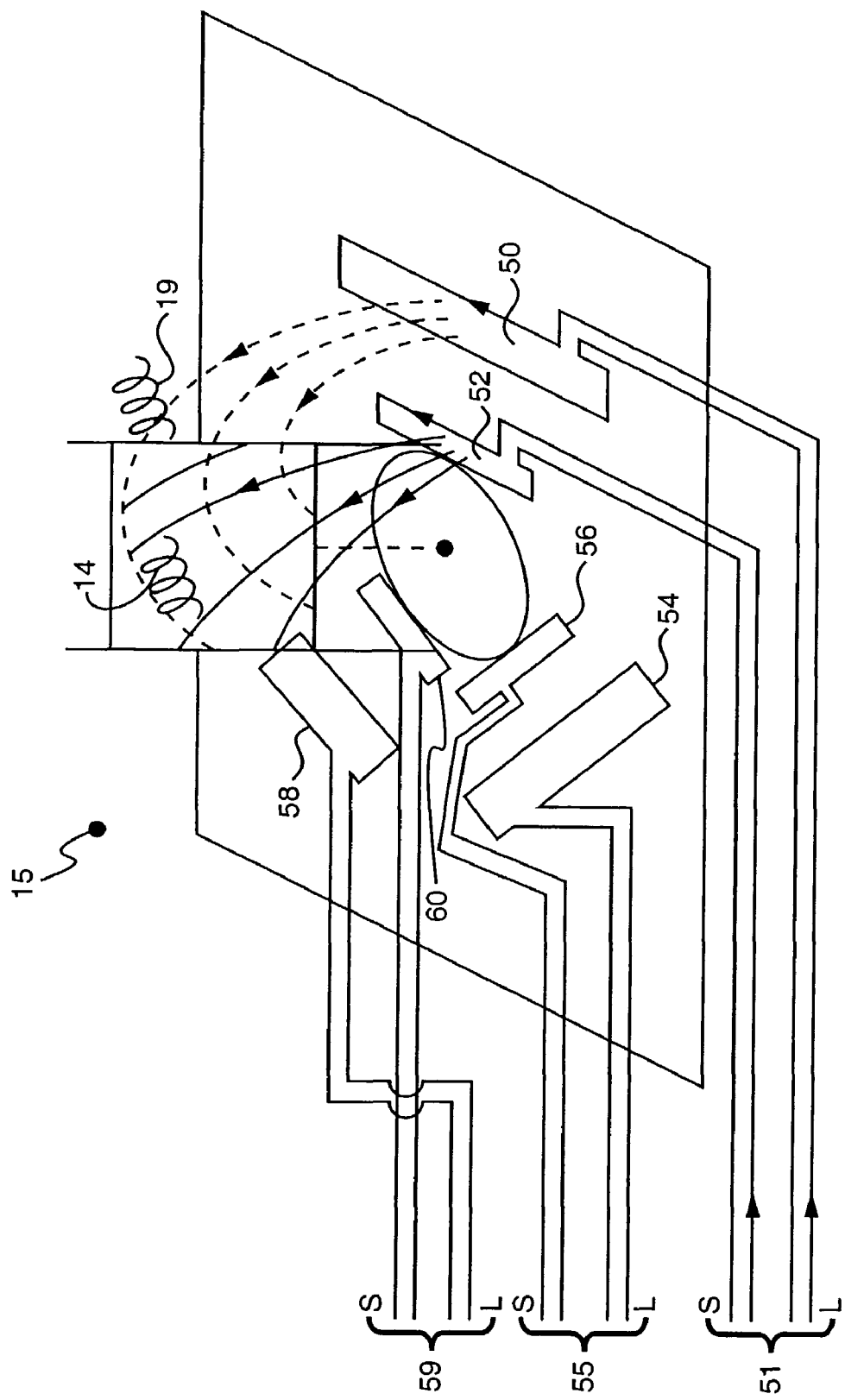
FIG. 7 shows a schematic representation of a coil configuration for generating vector gradient fields in the navigational domain.
Figure 8:
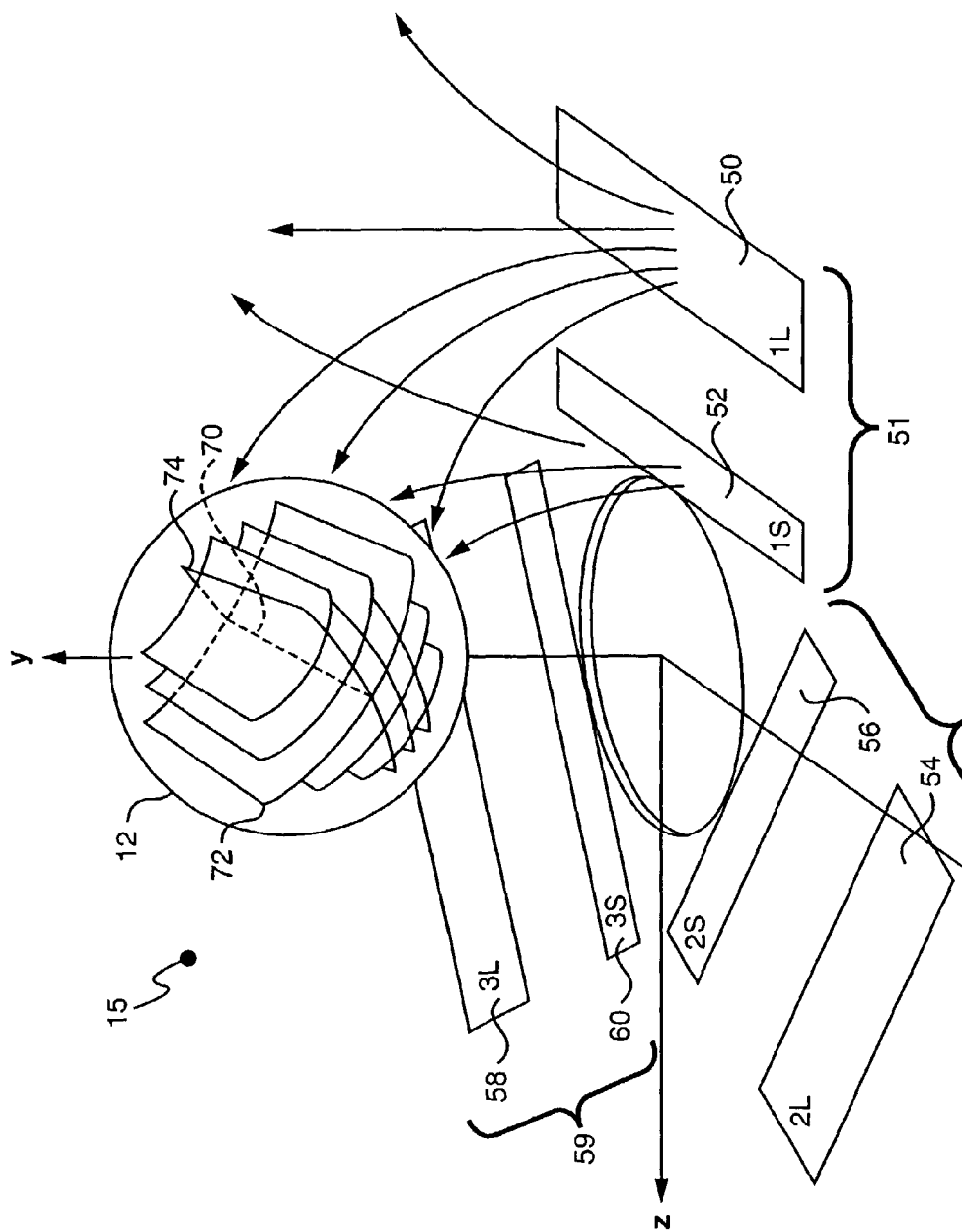
FIG. 8 shows a schematic representation of the coil configuration of FIG. 7, including constant signal surfaces generated by those coils.

FIGS. 7 and 8 show a coil configuration that can be used to determine the positional coordinates of sensing coil 14 in accordance with all of the preferred embodiments of the present invention. The configuration includes six coils grouped into three pairs of long and short delta coils (50 and 52, 54 and 56, 58 and 60). The delta coils are mutually coplanar and are disposed in the planar top of the examination deck immediately beneath the recumbent patient. Interconnection means between delta coil group 51, delta coil group 55, delta coil group 59 and a signal drive unit (not shown) is indicated.

The coils are preferably arranged in a circular orientation about the y-axis such that there is an axis perpendicular to the direction of elongation of the coils, proceeding from the long coil set to the short coil set, where that axis is at 0°, 120° and 240° to the z-axis. By way of reference, the x-axis is considered to be oriented at 270° with respect to the z-axis in the x-z plane. The magnetic field generated by delta coil group 51 is shown representatively by the field lines extending from the upper region of the coils. In one embodiment of the present invention, the resulting vector gradient field can be operated at multiple waveforms. For example, a sinusoidal waveform with angular frequency $\omega_1$ and a sinusoidal waveform with angular frequency $\omega_2$ are two different waveforms. The field lines from delta coil group 51 form the family of constant signal surfaces shown in FIG. 8 within the navigational domain 12. Superposition of the constant signal surfaces generated by long coil set 50 and short coil set 52 produce the bounded regions indicated in FIG. 8. The intersection of two such constant signal surfaces generated by short coil set 52 and long coil set 50 is line 70.

Figure 9:
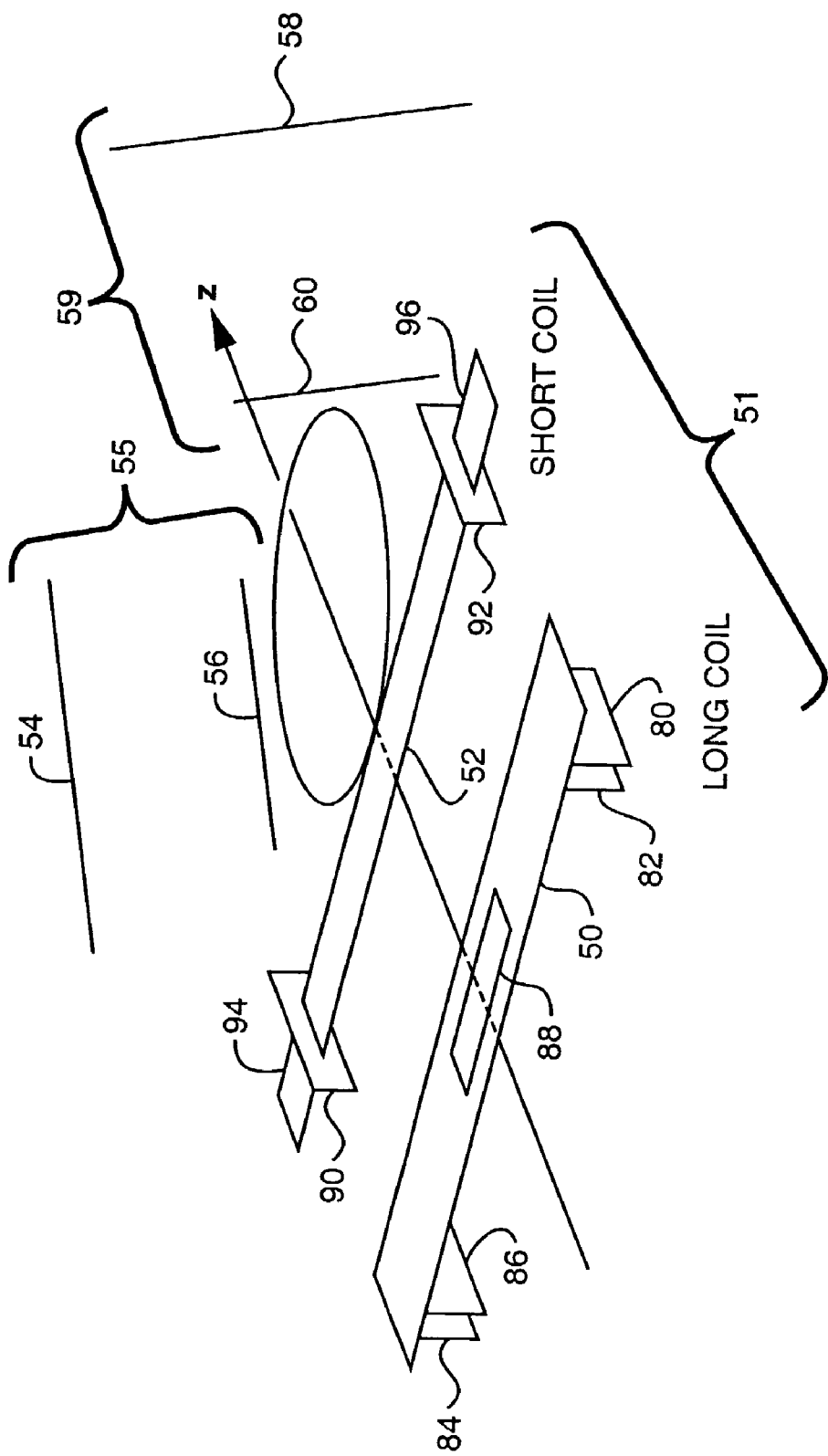
FIG. 9 shows an upper plan schematic view of a delta coil group from FIG. 7 relative to an inner circular space representing the projection of navigational domain into the plane of the delta coils.

FIG. 9 shows an upper plan schematic view of delta coil group 51 relative to an inner circular space representing the projection of navigational domain 12 into the plane of the delta coils. This design creates a high spatial gradience in two of the axis dimensions and a substantially zero field value in the remaining axial dimension. This particular design is accomplished by modifying the termination points of the coils with compensation coils such that the modified coil is effectively operative as an infinitely long coil. Long coil sets 50, 54, and 58 are further compensated by central "sucker" coils, indicated in FIG. 9 for long coil set 50 as central "sucker" coil 88. Accordingly, each of the long coils and short coils is modified by representative compensation coils 80 and 82, 84 and 86, 88, 90 and 94, and 92 and 96 respectively, disposed at the indicated endpoints and center of the corresponding delta coil. The long coil and short coil configurations are shown schematically for only delta coil group 51, but similar configurations likewise exist for delta coil group 55 and delta coil group 59, shown representatively as the indicated lines.

Parameters related to the quality of the coils, such as (i) the degree of uniformity of the uniform amplitude field coils and (ii) how close to zero the vector gradient field is in the non-gradient direction for the delta coils, determine the size of navigational domain 12 and peripheral domain 15.

Tool Coil System for Ferromagnetic and Conductor Compensation

Figure 10:
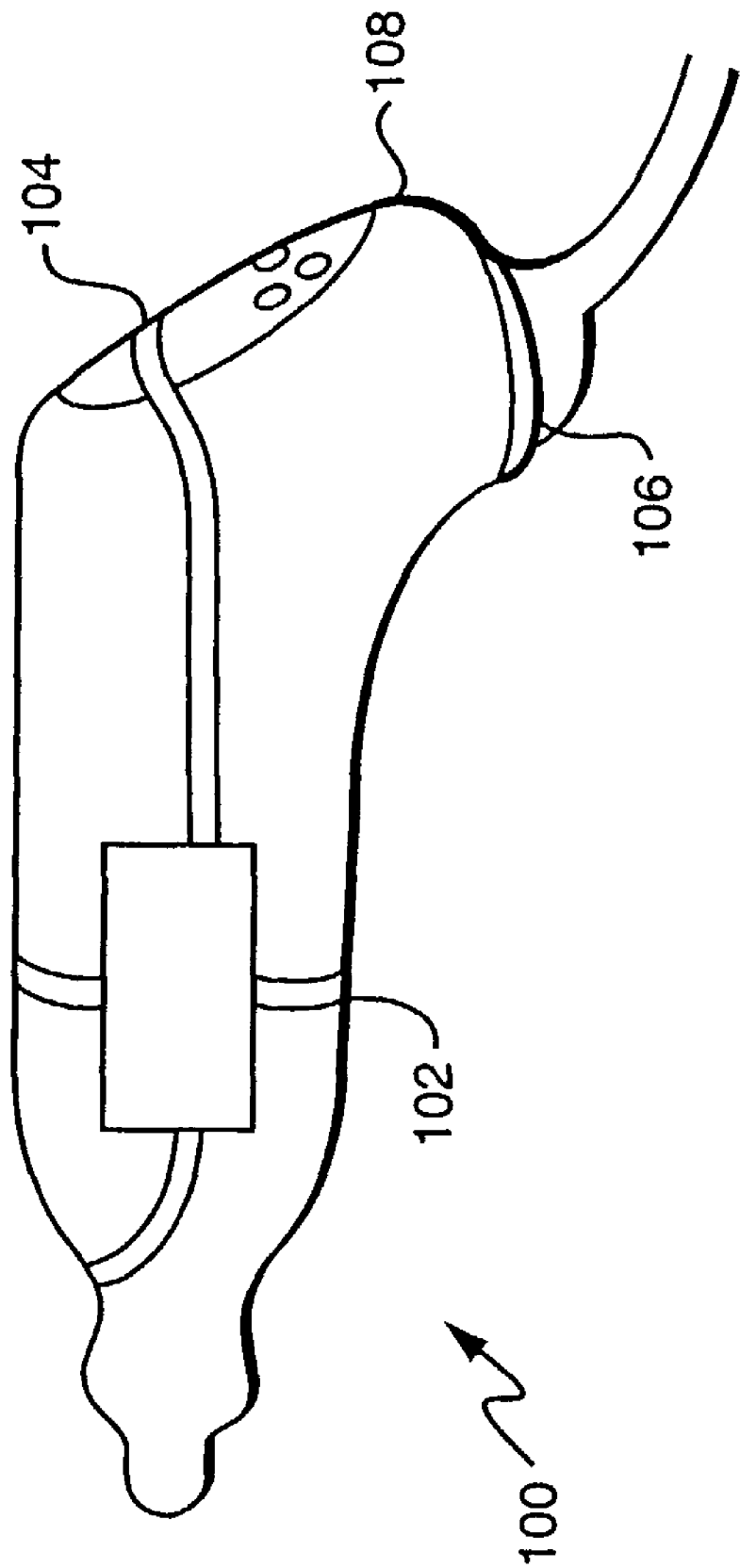
FIG. 10 depicts an example of a tool coil attached to a surgical tool used to drill holes in the vertebrae of a patient, as well as an exemplary hysteresis graph of such a ferromagnetic tool.

FIG. 10 indicates tool coil 19 affixed to surgical tool 108, where surgical tool 108 is a ferromagnetic and conducting object. Also shown is exemplary hysteresis graph 100 of surgical tool 108. Hysteresis graph 100 illustrates the nonlinear behavior of a magnetic field H associated with surgical tool 108 in response to an applied magnetic field B. Such a response is typical of ferromagnetic objects.

Figure 11:
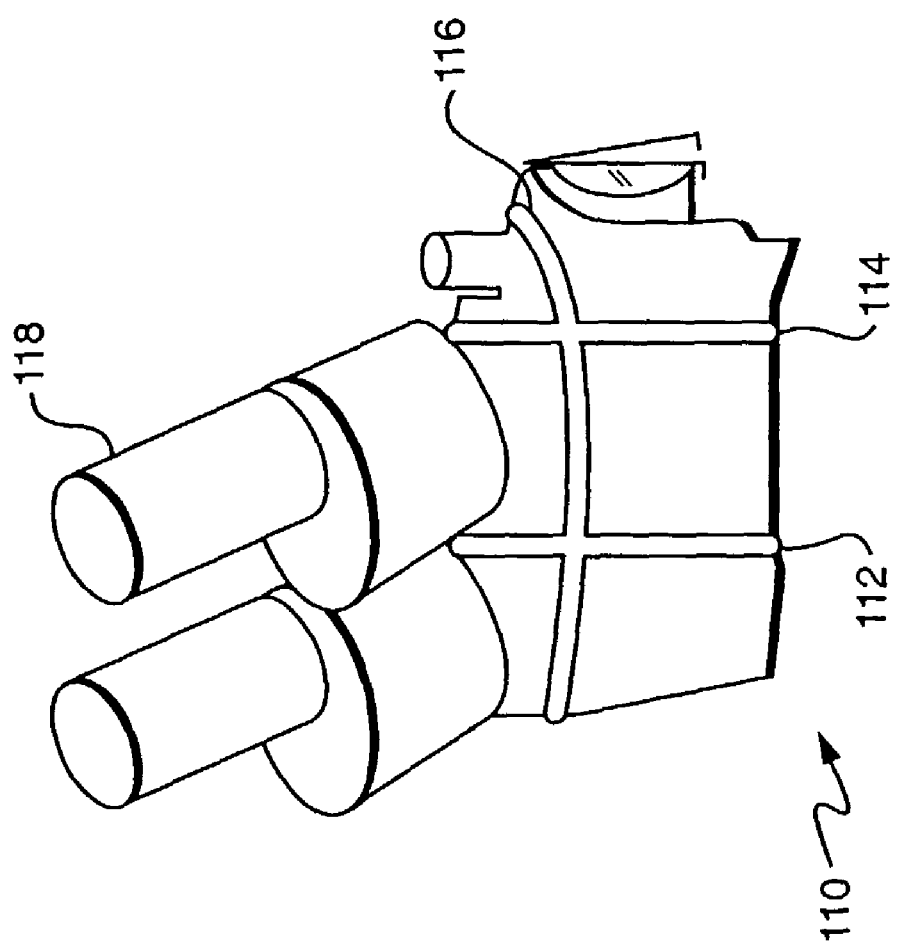
FIG. 11 depicts an example of the use of the surgical tool of FIG. 10 with an attached tool coil.

FIG. 11 indicates how surgical tool 108 and tool coil 19 of FIG. 10 may be used in practice. Surgical tool 108 is used to drill holes into vertebrae 110.

Shield Device

Figure 12:
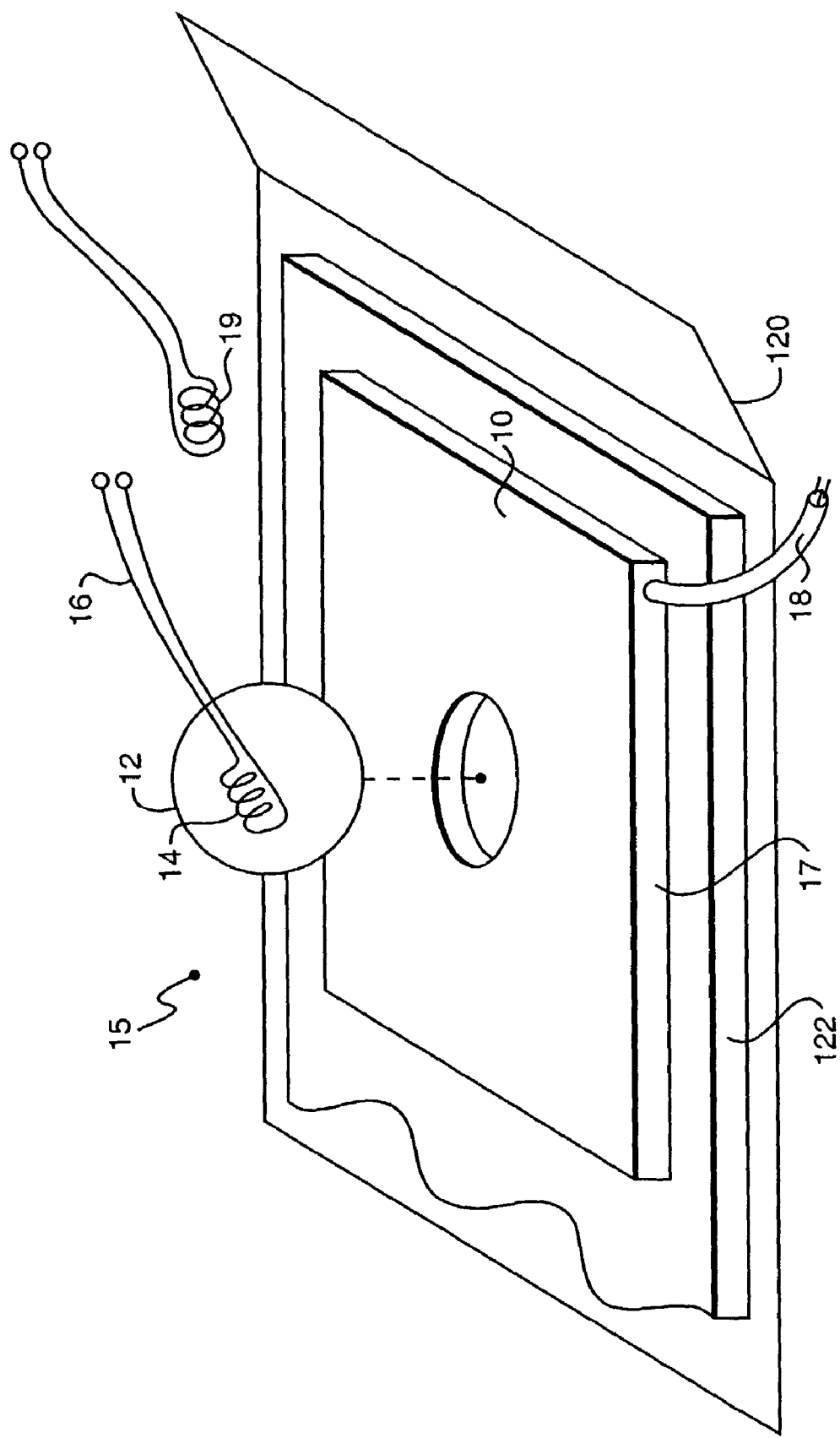
FIG. 12 illustrates a perspective view of an examination deck suitable for implementing the location and compensation methods in the presence of a shield device, according to the present invention.

FIG. 12 schematically illustrates a perspective view of examination deck 17 that facilitates implementation of the location and compensation algorithms in accordance with shield device 120. Examination deck 17 includes planar top platform 10 suitable for accommodating a recumbent patient disposed lengthwise. Examination deck 17 rests on base 122. Navigational domain 12 is illustratively depicted as the spherical volume enclosing a sensing coil 14 attached via connection means 16 to an external signal detection apparatus (not shown). The coil sets embedded in platform 10 (and described in connection with FIGS. 4-7) are activated by a signal drive unit (not shown) connected via line 18. The examination deck is preferably constructed from a suitable magnetically permeable material to facilitate magnetic coupling between the embedded coil sets and the overlying sensing coil. Shield device 120 can be made from aluminum, copper or virtually any other conductive material. It is also possible to use materials other than a conductive sheet such as a mesh or strips of material. A further possibility is to use a plastic of polymer film with a conductive coating.

Overview of Compensation Methods

System and Method for Extraneous Eddy Current Compensation

Figure 13:
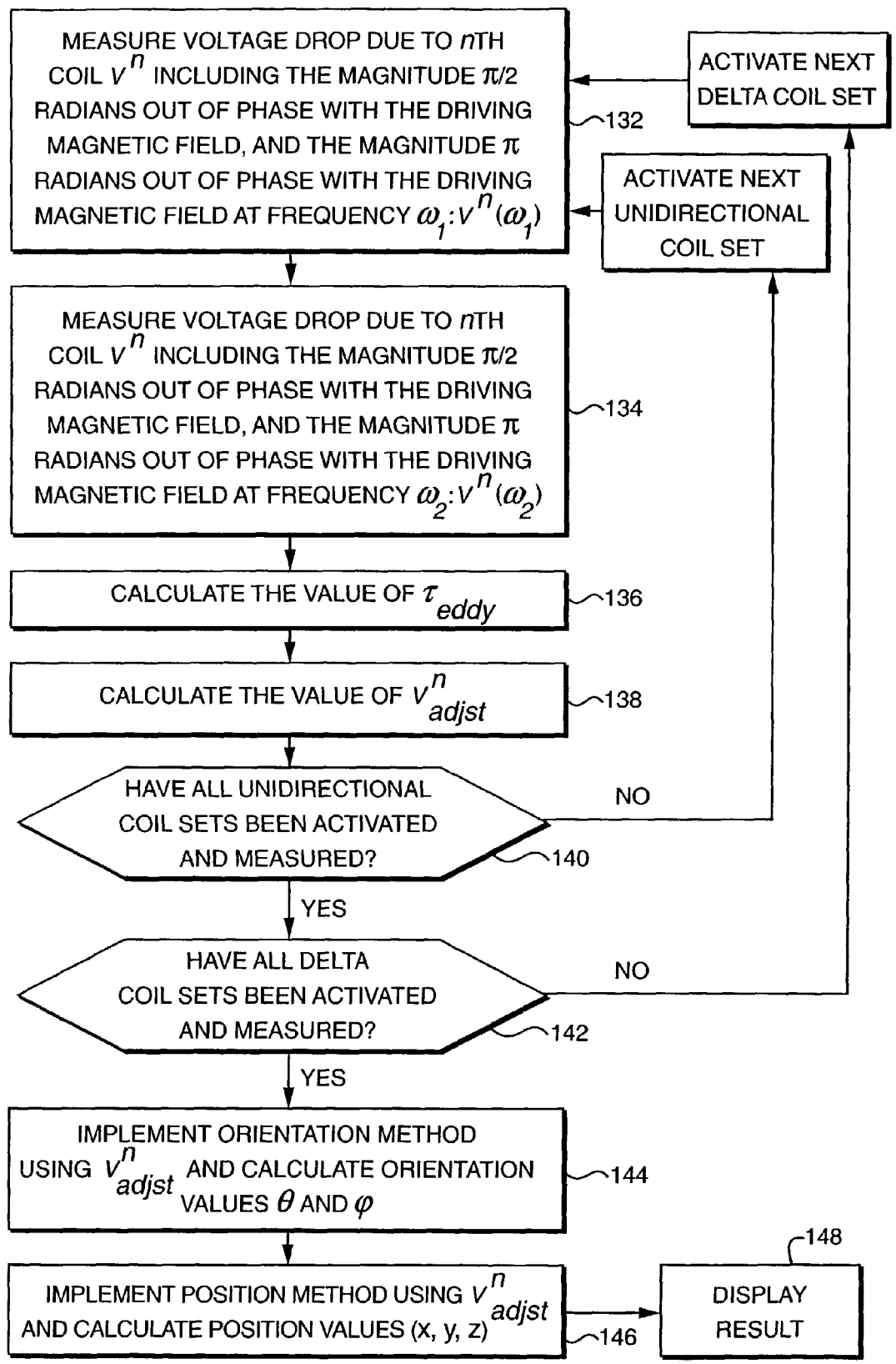
FIG. 13 shows a flow diagram for a method of eddy current compensation in accordance with the present invention.

FIG. 13 indicates a schematic of a method for eddy current compensation consistent with the present invention. Measuring steps 132 and 134 involve activating each of nine coil sets and measuring the field at sensing coil 14 at different waveforms. For example, a sinusoidal waveform with angular frequency $\omega_1$ and a sinusoidal waveform with angular frequency $\omega_2$ correspond to two different waveforms.

The nine coil sets correspond to three unidirectional coil sets and three delta coil groups, where each delta coil group contains a long coil set and a short coil set. The unidirectional coil sets-generate uniform amplitude fields in the x, y, and z-directions and are depicted in FIGS. 4, 5, and 6. From FIG. 7, delta coil group 25 includes short coil set 52 at 0° (denoted by n=1(s)) and a long coil set 54 at 0° (denoted by n=2(L)); delta coil group 55 includes short coil set 56 at 120° denoted by n=2(s)) and long coil set 54 at 120° (denoted by n=2(L)); and delta coil group 59 includes—short coil set 60 at 240° (denoted by n=3(s)) and long coil set 58 at 240° (denoted by n=3(L)). The angular designations associated with the delta coil groups indicate the angle with respect to the z-axis of the coil dimension that is perpendicular to the direction of elongation of the delta coils as in FIG. 7. Accordingly, the three delta coil groups are arranged pair-wise in a circular orientation about the y-axis at angles of 0°, 120°, and 240°.

As described above, a series of fields are generated and measured in sensing coil 14 at a first waveform (measuring step 132) and at an mth waveform (measuring step 134). For example, considering two waveforms where the waveforms correspond to substantially uniform amplitude fields with sinusoidal waveforms and angular frequencies $\omega_1$ and $\omega_2$ and considering x-directed fields of coil set 25 of FIG. 4 with measured values of $$V^x(\omega_1), V^x(\omega_2)$$

in sensing coil 14, the value of a constant $\tau_{eddy}$ defined by:

$$\tau_{eddy} = \frac{\text{Re}\left\{\frac{V^x(\omega_2)}{\omega_2} - \frac{V^x(\omega_1)}{\omega_1}\right\}}{\text{Im}\{V^x(\omega_1) - V^x(\omega_2)\}}$$

is calculated where "Re" indicates the real part (0 radians phase shifted part), and "Im" indicates the imaginary part ($\pi/2$ radians phase shifted part) of the terms enclosed in the brackets. This corresponds to a portion of calculation step 138 of FIG. 13 in one embodiment of the present invention and will be discussed in more detail below.

Finally, an adjusted value for the potential drop $$V^x_{adjst}$$

is calculated using $\tau_{eddy}$. Again, using the above example of substantially uniform amplitude fields with sinusoidal waveforms and angular frequencies $\omega_1$ and $\omega_2$, the value of $$V^x_{adjst}$$

is:

$$V^x_{adjst} = \text{Re}\{V^x\} + \omega\tau_{eddy}\text{Im}\{V^x\}.$$

This completes calculation step 138 of FIG. 13 in one embodiment of the present invention. Again, this will be discussed in more detail below.

In another embodiment of the present invention, measurements are performed at four different waveforms (measuring steps 132 and 134 in FIG. 13). For example, considering a magnetic field waveform that is sinusoidal in nature with angular frequency $\omega$, measurements at four frequencies $\omega_1$, $\omega_2$, $\omega_3$, and $\omega_4$ correspond to measuring steps 132 and 134 at four different waveforms.

Using the measured values of the real and imaginary portions of the potential drop across sensing coil 14 yields the following four equations:

$$\text{Re}\{V^n\} = V^n_{adjst} - \omega \text{Im}\{V^n\}(\tau^* + \omega\tau^{**})$$

with three unknowns: $\tau^*$, $\tau^{**}$, and $$V^n_{adjust}.$$

Thus, the value of $$V^n_{adjust}$$

can be determined using singular value decomposition as is described in more detail below. Again, this corresponds to calculation step 138 in FIG. 13 in one embodiment of the present invention.

At query step 140, it is determined whether all unidirectional field coils have been activated. In the example here, only the x-directed coils have been activated (coil set 25 of FIG. 4). Thus, a corresponding set of substantially uniform amplitude fields with different waveforms are generated and measured at sensing coil 14 in the y-direction by coil set 35 of FIG. 5, and then likewise in the z-direction by coil set 45 of FIG. 6, with the appropriate calculations.

Next, at query step 142, it is determined whether all of the delta coil sets have been activated. As above, each delta coil set is activated in succession the induced voltage is measured in sensing coil 14 at different waveforms. Again as above, the measurement of the voltage drops at the two waveforms allow for the calculation of an adjusted voltage drop across sensing coil 14. $V_{adjst}$ is the signal that would have been picked up by sensor coil 14 if the conductive body disturbance had not been present.

Figure 16:
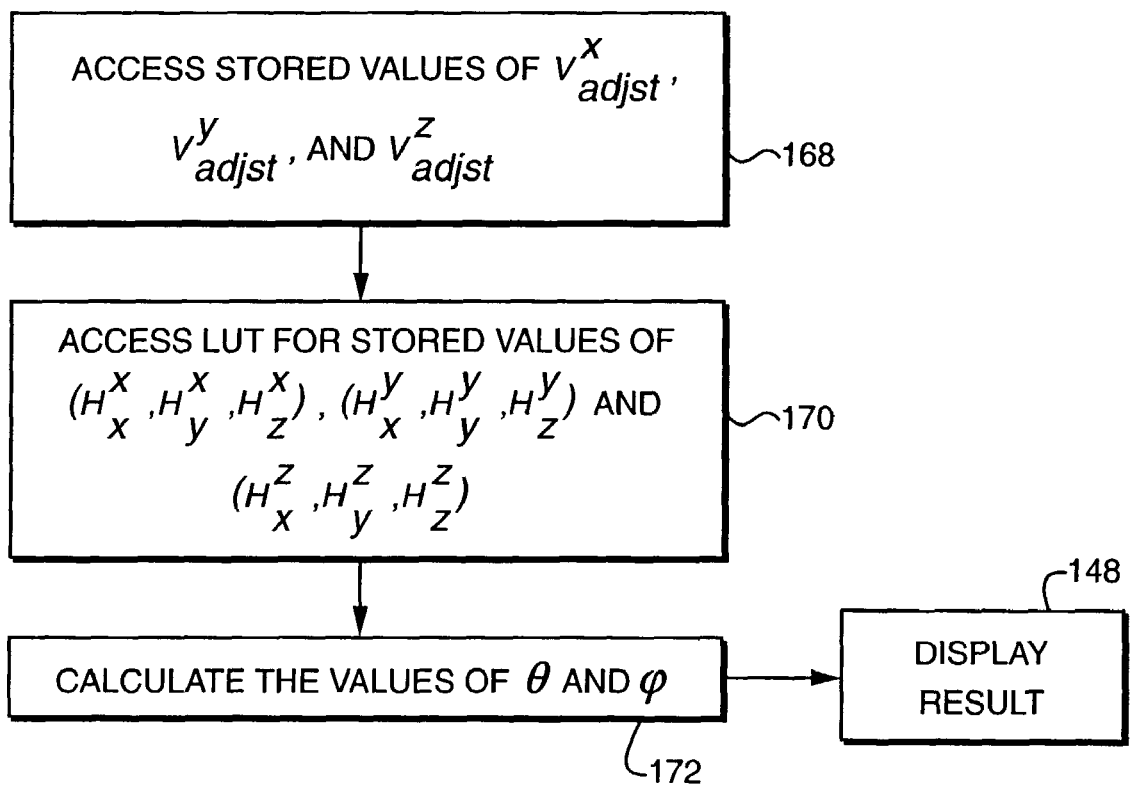
FIG. 16 shows a more detailed flow diagram for the orientation calculation step of FIG. 13.

Following the calculation of the adjusted voltage drop for all nine coils, an orientation calculation is performed in step 144 to determine the values of the sensing coil 14 orientation variables $\phi$ and $\theta$, independent of the unknown sensing coil 14 positional variables (x, y, z). A more detailed breakdown of orientation calculation 144 is shown in FIG. 16 and is discussed in more detail below.

Figure 17:
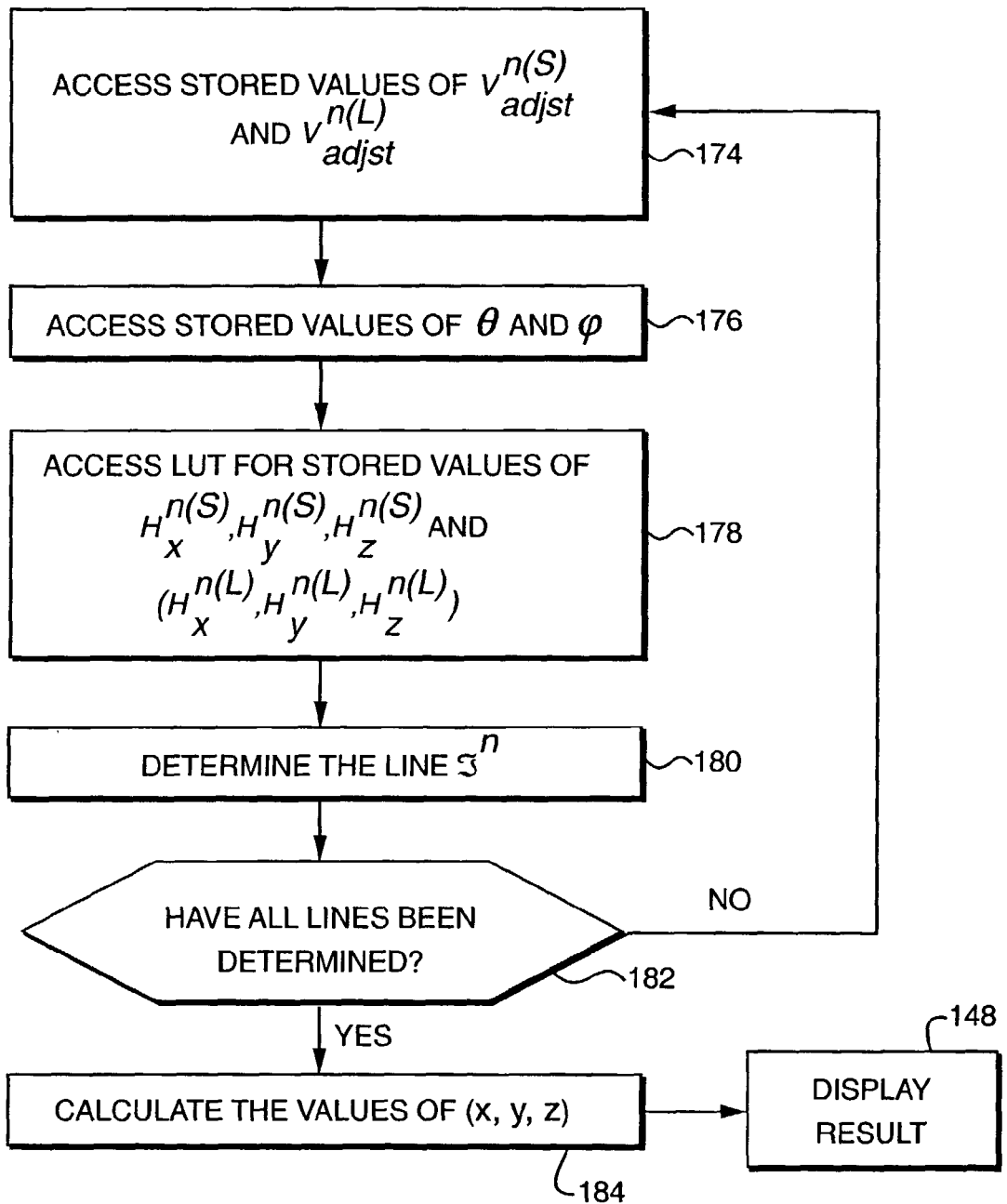
FIG. 17 shows a more detailed flow diagram for the access step of FIG. 13.

Finally, in step 146 of FIG. 13, a position calculation is performed to obtain the positional variables (x, y, z) of sensing coil 14. A more detailed breakdown of position calculation 146 is shown in FIG. 17. In FIG. 17, access step 176 indicates that orientation calculation 144 is preferably performed before positional calculation 146. Next, in access step 178, the LUT is accessed to obtain the magnetic field values at the LNP for a long delta coil set and a short delta coil set. These magnetic field values and the as-computed values for the orientation angles $\theta$ and $\phi$ are substituted into the appropriate induced voltage equations to calculate for each delta coil the value of the voltage amplitude signal induced in the sensing coil at the LNP. Based on the difference between the measured and the LNP values for the induced voltage signals, a calculation is performed in step 180 that permits identification of a line $\Im^n$ on which sensing coil 14 lies, as described in more detail below. In query step 182, it is determined whether such a line $\Im^n$ has been identified for each delta coil group. Following the identification of three lines $\Im^1$, $\Im^2$, $\Im^3$ calculation step 184 is performed to determine where in space the lines $\Im^1$, $\Im^2$, $\Im^3$ intersect. That position in space is the location (x, y, z) of sensing coil 14.

System and Method for Ferromagnetic and Conductive Object Compensation

Figure 14:
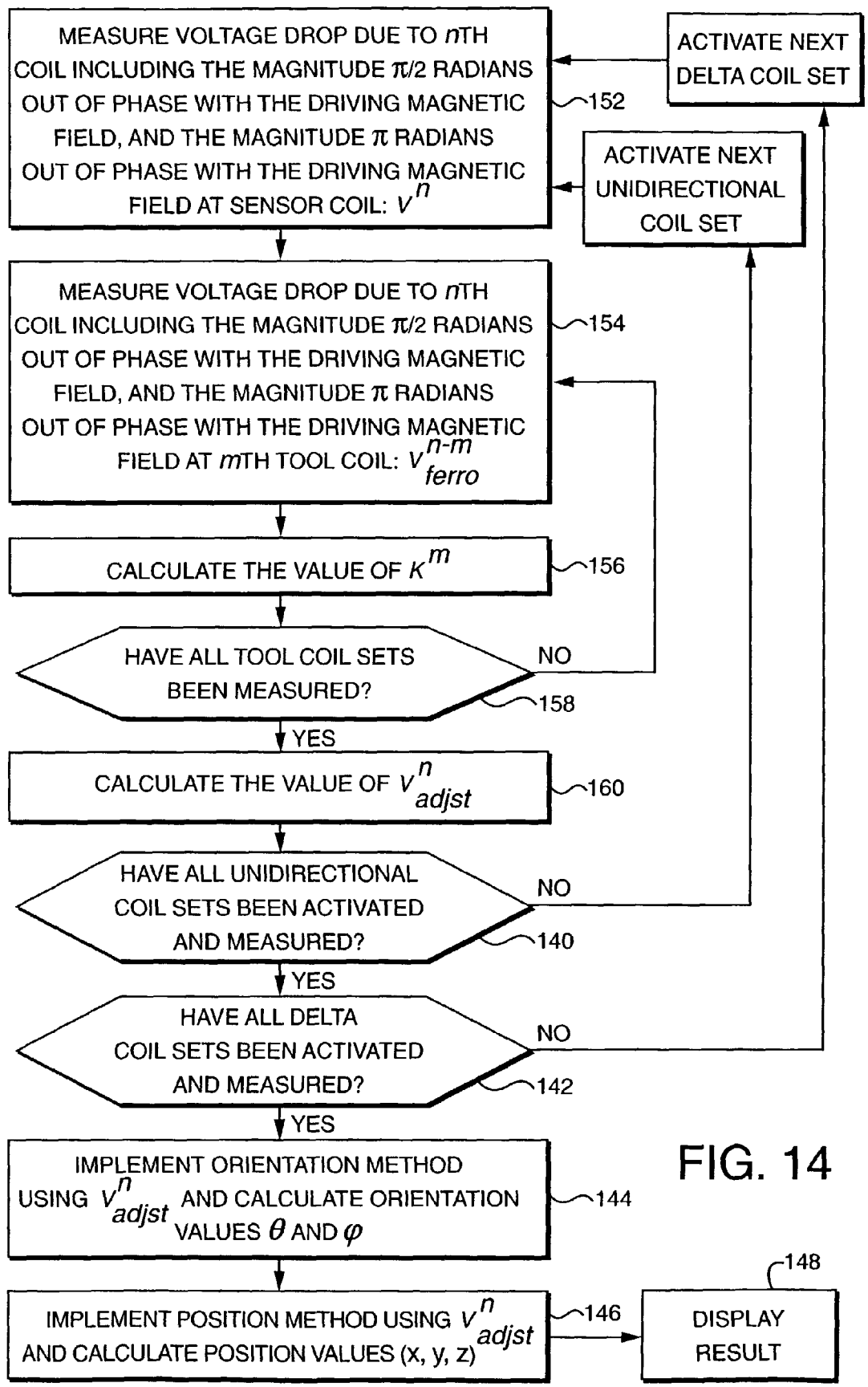
FIG. 14 shows a flow diagram for a method of ferromagnetic and conductor compensation in accordance with the present invention.

FIG. 14 indicates a schematic for ferromagnetic and conductor compensation consistent with the present invention. Measuring step 152 is similar to measuring step 132 as described above for FIG. 13. Measuring step 154 is different, however, in that a measurement is performed across tool coil 19.

As above, the nine coil sets correspond to three unidirectional coil sets and three delta coil groups, where each delta coil group contains a long coil set and a short coil set. The unidirectional coil sets generate uniform amplitude fields in the x, y, and z-directions and are depicted in FIGS. 4, 5, and 6. The delta coil sets are depicted in FIG. 7 and described above.

In particular, a series of substantially uniform amplitude fields are detected by sensing coil 14 (measuring step 152) and tool coil 19 (measuring step 154) originating from unidirectional coil set 25 of FIG. 4, unidirectional coil set 35 of FIG. 5, and unidirectional coil set 45 of FIG. 6. Also, as described in conjunction with FIG. 13, each delta coil is activated in succession and a corresponding induced voltage is measured in sensing coil 14 (measuring step 152) and tool coil 19 (measuring step 154).

Again, as discussed in more detail below, the measured voltage drops allow for the calculation of an adjusted voltage drop across sensing coil 14, the voltage that would be present if there were no disturbance. The first step, indicated in calculation step 156, is to calculate the value of a constant K where $$\text{Im}\{V^n - KV^n_{ferro}\} = 0$$

where "Im" indicates the imaginary part ($\tau/2$ radians phase shifted part) as above. In calculation step 160, the value of $$V^n_{adjst}$$

is calculated using K $$V^n_{adjst} = V^n - KV^n_{ferro}$$

This is step 160 of FIG. 14 and is described in more detail below.

The remaining steps indicated in FIG. 14 have already been discussed above in the context of FIG. 13 with the same reference numbers.

System and Method for Shield Device Compensation

Figure 15:
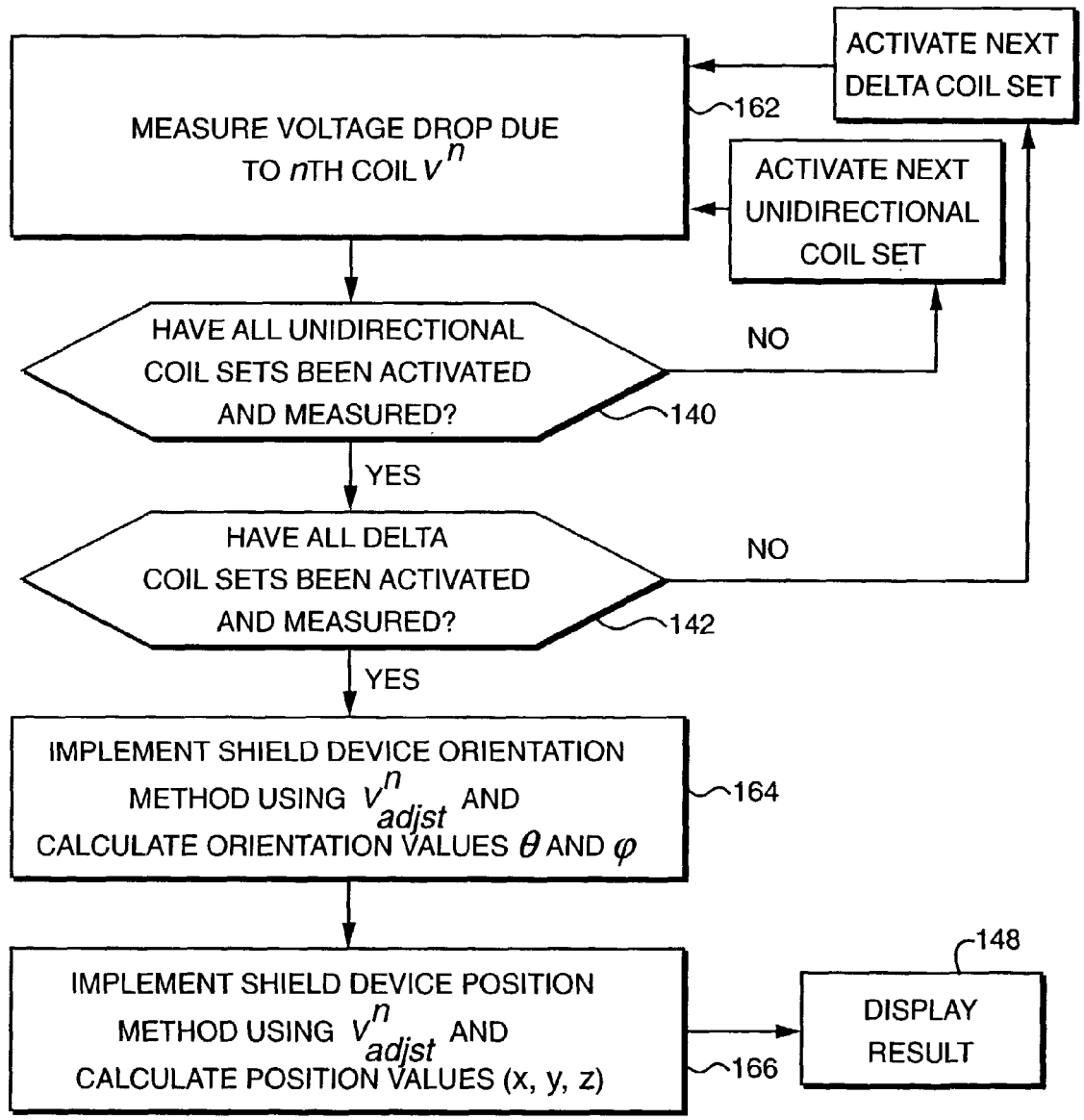
FIG. 15 shows a flow diagram for a method of shield device compensation in accordance with the present invention.
Figure 18:
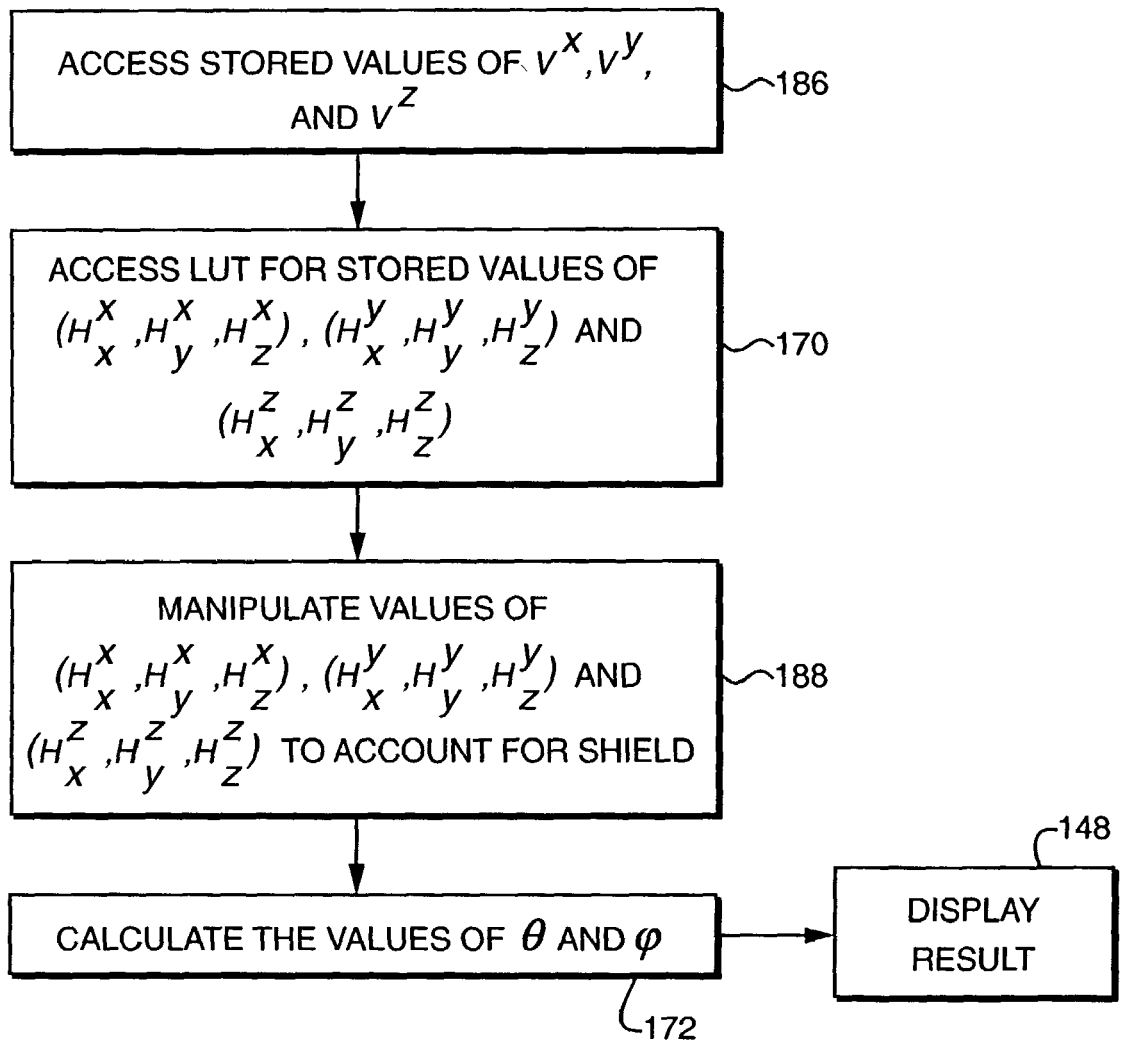
FIG. 18 shows a more detailed flow diagram for the orientation calculation step of FIG. 15.

FIG. 15 indicates a schematic of a method for shield device compensation consistent with the present invention. Again, a magnetic assembly of nine individual coil sets and shield device 120 are used to generate magnetic fields sufficient to develop a corresponding set of nine induced voltage signals at sensing coil 14. Measurement step 162 indicates such a measurement. The major difference associated with shield device compensation is observed in calculation steps 164 and 166. Rather than the standard orientation calculation step 144 of FIGS. 13 and 14, and presented in more detail in FIG. 16, orientation calculation step 164 of FIG. 15 is shown in more detail in FIG. 18. Additionally, rather than the standard position calculation step 146 of FIGS. 13 and 14, and presented in more detail in FIG. 17, position calculation step 166 of FIG. 15 is shown in more detail in FIG. 19. In FIG. 18, an additional manipulation step 188 is incorporated as compared to the schematic of FIG. 16. Likewise, in FIG. 19, an additional manipulation step 192 is incorporated, as compared to the schematic of FIG. 17. The additional manipulation step associated with the shield device compensation method involves the manipulation of the values of the LUT. Specifically, knowledge of the geometry of the coil sets and shield device 120 is sufficient to allow manipulation of the LUT in order to account for the effect of shield device 120 within navigational domain 12. The effects of arbitrary field-influencing objects that lie in peripheral domain 15 and anterior to shield device 120 are thereby cancelled.

In particular, the LUT consists of a database containing the magnetic field amplitude values $H_x''(R)$, $H_y''(R)$, and $H_z''(R)$ at every x-y-z coordinate location within the navigational domain for five coil sets: the unidirectional coil sets for generating the uniform amplitude fields in the x, y, and z-directions denoted by n=x, y, or z; the short coil (SC) set at 0° denoted by n=1(s); and the long coil (LC) set at 0° denoted by n=1(L). The magnetic field value data for the short and long coil sets at 120° and 240° may be obtained from the LUT by rotating the field vectors for the long and short coil sets at 0° (n=(n=1(s) and n=1(L)) by the angle (i.e., ±120°) appropriate for the given coil set. The input data for the LUT consists of the x-y-z coordinates and a designation of which coil set is being used to generate the magnetic fields (the superscript "n"). In response to this input data, the LUT supplies the magnetic field amplitude values $H_x''(R)$, $H_y''(R)$, and $H_z''(R)$ at the selected x-y-z coordinates for the designated coil set. Note that in the previously discussed preferred embodiments of the present invention, the LUT can only be successfully utilized after compensation for field-influencing objects has occurred. However, in the preferred embodiment of the present invention, compensation for shield device 120 may be incorporated into the LUT.

The LUT is present to speed up the operational sequence of the location algorithm. Otherwise, an undesirable computational delay exists if the required magnetic fields from the nine coil sets must be individually calculated during each iteration of the algorithm. By predetermining the magnetic field values and storing them in LUT, the location algorithm need only access the LUT to retrieve the appropriate field value without endeavoring into any complex field analysis. This is especially true when shield device compensation is an issue. At x-y-z coordinates other than those for which magnetic field values are determined in the LUT, an interpolation procedure is employed to calculate the field value.

Detailed Description of Method for Determining Unknown Position Coordinates by Sampling a Known Navigation Field The system and method used herein is directed to the development of a series of measurements and calculations able to account for the effects of a field-influencing object that would otherwise introduce error into a position and orientation determination. The relationships defined by these systems and methods are such that the unknown effects of the field-influencing object are separable.

Figure 2:
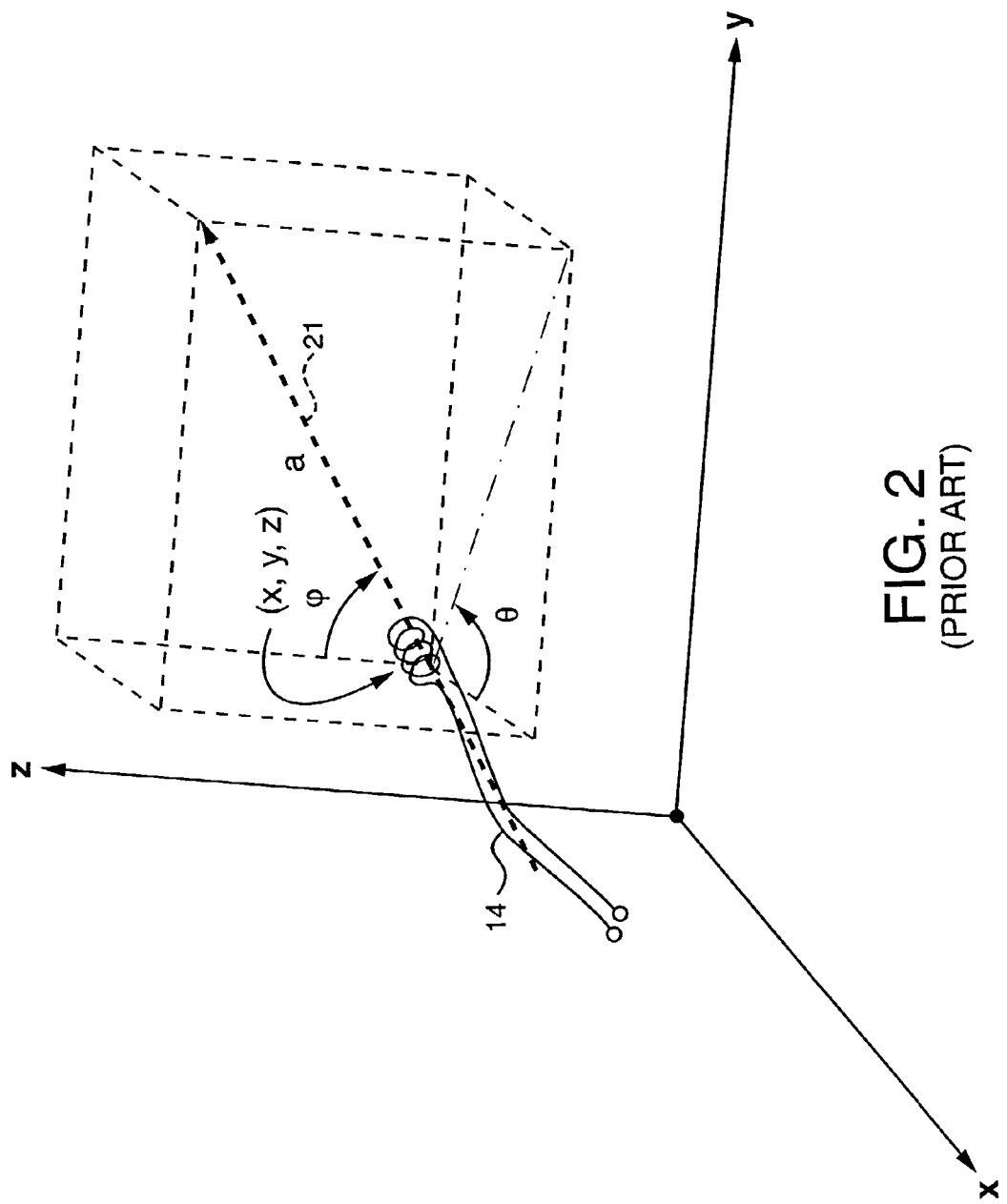
FIG. 2 is a graphical view of a prior art method of identifying the position and orientation of a sensing coil in three dimensional space.

Determining the Angular Orientation of a Probe in the Absence of Extraneous Fields This section describes in more detail the orientation calculation as indicated by the schematic of FIG. 16. The angular orientation of sensor coil 14 is represented by an angle θ corresponding to the angle of departure from the z-axis and an angle φ corresponding to the angle between the x-axis and the projection onto the x-y plane of the vector coincident with the longitudinal axis of sensing coil 14 as shown in FIG. 2.

The unidirectional coils are activated in succession, each generating a substantially uniform amplitude field that projects into navigational domain 12 and induces a corresponding voltage signal in sensing coil 14.

In access step 170 of FIG. 16, the LUT is then accessed three times to acquire the magnetic field values at the LNP for each of the three unidirectional coils. In calculation step 172, these values and the measured voltage signals are then substituted into the appropriate equations set forth below to solve for the unknown variables θ and φ that define the orientation of sensing coil 14.

By way of background, the time-dependent magnetic fields projected into the navigational domain induce voltages in sensor coil 14 that are representative of the orientation of coil axis a 21 relative to the lines of magnetic flux. The development of an induced voltage in sensing coil 14 in response to a changing magnetic field is defined by Faraday's law. For a closed stationary path in space which is linked by a changing magnetic field, the induced voltage as a function of time V(t) around this path is equal to the negative time rate of change of the total magnetic flux through the closed path (one turn). For an open surface S bounded by a closed path C, the magnetic flux ψ through S is given by, $$\psi^n = N \int_S \mu_0 H^n(t) \cdot \hat{a} \, da$$

where $\mu_0$ is the magnetic permeability of free space and is a constant, the superscript "n" simply associates a given flux $\psi^n$ with a given field $H^n(t)$, $\hat{a}$ is a vector normal to surface S, and da is a differential unit of area, and N is the number of turns in the coil 14. The mathematical statement of Faraday's law is, thus, $$V^n(t) = -\frac{d}{dt}\psi^n$$

Within the time period of a measurement of sensing coil 14, neither the surface S, or the closed path C determined by the position of sensing coil 14 are a function of time. Thus, $$V^n(t) = -N \int_S \mu_0 \frac{\partial H^n(t)}{\partial t} \bullet \hat{a} \, da$$

For an N-turn coil of wire of radius r located in a uniform amplitude magnetic field generated by coil n in a time varying harmonic field of angular frequency $\omega$, with a sinusoidal waveform $H''(t)=H''\exp(-i\omega t)$, where coil axis 21 is displaced at an angle $\rho$ with respect to the lines of magnetic flux, $i=\sqrt{(-1)}$, t is the time, and exp(n) denotes the natural base of logarithms e raised to the power n, the induced voltage measured between the two open ends of the sensing coil 14 is expressed as:

$$V^n(t) = -N \int_S \mu_0 \frac{\partial H^n(t)}{\partial t} \bullet \hat{a} \, da = -\omega N \pi r^2 \mu_0 H^n \cos(\rho) \exp(-i\omega t - i\pi/2)$$

where $H''=|H''|$. This assumes that each turn of the coil is separately and equally linked by the magnetic flux (e.g., in tightly wound coils), the induced voltage within sensing coil 14 may be approximated as the summation of the induced voltages developed in each turn.

$$V^n(t) = -N\omega\pi r^2 \mu_0 H^n \cos(\rho)\exp(-i\omega t - i\pi/2)$$

The time dependence and phase of $V^n(t)$ is given by $\exp(-i\omega t - i\pi/2)$. Notice that the phase factor of $\pi/2$ indicates that the time variation of the induced voltage $V^n(t) = -N\omega\pi r^2 \mu_0 H^n \cos(\rho)\exp(-i\omega t - i\pi/2)$ lags behind the time variation of the driving magnetic field $H''(t)=H''\exp(-i\omega t)$ by $\pi/2$ radians, or 90°. This time dependence and phase can be factored out to provide a solution for the induced voltage amplitude $V^n$ only, where $$V^n(t) = V^n \exp(-i\omega t - i\pi/2). \text{ Thus}$$

$$V^n(t) = -N\omega\pi r^2 \mu_0 H^n \cos(\rho)$$

The induced voltage amplitude $V^n$ in sensing coil 14 will vary with changes in the angular orientation between the coil axis and the direction of the magnetic field lines $\rho$.

A useful reference frame for spatially conceptualizing the interaction between sensing coil 14 and the magnetic fields in navigational domain 12 is the Cartesian coordinate system defined by mutually perpendicular axes x-y-z. As above, coil axis 21 is through sensing coil 14.

The angles $\alpha, \beta, \gamma$ that the coil axis 21 makes with the unit coordinate vectors x, y, and z respectively, are called the direction angles of coil axis 21; the trigonometric terms $\cos(\alpha), \cos(\beta)$ and $\cos(\gamma)$ represent direction cosine values. Employing vector product notation, the following expressions are provided: $\hat{a}\cdot x=\cos(\alpha), \hat{a}\cdot y=\cos(\beta),$ and $\hat{a}\cdot z=\cos(\gamma)$. Referencing the induced voltage equations set forth above, these angles $\alpha, \beta,$ and $\gamma$ correspond to the angular displacement of coil axis 21 with respect to uniform fields generated along the x-axis, y-axis, and z-axis directions, respectively. Thus, the correspondence between direction cosine expressions is as follows:

$\hat{a}\cdot x=\cos(\alpha)=\sin(\phi)\cos(\theta)$ $\hat{a}\cdot y=\cos(\beta)=\sin(\phi)\sin(\theta)$, and $\hat{a}\cdot z=\cos(\gamma)=\cos(\phi)$ Accordingly, the following relationships illustrate the dependence of induced voltage on the orientation parameters $\theta$, and $\phi$.

$$V^x=\kappa\omega H_x^x \sin(\phi)\cos(\theta)+\kappa\omega H_y^x \sin(\theta)\sin(\phi)+\kappa\omega H_z^x \cos(\phi)$$

where $\kappa=-N\pi r^2 \mu_0$ and is independent of frequency. The subscripts in the field intensity amplitudes indicate the axial dimension along which the magnetic field amplitude value was determined by accessing the LUT for the given coil set at the LNP, while the superscript in the voltage amplitude and the field intensity terms indicates the field-generating coil set: in this case the x-directed uniform amplitude field. For an x-directed substantially uniform field, the terms $H_y^x$ and $H_z^x$ are small compared to $H_x^x$. Similar equations are developed below for the induced voltages produced by the unidirectional coils successively generating a y-directed and z-directed substantially uniform field:

$$V^y=\kappa\omega H_x^y \sin(\phi)\cos(\theta)+\kappa\omega H_y^y \sin(\phi)\sin(\theta)+\kappa\omega H_z^y \cos(\phi), \text{ and}$$

$$V^z=\kappa\omega H_x^z \sin(\phi)\cos(\theta)+\kappa\omega H_y^z \sin(\phi)\sin(\theta)+\kappa\omega H_z^z \cos(\phi)$$

As above for the x-directed field, the terms $H_x^y$ and $H_z^y$ in the equation for $V^y$ and the terms $H_x^z$ and $H_y^z$ in the equation for $V^z$ are small compared to $H_y^y$ and $H_z^z$ respectively. After substituting the measured values for the induced voltage amplitude signals, the linearly independent equations are simultaneously solved to determine the unknown variables $\theta$ and $\phi$ defining the orientation of coil axis 21. This corresponds to calculation step 172 of FIG. 16.

Determining the Positional Coordinates of a Probe in the Absence of Extraneous Fields.

This section describes in more detail the position calculation as indicated by the schematic of FIG. 17. To begin with, a sequence of vector gradient fields are generated by successive delta coils. As above, consider a magnetic field waveform that is sinusoidal in nature with angular frequency $\omega$. Each vector gradient field generates a family of constant signal surfaces. The voltage amplitude $V_O^n$ is calculated at the LNP, $R_0=(x_0, y_0, z_0)$, from the LUT at the fixed orientation $(\theta, \phi)$, or $v_0^n(x_0, y_0, z_0, \theta, \phi)\exp(-i\omega t - i\pi/2)=-N\omega r^2\mu_0 H_0^n\cdot\hat{a}\exp(-i\omega t - i\pi/2)$ where coil axis $\alpha$ 21 is a unit vector that is normal to the plane determined by sensing coil 14 and is uniquely determined by the orientation variables $(\theta, \phi)$, and $H_O^n$ is the vector magnetic field produced by the "n" coil set and is evaluated at the LNP which is $R_0$. This corresponds to step 176 of FIG. 17. As noted above, the last navigation point (LNP) refers to the x-y-z positional coordinates of sensing coil 14 as determined by the immediately previous computation cycle. For the first cycle, the LNP is the center of the viewing field. The voltage amplitude $V_0^n$ calculated above is subtracted from the measured value of the voltage amplitude $V^n$ at the unknown location $R=(x, y, z)$ at the known fixed orientation $(\theta, \phi)$ or $V^n(x, y, z, \theta, \phi_x)$. The difference in these amplitude values $\Delta V^n V_0^n - V^n$ is related to the dot product of the vector gradient field at the LNP $\vec{\nabla}H_0^n(R_0)$ and a displacement vector $\Delta R=R-R_0=(\Delta x, \Delta y, \Delta z)$, where the displacement vector $\Delta R$ is assumed to be small, in the following manner:

$$\Delta V^n \exp(-i\omega t - i\pi/2) = -N\omega r^2\mu_0 \Delta R \cdot \vec{\nabla}(H_0^n \cdot \hat{a})\exp(-i\omega t - i\pi/2)$$

As before, the time dependence and phase $\exp(-i\omega t - i\pi/2)$ can be factored out and using $\kappa=-N\pi r^2\mu_{100}$, we are left with:

$$\Delta V^n = \kappa\omega\Delta R \cdot \vec{\nabla}(H_0^n \cdot \hat{a})$$

In the above equation, $\Delta V^n$ is known, the variables $\kappa$ and $\omega$ are known, as is coil axis a 21. The gradient $\vec{\nabla}(H_0^n \cdot \hat{a})$ can be calculated from the LUT using standard techniques from numerical methods. Thus, the only unknown that remains is the small displacement vector $\Delta R$ which is expressed merely as the difference between the LNP $R_0 = (x_0, y_0, z_0)$ and the unknown location vector $R = (x, y, z)$. Thus, a measurement of the amplitude of the voltage across sensor coil 14, provided that $\vec{\nabla}(H_0^n \cdot \hat{a}) \neq 0$, provides one with a non-singular equation of a function of $R = (x, y, z)$:

$$R \cdot \vec{\nabla}(H_0^n \cdot \hat{a}) = \frac{\Delta V^n}{\kappa \omega} + R_0 \cdot \vec{\nabla}(H_0^n \cdot \hat{a})$$

which has the general form $A_x^n x + A_y^n y + A_z^n = B^n$ where the variables $A_j^n$ and $B^n$ are constants. Such an equation in general determines a plane in three dimensions. Since it is assumed that the displacement vector $\Delta R$ is small, then, for a small region around the LNP $R_0 = (x_0, y_0, z_0)$, a small planar portion of the constant signal surface associated with a delta coil and a given sensing coil 14 orientation can be identified.

In particular, if the nth delta coil pair is activated and voltage measurements are taken, where the nth short coil is denoted by n(s) and the nth long coil is denoted by n(L), then the following linearly independent equations can be solved for $$R \cdot \vec{\nabla}\left(H_0^{n(S)} \cdot \hat{a}\right) = \frac{\Delta V^{n(S)}}{\kappa \omega} + R_0 \cdot \vec{\nabla}\left(H_0^{n(S)} \cdot \hat{a}\right)$$

$$R \cdot \vec{\nabla}\left(H_0^{n(L)} \cdot \hat{a}\right) = \frac{\Delta V^{n(L)}}{\kappa \omega} + R_0 \cdot \vec{\nabla}\left(H_0^{n(L)} \cdot \hat{a}\right)$$

provided that $\vec{\nabla}(H_0^{n(s)} \cdot \hat{a}) \neq 0$ or $\vec{\nabla}(H_0^{n(L)} \cdot \hat{a}) \neq 0$. Each equation independently determines a small planar region of a constant signal surface, and the simultaneous solution of both of the equations determines a line $\Im^n$ in three dimensional space on which the unknown point $R = (x, y, z)$ lies. This corresponds to calculation step 180 of FIG. 17. In practice, the delta coil pairs are constructed so that the substantially zero gradient component of both the short coil and the long coil field are in the same direction. Denoting such a direction by $c^n$, this implies by definition that $$\vec{\nabla}(H_0^{n(s)} \cdot c^n) = 0, \text{ and}$$

$$\vec{\nabla}(H_0^{n(L)} \cdot c^n) = 0$$

Thus, the line $\Im^n$ in three dimensional space determined by the above equations is parallel to the vector $c^n$ Based on the above analysis, each delta coil pair provides information for determining a line $\Im^n$ in three dimensional space upon which the point $R = (x, y, z)$ lies. Notice that, in theory, the point $R = (x, y, z)$ could be determined using only two coil pairs where the orientation of the corresponding vectors $c^1$ and $c^2$ are at 90° to each other. However, in practice, three coils are desirable because of the possibility that the orientation of the sensing coil 14 $\hat{a}$ may be such that $$\vec{\nabla}(H_0^{n(s)} \cdot \hat{a}) = 0, \text{ and}$$

$$\vec{\nabla}(H_0^{n(L)} \cdot \hat{a}) = 0$$

In such a case, the equations generated by such a measurement are not linearly independent of each other, and there is no solution that determines a unique line in three dimensional space. Thus, in practice, three delta coil pairs are used where the orientation of the corresponding vectors $c^1$, $c^2$, and $c^3$ are at 120° to each other.

Detailed Description of Extraneous Eddy Current Compensation

This section describes in more detail the eddy current compensation method as indicated by the schematic of FIG. 13.

The measurements of induced voltage amplitudes in sensing coil 14 form the basis for determining position and orientation of sensing coil 14. In practice, extraneous conducting object 23 may be present either in navigational domain 12 or peripheral domain 15 that responds to the fields generated for measurement purposes.

Figure 20A:
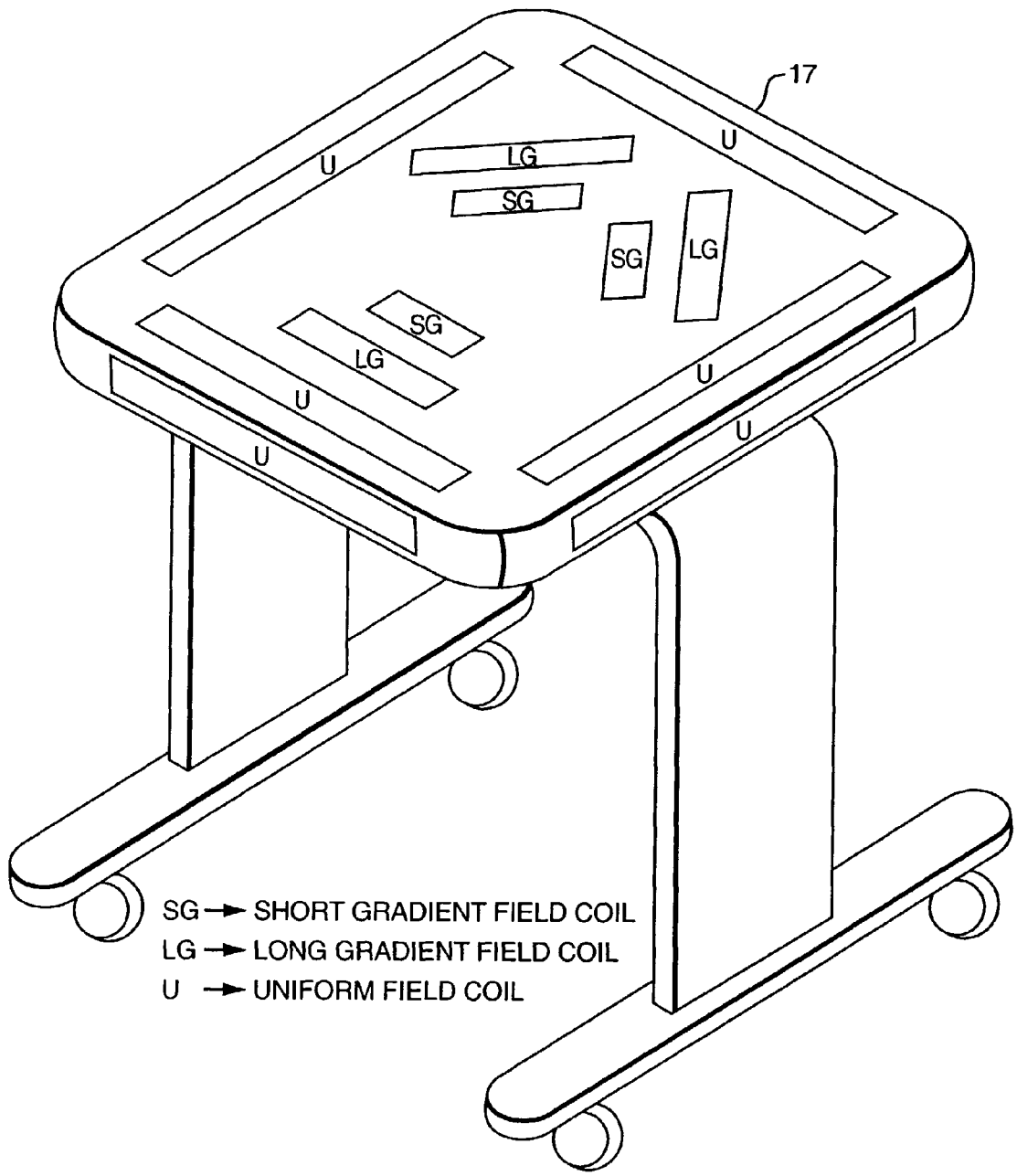
FIG. 20A shows a perspective view of the disposition of the nine coil sets of the examination deck.
Figure 20B:
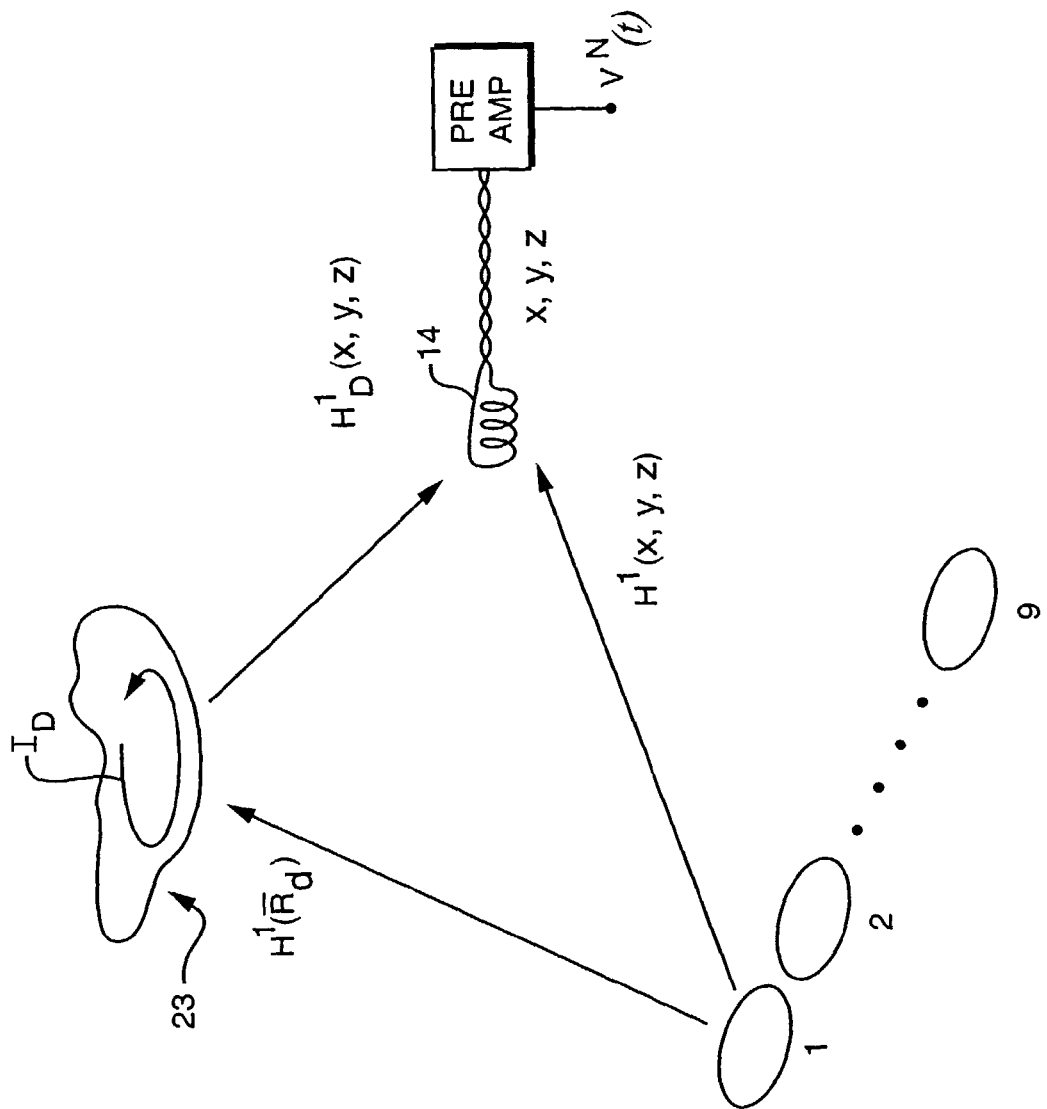
FIG. 20B shows a schematic view of the coil sets of FIG. 20A.

FIG. 20A shows the disposition of the nine coil sets of the examination deck 17; the coil sets are also shown in FIG. 20B where they are schematically represented as 1-9. Also shown in 20B is first conducting object 23, it is subjected to a field $H^1$ ($R_d$) which is the field produced by coil set #1 at the location of first conducting object 23. This field will induce eddy currents ID that flow in first conducting object 23 and these currents will produce disturbing magnetic fields of their own, these are designated $H_D^1$ (x, y, z). Thus the field present at X, Y, Z, the location of sensing coil 14 has two parts, $H^1$(X, Y, Z) the desired field upon which navigation is calculated and $H_D^1$(X, Y, Z) the disturbance. the signal produced in sensing coil 14 also has two components corresponding to the two fields. In order to isolate and separate these, one must understand the characteristics of eddy currents produced in first conducting object 23 of arbitrary shape and characteristics.

Figure 21A:
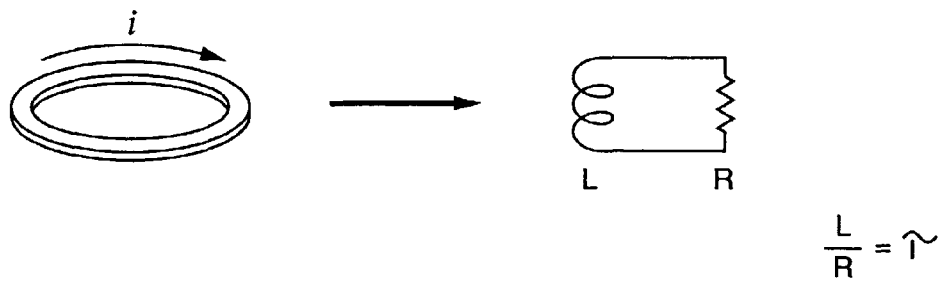
FIG. 21A shows a perspective view of an exemplary disturbance which is in the form of a metallic ring, along with the equivalent circuit model.
Figure 21B:
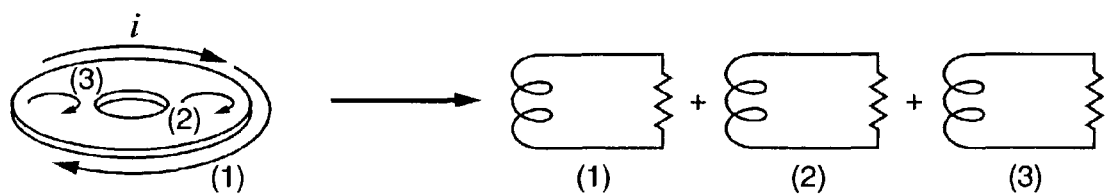
FIG. 21B shows a perspective view of an elliptical slab of metal including an off center circular hole, along with the equivalent circuit model; and, FIG. 21C shows a perspective view of a solid square metal plate, along with the equivalent circuit model.
Figure 21C:
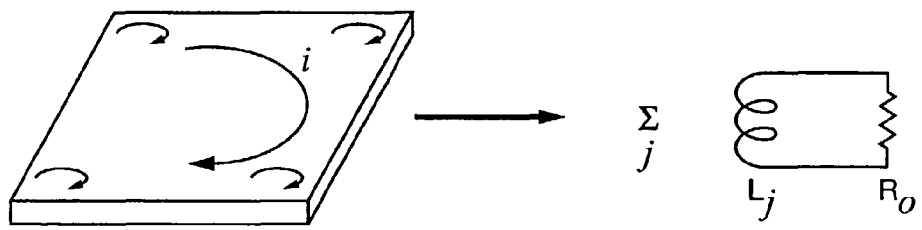

FIG. 21A depicts an exemplary disturbance in the form of a metallic ring. This ring will have an inductance L and a resistance R that depend on the dimensions and materials of the ring. The circuit on the right describes the eddy current equivalent, this circuit will have a characteristic time constant $\tau = L/R$ and have a level of excitation dependent on the orientation of the incoming field to the axis. FIG. 21B shows an elliptical slab of metal with an off center circular hole cut in it. The eddy current performance of this shape is largely described by three current loops or modes of excitation. These are numbered 1, 2, 3, each of these modes has its' own L, R and $\tau$ and its own degree of interaction to an incoming field. the eddy current equivalent is therefore a summation of three circuits each similar to that for the case shown in FIG. 21A. A similar analysis prevails in the case shown in FIG. 21C, which corresponds to a solid square plate. In each of these cases there is a dominant mode (#1) which corresponds to the current circulation around the largest dimensions of the disturbing shape, this gives the largest interaction with the incoming field and also produce the largest field generation. In general, any shape disturbance can always be described as an infinite summation of simple LR circuits.

The first objective in the following description is to show how the dominant mode of any disturbance 23 can be eliminated in its effect of the signal $V^N(t)$ and therefore eliminate its effect on navigation. The second objective is to show how higher order modes can be eliminated.

Dominant Mode Only:

The induced voltage at the sensing coil 14 has two components, the direct coupling from the transmitter coils and the indirect coupling from the first conducting object 23, which gives $$V^n(t) = \omega \exp(-i\omega t - i\pi/2)\eta_0^n + \frac{\omega^2 \exp(-i\omega t - i\pi)\eta_{eddy}^n L_{eddy}}{R_{eddy} - i\omega L_{eddy}}$$

where the coupling variables $$\eta_0^n \text{ and } \eta_{eddy}^n$$

are incorporated to indicate the coupling with the source field and the resulting eddy field respectively. Factoring out the time dependence and the phase factor $\pi/2$ as before, where, $V^n(t) = V^n \exp(-i\omega t - i\pi/2)$ the following result is obtained:

$$V^n = \omega \eta_0^n - \frac{i\omega^2 \eta_{eddy}^n L_{eddy}}{R_{eddy} - i\omega L_{eddy}}$$

If the variable $\tau_{eddy}$ is defined as:

$$\tau_{eddy} = \frac{L_{eddy}}{R_{eddy}}$$

Then the above equation can be rewritten as:

$$\frac{V^n}{\omega} = \eta_0^n - \eta_{eddy}^n \frac{i\omega \tau_{eddy}}{1 - i\omega \tau_{eddy}}$$

This equation can be rewritten in terms of real and imaginary parts:

$$\frac{V^n}{\omega} = \eta_0^n + \eta_{eddy}^n \frac{\omega^2 \tau_{eddy}^2}{1 + \omega^2 \tau_{eddy}^2} - i\eta_{eddy}^n \frac{\omega \tau_{eddy}}{1 + \omega^2 \tau_{eddy}^2}, \text{ or}$$

$$\frac{V^n}{\omega} = \eta_0^n + \eta_{eddy}^n \frac{\omega^2 \tau_{eddy}^2}{1 + \omega^2 \tau_{eddy}^2} + \exp(-i\pi/2)\eta_{eddy}^n \frac{\omega \tau_{eddy}}{1 + \omega^2 \tau_{eddy}^2}$$

Thus, first conducting object 23 has altered the magnitude of the measured voltage amplitude due to the source coils, at the expected phase shifted point $\exp(-\omega t - i\pi/2)$, by an amount $\Delta V^{n-eddy}$ equal to $$\Delta V^{n-eddy} = \eta_{eddy}^n \frac{\omega^3 \tau_{eddy}^2}{1 + \omega^2 \tau_{eddy}^2}$$

$\Delta V^{n-eddy}$ contains the two unknowns $\tau_{eddy}$ and $$\eta^{eddy}.$$

An additional voltage signal is phase shifted by a further or $\pi/2$ radians with an amplitude $$V_{\pi/2}^{n-eddy}:$$

$$V_{\pi/2}^{n-eddy} = \eta_{eddy}^n \frac{\omega^2 \tau_{eddy}}{1 + \omega^2 \tau_{eddy}^2}$$

The measured voltage drop $V^n$ can be rewritten as:

$$V^n = \omega\eta_0^n + \omega \tau_{eddy} V_{\pi/2}^{n-eddy} - i V_{\pi/2}^{n-eddy}$$

Thus, if $$V_{\pi/2}^{n-eddy}$$

and $\tau_{eddy}$ are known, the measured signal $V^n$ can be adjusted for the presence of first conducting object 23 to obtain the adjusted potential drop $$V_{adjst}^n = \omega\eta_0^n.$$

Once $$V_{adjst}^n$$

is obtained, the orientation and position calculations discussed previously can be applied using the LUT in order to obtain the proper orientation and position of sensing coil 14.

The value of the amplitude $$V_{\pi/2}^{n-eddy}$$

can be obtained directly by measurement, since it lags the expected voltage drop signal by the additional phase of $\pi/2$ radians, or 90°. Thus, only $\tau_{eddy}$ need be determined in order to compensate for an extraneous eddy current.

As before, at least one more linearly independent equation is needed in order to solve for eddy. A second linearly independent equation is obtained by taking a voltage amplitude measurement using a second magnetic field waveform, for example, taking a voltage amplitude measurement at a second angular frequency. Thus, denoting our two angular frequencies by $\omega_1$ and $\omega_2$, two linearly independent measurements are obtained:

$$V^n(\omega_2) = \omega_1 \eta_0^n + \omega_1 \tau_{eddy} V_{\pi/2}^{n-eddy}(\omega_1) - i V_{\pi/2}^{n-eddy}(\omega_1)$$

$$V^n(\omega_2) = \omega_2 \eta_0^n + \omega_2 \tau_{eddy} V_{\pi/2}^{n-eddy}(\omega_2) - i V_{\pi/2}^{n-eddy}(\omega_2)$$

The difference of the amplitudes between the two frequencies with the time dependence and phase that goes as $\exp(-i\omega t - i\pi/2)$ can be written as:

$$\text{Re}\left\{\frac{V^n(\omega_1)}{\omega_1} - \frac{V^n(\omega_2)}{\omega_2}\right\} = \tau_{eddy}\left\{V_{\pi/2}^{n-eddy}(\omega_1) - V_{\pi/2}^{n-eddy}(\omega_2)\right\}$$

where "Re" denotes the real part of the enclosed quantity. Meanwhile, the difference of the amplitudes between the two frequencies with the time dependence and phase that goes as $\exp(-i\omega\tau-i\pi)$ can be written as:

$$\text{Im}\{V^n(\omega_1) - V^n(\omega_2)\} = \left\{V_{\pi/2}^{n-eddy}(\omega_2) - V_{\pi/2}^{n-eddy}(\omega_1)\right\}$$

where "Im" denotes the imaginary part of the enclosed quantity. Thus:

$$\tau_{eddy} = \frac{\text{Re}\left\{\frac{V^n(\omega_2)}{\omega_2} - \frac{V^n(\omega_1)}{\omega_1}\right\}}{\text{Im}\{V^n(\omega_1) - V^n(\omega_2)\}}$$

This corresponds to a portion of calculation step 138 of FIG. 13 in one embodiment of the present invention. Therefore, since $\tau_{eddy}$ can be determined according to voltage measurements at two angular frequencies, and since the magnitude of the phase lagged amplitude $$V_{\pi/2}^{n-eddy}$$

can also be measured, then the adjusted voltage drop to be used with the LUT, $$V_{adjst}^n = \omega\eta_0^n,$$

can be determined as a function of the measured voltage drop $V^n$:

$$V_{adjst}^n = \omega\eta_0^n = \text{Re}\{V^n\} + \omega\tau_{eddy}\text{Im}\{V^n\}$$

This, again, corresponds to calculation step 138 of FIG. 13 in one embodiment of the present invention.

Eddy Current Compensation in the Case of Two Extraneous Conducting Objects

The analysis in the previous section applied to the case a disturbing magnetic field introduced by first conducting object 23. the analysis in this section applies to the case where there is first conducting object 23 and second conducting object 31 where each has, respectively, independent values of $\tau_1$ and $\tau_2$.

For the case of first conducting object 23 and second conducting object 31, each with a different value of $\tau_1$ and $\tau_2$, respectively, and with different coupling constants: $\eta_1''$ and $\eta_2''$, the above equation determining $$V_{adjst}^n = \omega\eta_0^n$$

changes. In this case, the potential drop measured across sensing coil 14 based on a model consistent with the present invention becomes:

$$\frac{V^n}{\omega} = \eta_0^n + \eta_1^n \frac{\omega^2\tau_1^2}{1+\omega^2\tau_1^2} - i\eta_1^n \frac{\omega\tau_1}{1+\omega^2\tau_1^2} + \eta_2^n \frac{\omega^2\tau_2^2}{1+\omega^2\tau_2^2} - i\eta_2^n \frac{\omega\tau_2}{1+\omega^2\tau_2^2}$$

where $\eta_1''$ and $\tau_1$ correspond to first conducting object 23 and and $\eta_2''$ and $\tau_2$ correspond to second conducting object 31. Thus, for a given real and imaginary measurement of $V^n$ across sensing coil 14, there are 5 unknowns $\eta_0''$, $\eta_1''$, $\eta_2''$, $\eta_1''$, $\tau_1$, and $\tau_2$. By equating the real and imaginary portions of the measurements across sensing coil 14 with the real and imaginary portions of the above equations, there are two linearly independent equations. thus, there are an insufficient number of equations to determine all five of the unknowns $\eta_0''$, $\eta_1''$, $\eta_2''$, $\eta_1''$, $\tau_1$, and $\tau_2$.

A measurement at two frequencies $\omega_1$ and $\omega_2$ as was outlined above, yields four equations. There are still five unknowns, however. Thus, there are still an insufficient total number of equations to solve for all of the terms and determine $$V_{adjst}^n = \omega\eta_0^n.$$

A measurement at three frequencies $\omega_1$, $\omega_2$, and $\omega_3$, however, yields a sufficient number of equations in order to determine all of the variables, and allows for the calculation of $$V_{adjst}^n = \omega\eta_0^n.$$

Specifically, by taking voltage drop measurements across sensing coil 14 at three frequencies, the following equations are obtained:

$$\frac{V^n(\omega)}{\omega} = \eta_0^n + \eta_1^n \frac{\omega^2\tau_1^2}{1+\omega^2\tau_1^2} - i\eta_1^n \frac{\omega\tau_1}{1+\omega^2\tau_1^2} + \eta_2^n \frac{\omega^2\tau_2^2}{1+\omega^2\tau_2^2} - i\eta_2^n \frac{\omega\tau_2}{1+\omega^2\tau_2^2}$$

where $\omega$ is selected from the set $\omega=(\omega_1, \omega_2, \omega_3)$. In the above equations, the unknowns $\eta_1''$ and $\eta_2''$ appear as linear coefficients. Therefore, by subtracting a measurement of $$\frac{V^n}{\omega_1}$$

taken by sensing coil 14 from a measurement of $$\frac{V^n}{\omega_2},$$

the above equations can be rewritten in the general form $$\eta_1^n = f_1(\omega_1, \omega_2, \tau_1, \tau_2), \text{ and}$$
$$\eta_2^n = f_2(\omega_1, \omega_2, \tau_1, \tau_2)$$

where $f_1(\omega_1, \omega_2, \tau_1, \tau_2)$ and $f_2(\omega_1, \omega_2, \tau_1, \tau_2)$ are polynomial functions of $\omega_1, \omega_2, \tau_1,$ and $\tau_2$.

In addition, by subtracting a measurement of $$\frac{V^n}{\omega_1}$$

taken by sensing coil 14 from a measurement of $$\frac{V^n}{\omega_3},$$

the above equations can also be rewritten in the general form $$\eta_1^n = g_1(\omega_1, \omega_3, \tau_1, \tau_2), \text{ and}$$
$$\eta_2^n = g_2(\omega_1, \omega_3, \tau_1, \tau_2)$$

where again $g_1(\omega_1, \omega_3, \tau_1\tau_2)$ and $g_2(\omega_1, \omega_3, \tau_1, \tau_2)$ are polynomial functions of $\omega_1, \omega_3, \tau_1,$ and $\tau_2$. Therefore, the following polymial equations provide two equations with two unknowns:

$$g_1(\omega_1,\omega_3,\tau_1,\tau_2) = f_1(\omega_1,\omega_3,\tau_1,\tau_2), \text{ and}$$
$$g_2(\omega_1,\omega_3,\tau_1,\tau_2) = f_2(\omega_1,\omega_3,\tau_1,\tau_2).$$

The above two equations can be solved to determine $\tau_1$, and $\tau_2$, and, thus, the value of $$V_{adjst}^n = \omega \eta_0^n$$

can be determined in the presence of first conducting object 23 and second conducting object 31. The solution to the above equations yields the adjusted value of the potential drop measurement and corresponds to calculation step 138 of FIG. 13 in one embodiment of the present invention.

Eddy Current Compensation in the Case of Two or More Extraneous Conducting Objects The general result, consistent with the present invention, is that resolving m values of $\tau_m$, requires m measurements of real and imaginary parts of the potential drop across sensing coil 14, using m different waveforms. For example, measurements of a sinusoidal waveform at the set of frequencies ($\omega_1$, $\omega_2, \ldots \omega_m$) are sufficient to resolve m values of $\tau_m$. Since each additional conducting body introduces a new variable $\tau_m$ and an associated coupling constant $\eta_m^n$, each additional conducting body introduces two new unknowns. However, a measurement of a potential drop across sensing coil 14 at a new waveform m, including both the real and imaginary portions, yields the required number of two new equations necessary to resolve $\tau_m$ and $\eta_m^n$.

As above, with first conducting object 23 and second conducting object 31, higher order polynomial expressions can be derived and the value of $$V_{adjst}^n = \omega \eta_0^n$$

can be solved for, consistent with the present invention.

Alternatively, one embodiment of the present invention employs a numerical method to solve for $$V_{adjst}^n = \omega \eta_0^n.$$

In one embodiment of the present invention, a Taylor series about $\omega = \omega_1$ can be derived as follows:

$$\frac{V^n}{\omega} = \frac{V^n}{\omega_1} + \frac{\partial}{\partial \omega}\left(\frac{V^n}{\omega_1}\right)(\omega - \omega_1) + \frac{1}{2}\frac{\partial^2}{\partial \omega^2}\left(\frac{V^n}{\omega_1}\right)(\omega - \omega_1)^2 + R_3$$

where $R_3$ indicates that the neglected terms are of the third order in the derivative of $$\frac{V^n}{\omega}, \frac{\partial}{\partial \omega}\left(\frac{V^n}{\omega_1}\right)$$

denotes a first derivative of the function $$\frac{V^n}{\omega}$$

with respect to $\omega$ evaluated at $\omega = \omega_1$, and $$\frac{\partial^2}{\partial \omega^2}\left(\frac{V^n}{\omega_1}\right)$$

denotes a second derivative of the function $$\frac{V^n}{\omega}$$

with respect to $\omega$ evaluated at $\omega = \omega_1$.

Considering the relationship derived above for the effect of first conducting object 23 and second conducting object 31

$$\frac{V^n}{\omega} = \eta_0^n + \eta_1^n \frac{\omega^2 \tau_1^2}{1+\omega^2 \tau_1^2} - i\eta_1^n \frac{\omega \tau_1}{1+\omega^2 \tau_1^2} + \eta_2^n \frac{\omega^2 \tau_2^2}{1+\omega^2 \tau_2^2} - i\eta_2^n \frac{\omega \tau_2}{1+\omega^2 \tau_2^2}$$

the term $$\eta_0^n$$

is the only variable that appears without any associated factors of $\omega$. Thus, collecting similar powers of $\omega$ yields the relationship:

$$\eta_0^n = \frac{V^n}{\omega_1} - \frac{\partial}{\partial \omega}\left(\frac{V^n}{\omega_1}\right)\omega_1 - \frac{1}{2}\frac{\partial^2}{\partial \omega^2}\left(\frac{V^n}{\omega_1}\right)\omega_1^2 + R_3 \text{ or}$$

$$V_{adjst}^n = V^n - \frac{\partial}{\partial \omega}\left(\frac{V^n}{\omega_1}\right)\omega_1^2 + \frac{1}{2}\frac{\partial^2}{\partial \omega^2}\left(\frac{V^n}{\omega_1}\right)\omega_1^2 + R_3$$

The quantity $V^n$ is measured at sensing coil 14 at a frequency $\omega_1$ while the quantity $$\frac{\partial}{\partial \omega}\left(\frac{V^n}{\omega_1}\right)$$

can be determined from measurements at sensing coil 14 at any two of three frequencies $\omega_1$, $\omega_2$, and $\omega_3$, or using all three frequencies $\omega_1$, $\omega_2$, and $\omega_3$. In addition, the quantity $$\frac{1}{2}\frac{\partial^2}{\partial \omega^2}\left(\frac{V^n}{\omega_1}\right)$$

can be determined from measurements at sensing coil 14 at three frequencies $\omega_1$, $\omega_2$, and $\omega_3$. Thus, using measurements at sensing coil 14 at three frequencies $\omega_1$, $\omega_2$, and $\omega_3$, the adjusted value for the potential drop across sensing coil 14 can be determined according to:

$$V_{adjst}^n = V^n - \frac{\partial}{\partial \omega}\left(\frac{V^n}{\omega_1}\right)\omega_1^2 + \frac{1}{2}\frac{\partial^2}{\partial \omega^2}\left(\frac{V^n}{\omega_1}\right)\omega_1^2 + R_3$$

for the situation where there are multiple conducting objects that induce eddy currents and when there are multiple values of $\tau_m$.

The above example utilized magnetic field waveforms that were sinusoidal in nature at a set of frequencies $\omega$. However, a Taylor series expansion about any suitable waveform variable can be variably derived and is consistent with an embodiment of the present invention.

Eddy Current Compensation Using Singular Value Decomposition

Another embodiment of the present invention utilizes the relationship derived above for the case of first conducting object 23 only:

$$V_{adjst}^n = \omega \eta_0^n = \text{Re}\{V^n\} + \omega \tau_{eddy} \text{Im}\{V^n\}$$

this equation can be rewritten:

$$\text{Re}\{V^n\} = V_{adjst}^n - \omega \tau^* \text{Im}\{V^n\}$$

where $$\text{Re}\{V^n\}$$

is determined from a measurement across sensing coil 14, $$\text{Im}\{V^n\}$$

is also determined from a measurement across sensing coil 14, $\omega_1$ is known and both $\tau^*$ and $$V_{adjst}^n$$

are unknown. The notation $\tau^*$ is used here merely to indicate a composite $\tau_{eddy}$ that may be a result from several conducting objects. from the general relationship derived above $$\frac{V^n}{\omega} = \eta_0^n + \eta_{eddy}^n \frac{\omega^2 \tau_{eddy}^2}{1+\omega^2 \tau_{eddy}^2} - i\eta_{eddy}^n \frac{\omega \tau_{eddy}}{1+\omega^2 \tau_{eddy}^2}$$

the next higher order correction appears as to a composite $\tau^*$ can be written as:

$$\text{Re}\{V^n\} = V_{adjst}^n - \omega \, \text{Im}\{V^n\}(\tau^* + \omega \tau^{**})$$

where the notation $\tau^{**}$ indicates that it is a correction to the term $\tau^*$ appearing as a coefficient to $\omega$. the units of $\tau^{**}$ correspond to the units of $(\tau^*)^2$.

In the above equation, there are three unknowns $\tau^*$, $\tau^{**}$, and $$V_{adjst}^n.$$

In one embodiment of the present invention, it is found that measurements at sensing coil 14 of $$\text{Re}\{V^n\} \text{ and } \text{Im}\{V^n\}$$

at four frequencies $\omega_1, \omega_2, \omega_3$, and $\omega_4$, and which yields four equations $$Re\{V^n\} = V^n_{adjst} - \omega \, Im\{V^n\}(\tau^* + \omega\tau^{**})$$

with three unknowns $\tau^*, \tau^{**}$, and $$V^n_{adjst},$$

is sufficient to determine $$V^n_{adjst}$$

with the desired precision. Specifically, the above four equations with three unknowns is solved using singular value decomposition, as described, for example, in Numerical Recipes, Cambridge (1986), by W. H. press, B. P. Flannery, S. A. Teukolsky, and W. T. Vetterling. This, again, corresponds to calculation step 138 of FIG. 13.

Again, the above example utilized magnetic field waveforms that were sinusoidal in nature at a set of frequencies **. however, a similarly derived relationship about any suitable waveform variable can be utilized and is consistent with an embodiment of the present invention.

Detailed Description of Ferromagnetic and Conductive Object Compensation

This section describes in more detail the ferromagnetic and conductive object compensation method as indicated by the schematic of FIG. 14.

A pure magnetic core is a source of magnetic flux. The primary quality of a pure magnetic core is that it can enhance, or focus, magnetic field flux lines along a preferred direction. With respect to Faraday's Law $$V^n(t) = -\int_S \mu \frac{\partial H^n(t)}{\partial \tau} \cdot a \, da$$

where the quantity on the right is proportional to the time rate of change of magnetic flux, it can be seen that, as a source of flux lines, a pure magnetic object will act to enhance the voltage drop. Thus, for a pure magnetic object with tool coil 19 surrounding the magnetic core, tool coil 19 will produce a voltage drop as a function of a source field $H^n(R, t)$ $$V^n_{magn}(t) = -T \int_{S_{magn}} \mu \frac{\partial H^n(t)}{\partial \tau} \cdot a_{magn} \, da_{magn}$$

where T is a multiplication factor that represents the enhancement of the magnetic flux through tool coil 19.

Surgical tool 108 of FIG. 10 has some qualities of a pure magnetic object, as well as additional properties. Like a pure magnetic object, it can act to enhance the detection of flux lines through the center of tool coil 19 as above. However, it also responds to an applied field in a nonlinear manner, as is indicated on hysteresis graph 100. Furthermore, the additional presence of conductive elements introduce additional fields that are out of phase by $\pi/2$ with any enhanced field in the vicinity. Thus, a general form for the voltage drop across tool coil 19 affixed around surgical tool 108:

$$V^n_{ferro}(t) = -(T_{Re} - iT_{Im}) \int_{S_{ferro}} \mu \frac{\partial H^n(t)}{\partial \tau} \cdot a_{ferro} \, da_{ferro}$$

where the multiplicative factor now has both a real $T_{Re}$ and imaginary $T_{Im}$ component. As before, with the discussion of eddy currents, the voltage drop across tool coil 19 located on surgical tool 108 can be written as:

$$V^n_{ferro}(t) = \omega \exp(-i\omega t - i\pi/2)(T_{Re} - iT_{Im})T^n_{ferro}$$

To understand how the field that affects tool coil 19 located at surgical tool 108 affects sensing coil 14 located at the catheter, consider the above equation for tool coil 19 at surgical tool 108:

$$V^n_{ferro}(t) = -(T_{Re} - iT_{Im}) \int_{S_{ferro}} \mu \frac{\partial H^n(t)}{\partial \tau} \cdot a_{ferro} \, da_{ferro}$$

If both the surface area contained by tool coil 19 $S_{ferro}$ and the normal vector $a_{ferro}$ were slowly changed such that they ultimately coincided with the surface area S of sensing coil 14 at the catheter probe sensor and the unit vector associated with sensing coil axis a 21, but all other quantities were kept fixed, including the position—surgical tool 108, the source field that is being integrated over $H^n(R, t)$ would no longer be associated with the multiplicative factor $(T_{Re} - iT_{Im})$. This is the usual source field that can provide orientation and location information. However, ferromagnetic and conductive object 29 still acts as a multiplier of flux lines in this source field along a preferred axis with the factor $(T_{Re} - iT_{Im})$. And so there are two sources of flux to be considered. Thus, the following general equation is obtained for the two sources of flux in this case at sensing coil 14:

$$V^n(t) = \omega \exp(-i\omega t - i\pi/2)\eta^n_0 + \omega \exp(-i\omega t - i\pi/2)(T_{Re} - iT_{Im})\eta^n_{ferro}$$

where $$\eta^n_{ferro}$$

is related to $$\Gamma^n_{ferro}$$

by a proportionality constant. As before, $V^n(t)$ is the measured voltage drop across sensing coil 14 located at the catheter.

Again, factoring out the time dependence and the phase factor $\pi/2$ as before, where $$v^n(t) = V^n \exp(-i\omega\tau - i\pi/2), \text{ and } V^n_{ferro}(t) = V^n_{ferro}\exp(-i\omega\tau - i\pi/2)$$

the following is obtained:

$$V^n = \omega\eta^n_0 + \omega\eta^n_{ferro}(T_{Re} - iT_{Im}), \text{ and } V^n_{ferro} = \omega\Gamma^n_{ferro}(T_{Re} - iT_{Im})$$

For a suitable choice of K that satisfies the equation:

$$\text{Im}\{V^n - KV^n_{ferro}\} = 0$$

the precise proportionality constant between $$\eta^n_{ferro} \text{ and } \Gamma^n_{ferro}$$

is obtained. This corresponds to calculation step 156 of FIG. 14. Therefore, the effect of surgical tool 108 can be subtracted out from the voltage measurement induced at the catheter:

$$V^n_{adjst} = \omega\eta^n_0 = V^n - KV^n_{ferro}$$

This corresponds to calculation step 160 of FIG. 14. As before, with first conductive object 23 and an eddy current, the adjusted fields have been obtained to be used with the LUT in order to determine the proper orientation and position.

Detailed Description of Shield Device Compensation

Figure 19:
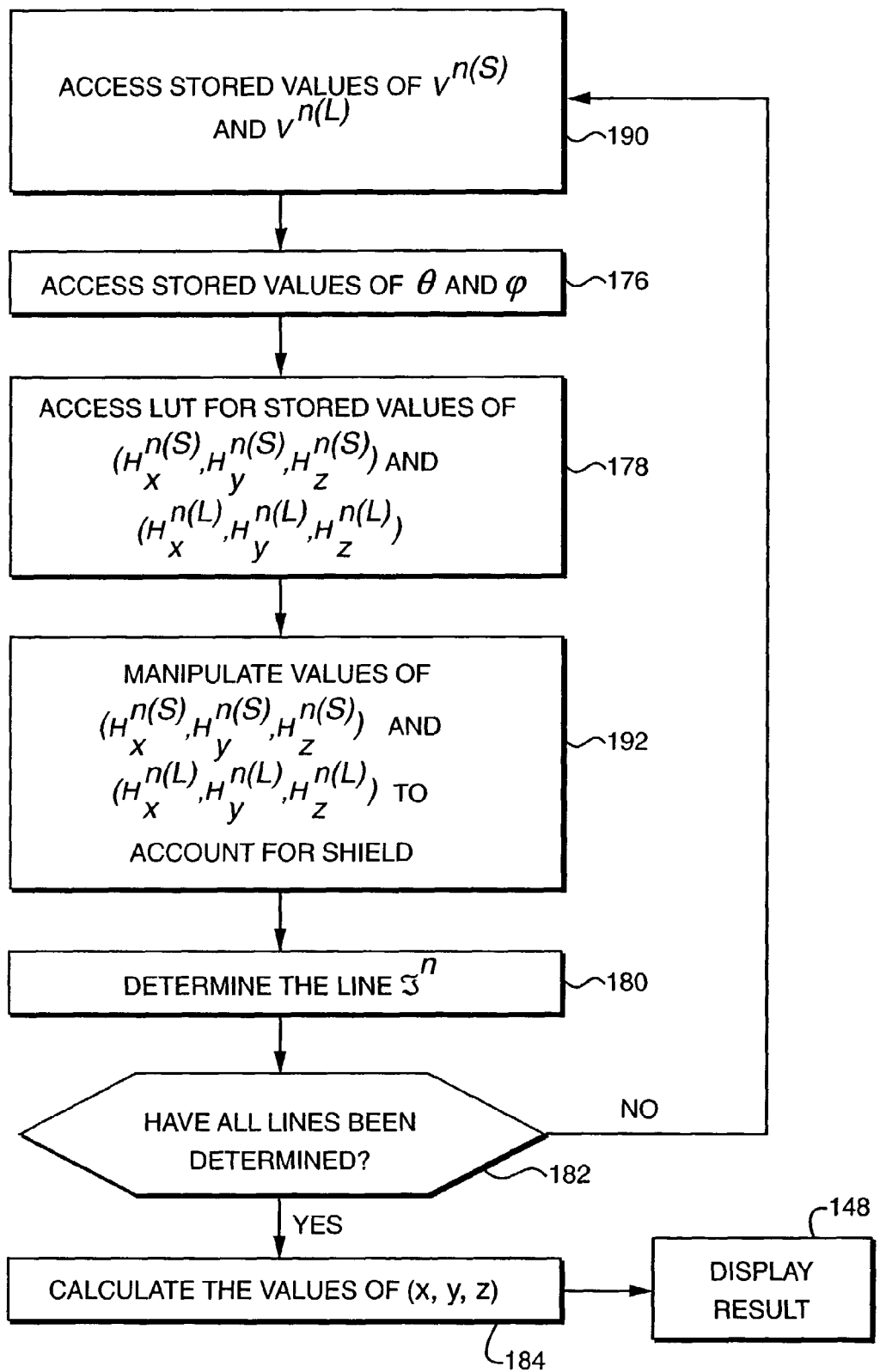
FIG. 19 shows a more detailed flow diagram for the position calculation step of FIG. 15.

This section describes in more detail the shield device compensation method as indicated by the schematics of FIGS. 15, 18, and 19.

As is evident from the discussion above, small distortions may have negligible results on the navigated position. However, large distortions can cause the system to report larger errors or even fail to compute a position. For a medical application, disturbances can include the operating table, a headholder or other any number of other metallic items.

With respect to an operating room table, the field coils will necessarily be adjacent to the operating room table. Thus, any field-influencing effect of an operating room table has the potential to create a larger than typical distortion in the fields located in the navigational domain.

In particular, shield device 120 is provided to restrict the propagation of magnetic fields through it, as, for example, a sheet of conductive material. It may be arranged in any suitable geometry that has a fixed relationship to the transmission coils. There are many possible materials that the plate can be made from, such as aluminum, copper or virtually any other conductive material. It is also possible to use materials other than a conductive sheet such as a mesh or strips of material. A further possibility is a plastic of polymer film with a conductive coating.

Shield device 120 should preferably be placed between the transmitter coil array and the disturbance. In an operating room, if the patient were to lay on the transmitter coil array, then shield device 120 could be placed under the array to block effects of the operating table. An additional enhancement could be made by bending the sides of shield device 120 up at an angle to negate the effects of the length of the operating table. Other arrangements for shield device 120 are possible, such as placing it to block the effects of microscopes or C-arms that may be present in the field.

The device alters the fields produced by the transmitter coils. The effect of the device can either be computed from electromagnetic theory, as for example, from "Static and Dynamic Electricity" third edition, Taylor & Francis (1989) by William R. Smythe. The effect could also be measured in a calibration process. Both of these techniques correspond to steps 188 and 192 of FIGS. 18 and 19 respectively. A fixed geometry can be characterized by a fixed alteration of the transmitted field. If the device is to be moved, a dynamic correction of the effect should be performed.

CONCLUSION

Methods and apparatus consistent with the present invention correct for the effects of field-influencing objects on a position and orientation determinations using magnetic fields. The foregoing description of an implementation of the invention has been presented for purposes of illustration and description. It is not exhaustive and does not limit the invention to the precise form disclosed. Modifications and variations are possible in light of the above teachings or may be acquired from practicing the invention. For example, step 144 in FIGS. 13 and 14 was indicated as occurring after all of the coil sets were activated and measured. Step 144, however, can be placed after step 140 in both FIGS. 13 and 14 and is consistent with the present invention. Also, there may be a more efficient manner of processing measurements and calculations in parallel, rather than the linear schematic presented. In addition, the magnetic field was considered to have a sinusoidal waveform at an angular frequency $\omega$, but other examples of waveforms are possible consistent with an embodiment of the present invention, including sawtooth waves, or square waves. Also, in the discussion above with regard to the analysis of voltage signals resulting from multiple waveforms, reference was made to a technique known as singular value decomposition. However, the use of any numerical technique for solving an overspecified equation is consistent with the present invention.

What is claimed is:

1. A system for navigating a probe in the presence of a field-influencing object, said system comprising:
   a sensing coil fixed to the probe operable to be navigated;
   a tool coil operably connected to a tool;
   a transmitter operable to radiate field energy sufficient to induce a signal in said sensor, wherein said transmitter includes:
   (i) three unidirectional coil sets, each of said unidirectional coil sets being driven by a drive unit capable of driving said unidirectional coil sets at a first sinusoidal wave form at a first frequency, and
   (ii) six delta coil sets, each of said delta coil sets being driven by a drive unit capable of driving said delta coil sets at said first sinusoidal wave form at said first frequency, such that said three unidirectional coil sets and said six delta coil sets produce field energy at said first frequency;

a shield operable to reflect said field energy; and a processor operable to determine a location of said sensor based upon said signal induced in said sensor;

wherein said shield is placed between said transmitter and the field influencing object to block affects of the field influencing object on the field energy;

wherein said tool is a second field-influencing object and said field energy induces a first signal in said sensing coil and a second signal in said tool coil simultaneously;

wherein said processor is operable, using said first and second signals, to isolate an affect of the tool on said sensing coil by subtracting a voltage induced in the sensing coil by the tool.

2. The system as defined in claim 1 further comprising a storage device containing information corresponding to said field energy at selected locations, said information including shield information incorporating an effect of said shield at said selected locations.

3. The system as defined in claim 2 wherein said processor is further operable to access said storage device to determine an effect of said shield on said sensor, to thereby permit a substantially precise location of said sensor to be determined despite the presence of the field influencing object.

4. The system as defined in claim 2 wherein said storage device containing said shield information includes a geometry of said shield.

5. The system as defined in claim 1 wherein the sensor is connected to a probe that is selected from a group comprising a flexible catheter, a rigid catheter, a surgical tool, a drill, and a reamer.

6. The system as defined in claim 1 wherein said sensor is fixedly connected to a distal end of a catheter insertable into a selected body cavity of a patient undergoing a surgical procedure.

7. The system as defined in claim 1 wherein said field energy is electro-magnetic field energy.

8. The system as defined in claim 1 wherein said shield is formed of a conductive material.

9. The system as defined in claim 8 wherein said conductive material is selected from a group comprising aluminum, copper, and a polymer film with a conductive coating.

10. The system as defined in claim 1 wherein said shield is formed as a conductive sheet.

11. The system as defined in claim 1 wherein said shield is formed as a conductive mesh.

12. The system as defined in claim 1 wherein said shield is formed from strips of conductive material.

13. The system as defined in claim 1 wherein said shield is fixed relative to said transmitter.

14. The system as defined in claim 13, wherein the shield is a distance from said transmitter.

15. The system as defined in claim 1 wherein said determinable location of said sensor by said processor includes angular orientation and positional coordinates of said sensor.

16. The system of claim 1 wherein said shield is a geometrically shaped thin member positioned adjacent to a navigational domain defined by the transmitter;

wherein the shield cancels the effects of the field influencing object positioned beyond the navigational domain.

17. The system as defined in claim 1, wherein the field influencing object is selected from a group comprising an operating table, a microscope, a C-arm, and an instrument having a ferromagnetic and conducting core.

18. A method for navigating a probe in the presence of a field-influencing object, said system comprising:

radiating field energy sufficient to induce a signal in a sensor;

reducing propagation of said field energy through a shield;

storing information values in a look-up-table (LUT) corresponding to said field energy at selected locations wherein the values in the LUT are adjusted with voltage adjustment values incorporating an effect of said shield at said selected locations;

accessing said stored information by a processor; and determining a location of said sensor be executing instructions with said processor based upon said signal induced in said sensor and said accessed stored information despite the presence of the field influencing object;

wherein said field energy is radiated with,
(i) three unidirectional coil sets, each of said unidirectional coil sets driven by a drive unit capable of driving said unidirectional coil sets at a first sinusoidal wave form at a first frequency, and
(ii) six delta coil sets, each of said delta coil sets driven by a drive unit capable of driving said delta coil sets at said first sinusoidal wave form at said first frequency, such that said three unidirectional coil sets and said six delta coil sets produce field energy at said first frequency.

19. The method as defined in claim 18 further comprising manipulating, for each of the unidirectional and delta coils, values in the LUT stored in the storage device to generate the adjusted values as a predetermined function of said shield, so as to produce nine (9) sets of manipulated magnetic field values as the adjusted values, each corresponding to navigational magnetic energy from one of the unidirectional coils and delta coils.

20. The method as defined in claim 18 wherein the sensor is connected to a probe that is selected from a group comprising a flexible catheter, a rigid catheter, a surgical tool, a drill, and a reamer.

21. The method as defined in claim 18 wherein said sensor is fixedly connected to a distal end of a catheter insertable into a selected body cavity of a patient undergoing a surgical procedure.

22. The method as defined in claim 18 wherein said field energy is electro-magnetic field energy.

23. The method as defined in claim 18 wherein said shield is formed of a conductive material.

24. The method as defined in claim 18 wherein said conductive material is selected from a group comprising aluminum, copper, and a polymer film with a conductive coating.

25. The method as defined in claim 18 wherein said shield is formed as a conductive sheet.

26. The method as defined in claim 18 wherein said shield is formed as a conductive mesh.

27. The method as defined in claim 18 wherein said shield is formed from strips of conductive material.

28. The method as defined in claim 18, wherein the shield is a distance from said transmitter and operable to reflect said field energy radiated from said transmitter.

29. A method for navigating a sensor within a navigational domain in the presence of a field influencing object, said method comprising:

generating a field operable to induce a signal in a sensor with a transmitter, wherein the transmitter includes:
(i) driving each of three unidirectional coil sets at a first sinusoidal wave form at a first frequency, and
(ii) driving each of six delta coil sets at said first sinusoidal wave form at said first frequency, such that said three unidirectional coil sets and said six delta coil sets produce field energy at said first frequency;

reflecting the field with a shield that separates a field influencing object from both the transmitter and the sensor, thus forming a reflected field with the shield separate from the field generated with the transmitter;

inducing a first signal within the sensor from the produced field energy;

inducing a second signal within the sensor from the reflected field energy; and determining a location of the sensor at least in part using the first signal and the second signal induced in the sensor with a processor configured to calculate, for each of the unidirectional and delta coil sets, an adjusted signal value as a predetermined function of the first signal and the second signal, so as to produce nine adjusted signal values, each corresponding to field energy from one of the unidirectional coil sets and the delta coil sets.

30. The method of claim 29, further comprising actuating the transmitter to radiate field energy.

31. A system for navigating a probe in the presence of a field-influencing object, said system comprising:

a first sensor;

a transmitter operable to radiate transmitter field energy sufficient to induce a first signal in said first sensor, wherein said transmitter includes:

(i) three unidirectional coil sets, each of said unidirectional coil sets being driven by a drive unit capable of driving said unidirectional coil sets at a first sinusoidal wave form at a first frequency, and (ii) six delta coil sets, each of said delta coil sets being driven by a drive unit capable of driving said delta coil sets at said first sinusoidal wave form at said first frequency, such that said three unidirectional coil sets and said six delta coil sets produce said transmitter field energy at said first frequency;

a shield positioned between said transmitter and the field-influencing object to reflect said transmitter field energy to substantially cancel effects of the field-influencing object; and a processor operable to determine a location of said first sensor based upon said first signal induced in said first sensor by calculating for each of the unidirectional and delta coil sets a signal value corresponding to field energy from each of the unidirectional coil sets and the delta coil sets as a part of the first signal;

wherein said shield is placed between said transmitter and the field-influencing object to block affects of the field-influencing object on said transmitter field energy.

32. The system of claim 31, further comprising:

a storage device containing information corresponding to said transmitter field energy and a reflected field energy at selected locations;

wherein said information includes shield information incorporating an effect of said shield at said selected locations;

wherein said effect of said shield includes said reflected field reflected from the shield that is separate from said transmitter field energy generated with the transmitter;

wherein said processor, in determining the location of the first sensor, is further operable to use a second signal induced in the first sensor based upon said reflected field and for each of the unidirectional and delta coil sets, an adjusted signal value as a predetermined function of the first signal and the second signal, so as to produce nine adjusted signal values, each corresponding to field energy from one of the unidirectional coil sets and the delta coil sets.

33. The system as defined in claim 32 wherein the sensor is connected to a probe operable to be navigated in a human body, wherein the probe is selected from a group comprising a flexible catheter, a rigid catheter, a surgical tool, a drill, and a reamer.

34. The system of claim 33, further comprising:

a second sensor affixed to the field-influencing object and the transmitter inducing in said second sensor a third signal in said second sensor;

wherein the processor is operable to receive said third signal from said second sensor on said field-influencing object;

wherein said processor is operable to access the information in the storage device regarding the transmitter field energy and the reflected field energy;

wherein the processor is operable to determine the location of the first sensor based on all of the third signal and the information stored in the storage device.

35. The system as defined in claim 31 wherein said sensor is fixedly connected to a distal end of a catheter insertable into a selected body cavity of a patient undergoing a surgical procedure.

36. The system as defined in claim 31 wherein said field energy is electro-magnetic field energy.

37. The system as defined in claim 31 wherein said shield is formed of a conductive material.

38. The system as defined in claim 37 wherein said conductive material is selected from a group comprising aluminum, copper, and a polymer film with a conductive coating.

39. The system as defined in claim 31 wherein said shield is formed as a conductive sheet.

40. The system as defined in claim 31 wherein said shield is formed as a conductive mesh.

41. The system as defined in claim 31 wherein said shield is formed from strips of conductive material.

42. The system as defined in claim 31 wherein said shield is a geometrically shaped thin member positioned adjacent to a navigational domain defined by the transmitter;

wherein the shield cancels the effects of the field influencing object positioned beyond the navigational domain.

43. The system as defined in claim 31 wherein the six delta coil sets include a long coil set and a short coil set, wherein each of the six delta coil sets is positioned about 120 degrees apart around a point.

* * * * *